United States Patent
Lee et al.

(10) Patent No.: US 9,751,933 B2
(45) Date of Patent: Sep. 5, 2017

(54) ANTIBODY SPECIFIC FOR CLEC14A AND USES THEREOF

(71) Applicant: SCRIPPS KOREA ANTIBODY INSTITUTE, Gangwon-do (KR)

(72) Inventors: Suk Mook Lee, Seoul (KR); Min kyoung Ki, Seoul (KR); Mee Hyun Jeoung, Gangwon-do (KR); Jong Rip Choi, Gangwon-do (KR)

(73) Assignee: SCRIPPS KOREA ANTIBODY INSTITUTE, Gangwon-do (KR)

( * ) Notice: Subject to any disclaimer, the term of this patent is extended or adjusted under 35 U.S.C. 154(b) by 182 days.

(21) Appl. No.: 14/407,756

(22) PCT Filed: Jun. 14, 2013

(86) PCT No.: PCT/KR2013/005272
§ 371 (c)(1),
(2) Date: Dec. 12, 2014

(87) PCT Pub. No.: WO2013/187724
PCT Pub. Date: Dec. 19, 2013

(65) Prior Publication Data
US 2015/0140001 A1    May 21, 2015

Related U.S. Application Data

(63) Continuation of application No. PCT/KR2012/008618, filed on Oct. 19, 2012.

(60) Provisional application No. 61/659,654, filed on Jun. 14, 2012.

(51) Int. Cl.
| C07K 16/00 | (2006.01) |
| C07K 16/46 | (2006.01) |
| C07K 16/18 | (2006.01) |
| C07K 14/705 | (2006.01) |
| C07K 16/28 | (2006.01) |
| A61K 47/48 | (2006.01) |
| C07K 7/08 | (2006.01) |
| C07K 14/435 | (2006.01) |
| G01N 33/53 | (2006.01) |

(52) U.S. Cl.
CPC ........ *C07K 16/18* (2013.01); *A61K 47/48538* (2013.01); *C07K 7/08* (2013.01); *C07K 14/435* (2013.01); *C07K 14/7056* (2013.01); *C07K 16/2851* (2013.01); *G01N 33/53* (2013.01); *C07K 2317/21* (2013.01); *C07K 2317/34* (2013.01); *C07K 2317/565* (2013.01); *C07K 2317/622* (2013.01); *C07K 2319/30* (2013.01)

(58) Field of Classification Search
None
See application file for complete search history.

(56) References Cited

U.S. PATENT DOCUMENTS

| 4,281,061 A * | 7/1981 | Zuk ...................... G01N 33/542 435/188 |
| 5,660,985 A | 8/1997 | Pieken et al. |
| 9,255,148 B2 * | 2/2016 | Bicknell ............ C07K 16/2851 |

FOREIGN PATENT DOCUMENTS

| WO | 99/07409 A1 | 2/1999 |
| WO | 99/32619 A1 | 7/1999 |
| WO | 00/44895 A1 | 8/2000 |
| WO | 00/44914 A1 | 8/2000 |
| WO | 01/29058 A1 | 4/2001 |
| WO | 01/36646 A1 | 5/2001 |
| WO | WO 2011/027132 | * 3/2011 |

OTHER PUBLICATIONS

Hein, Marco Yannic., Quantitative Proteomic Analysis of Endothelial Cells During Capillary Morphogenesis. University of Tübingen, Eberhard Karls Universität Tübingen Fakultät für Chemie und Pharmazie Interfakultäres Institut für Biochemie. Thesis. Jan. 2010. pp. 1-56.*
Campbell A, General properties and applications of monoclonal antibodies, Elsevier Science Publishers, section 1.1, pp. 1-32, 1984.*
Mura et al., Low shear stress induces the novel tumor endothelial marker CLEC14A that mediates cell migration and vascular development. Cancer Research, (Apr. 15, 2010) vol. 70, No. 8, Supp. SUPPL. 1. Abstract No. 1589.*
Barbas III et al., "Combinatorial Immunoglobulin Libraries on the Surface of Phage (Phabs): Rapid Selection of Antigen-Specific Fabs", Methods: A Companion to Methods in Enzymology, vol. 2, No. 2, pp. 119-124, (1991).
Cotten et al., "2'-O-methyl, 2'O-ethyl oligoribonucleotides and phosphorothioate oligodeoxyribonucleotides as inhibitors of the in vitro U7 snRNP-dependent mRNA processing event", Nucleic Acids Research, vol. 19, No. 10, pp. 2629-2635, (1991).
Ellington et al., "In vitro selection of RNA molecules that bind specific ligands", Nature, vol. 346, pp. 818-822, (1990).

(Continued)

*Primary Examiner* — Maher Haddad
(74) *Attorney, Agent, or Firm* — Vorys, Sater, Seymour & Pease LLP; Min Suhn Koh

(57) ABSTRACT

Provided is an antibody specifically binding to the CTLD (C-type lectin like domain) of clec14a (C-type lectin domain family 14, member A), a method for preparing the antibody, a composition for suppressing angiogenesis comprising the antibody, a method for suppressing angiogenesis by administering the antibody or the composition, a composition for preventing or treating cancer comprising the antibody, a method for treating cancer by administering the antibody or the composition, a composition for diagnosing cancer comprising the antibody, a kit for diagnosing cancer comprising the composition, a method for diagnosing cancer using the composition, a composition for suppressing angiogenesis comprising a material for inhibiting expression of clec14a, a kit for angiogenesis comprising the composition, a method for suppressing angiogenesis or treating cancer using the composition, and the use of the CTLD of clec14a as an epitope for an antibody suppressive of angiogenesis.

4 Claims, 18 Drawing Sheets

(56) References Cited

OTHER PUBLICATIONS

Guo et al., "CELL-SELEX: Novel Perspectives of Aptamer-Based Therapeutics", Int. J. Mol. Sci., vol. 9, pp. 668-678, (2008).
Hobbs et al., "Polynucleotides Containing 2'-Amino-2'-deoxyribose and 2'-Azido-2'deoxyribose", Biochemistry, vol. 12, No. 25, pp. 5138-5145, (1973).
Köhler et al., "Continuous cultures of fused cells secreting antibody of predefined specificity", Nature, vol. 256, pp. 495-497, (1975).
Kopetz et al., "Phase II Trial of Infusional Fluorouracil, Irinotecan, and Bevacizumab for Metastatic Colorectal Cancer: Efficacy and Circulating Angiogenic Biomarkers Associated With Therapeutic Resistance", J Clin Oncol, vol. 28, pp. 453-459, (2009).
Lucio-Eterovic et al., "Mediators of Glioblastoma Resistance and Invasion during Antivascular Endothelial Growth Factor Therapy", Clin Cancer Res, vol. 15, No. 14, pp. 4589-4599, (2009).
Mura et al., "Identification and angiogenic role of the novel tumor endothelial marker CLEC14A", Oncogene, pp. 1-13, (2011).
Rho et al., "Clec14a is specifically expressed in endothelial cells and mediates cell to cell adhesion", Biochemical and Biophysical Research Communications, vol. 404, pp. 103-108, (2011).
Smith, "Filamentous Fusion Phage: Novel Expression Vectors That Display Cloned Antigens on the Virion Surface", Science, vol. 228, pp. 1315-1317, (1985).
Smith et al., "Phage Display", Chem. Rev., vol. 97, pp. 391-410, (1997).
Sproat et al., "New synthetic routes to synthons suitable for 2'-O-allyloligoribonucleotide assembly", Nucleic Acids Research, vol. 19, No. 4, pp. 733-738, (1991).
Tuerk et al., "Systematic Evolution of Ligands by Exponential Enrichment: RNA Ligands to Bacteriophage T4 DNA Polymerase", Science, New Series, vol. 249, No. 4968, pp. 505-510, (1990).
Van Meter et al., "A Monoclonal Antibody That Inhibits Translation in Sf21 Cell Lysates Is Specific for Glyceraldehyde-3-Phosphate Dehydrogenase", Archives of Insect Biochemistry and Physiology, vol. 69, pp. 107-117, (2008).
Vestweber, "Lymphocyte trafficking through blood and lymphatic vessels: more than just selectins, chemokines and integrins", Eur. J. Immunol., vol. 33, pp. 1362-1365, (2003).
Weiss et al., "Antisense RNA gene therapy for studying and modulating biological processes", CMLS, Cell. Mol. Life Sci., vol. 55, pp. 334-358, (1999).
Winter et al., "Making Antibodies by Phage Display Technology", Annu. Rev. Immunol., vol. 12, pp. 433-455, (1994).
Zwick et al., "Identification and Characterization of a Peptide That Specifically Binds the Human, Broadly Neutralizing Anti-Human Immunodeficiency Virus Type 1 Antibody b12", Journal of Virology, vol. 75, No. 14, pp. 6692-6699, (2001).

\* cited by examiner

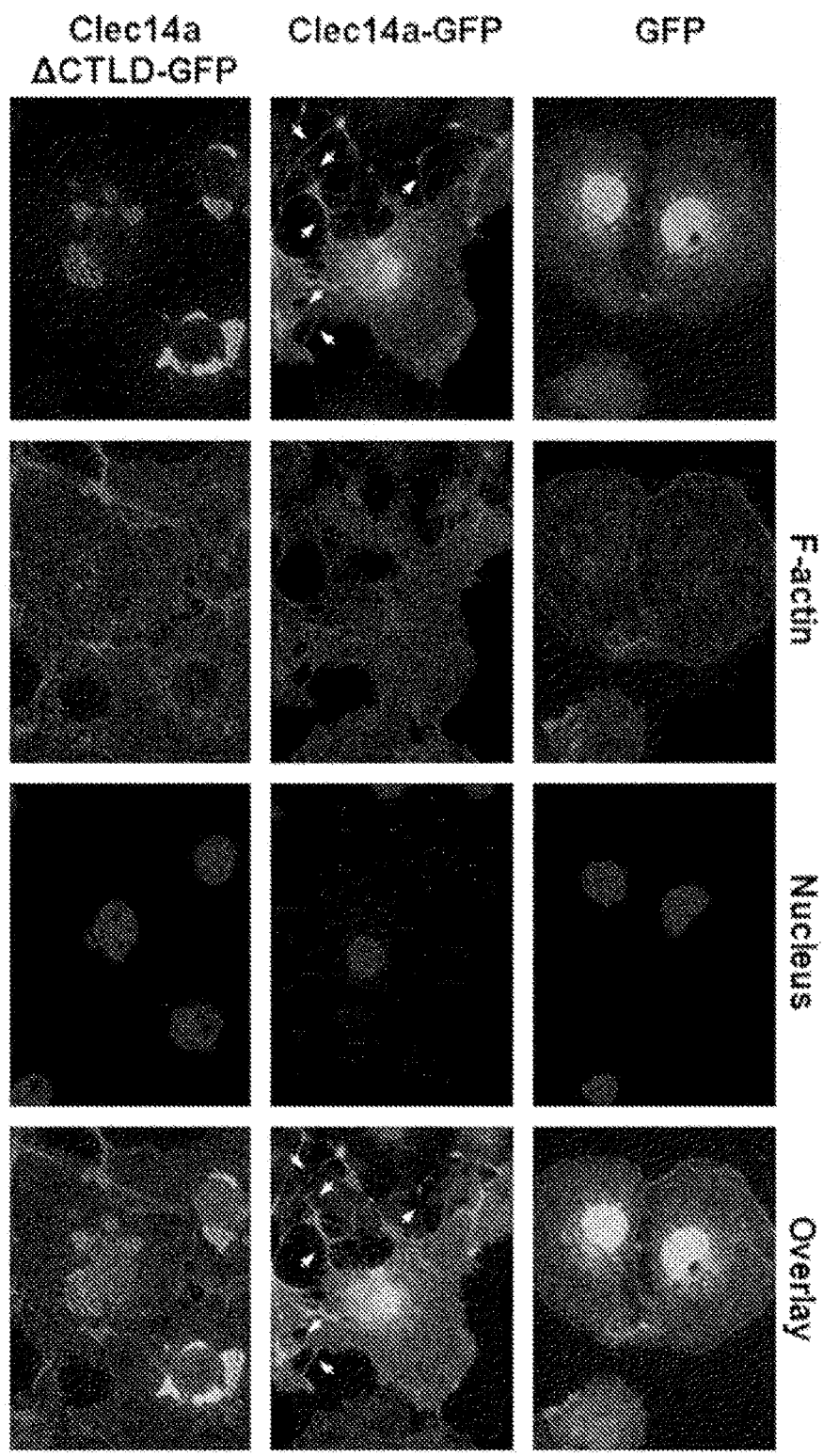

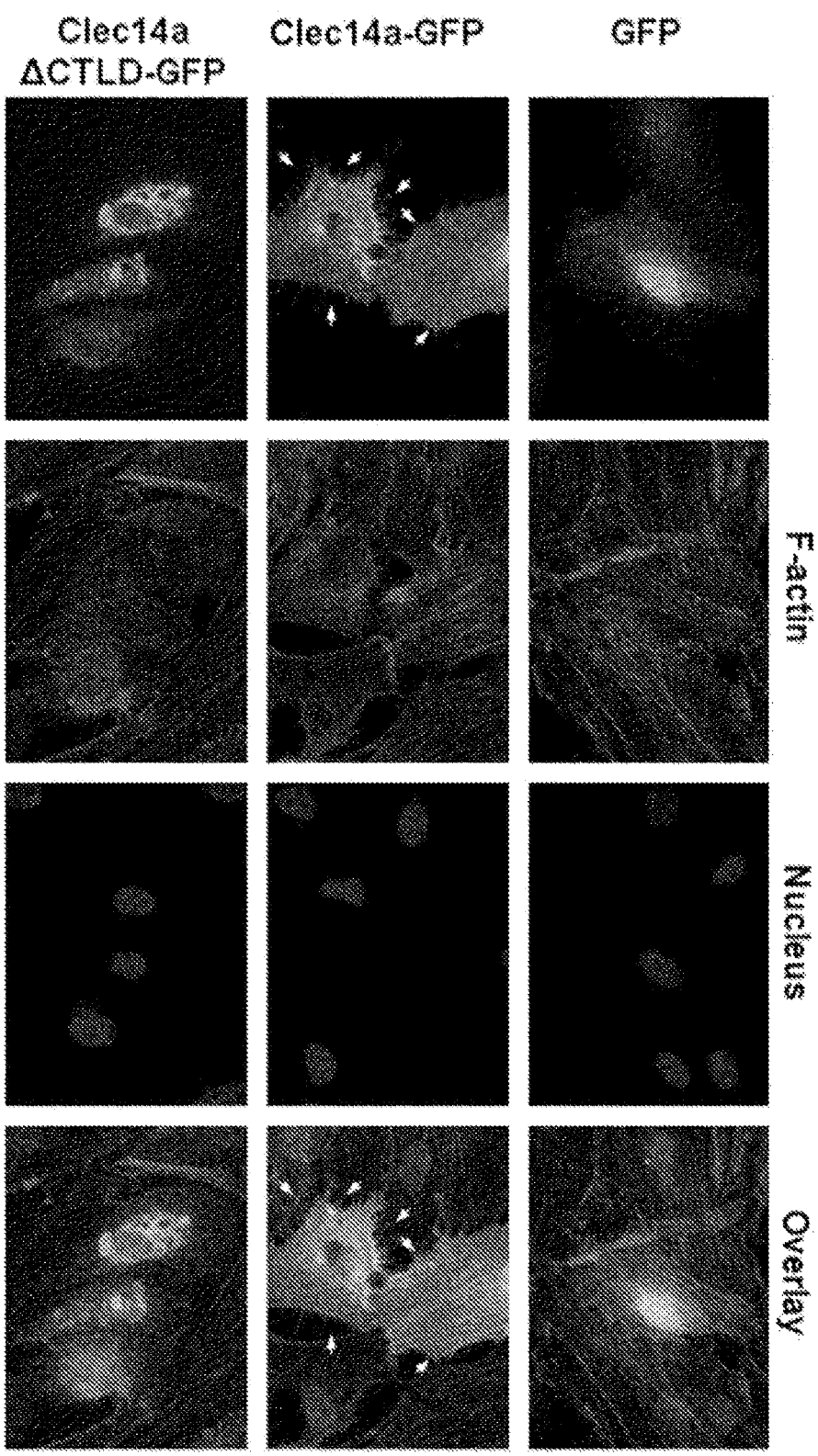

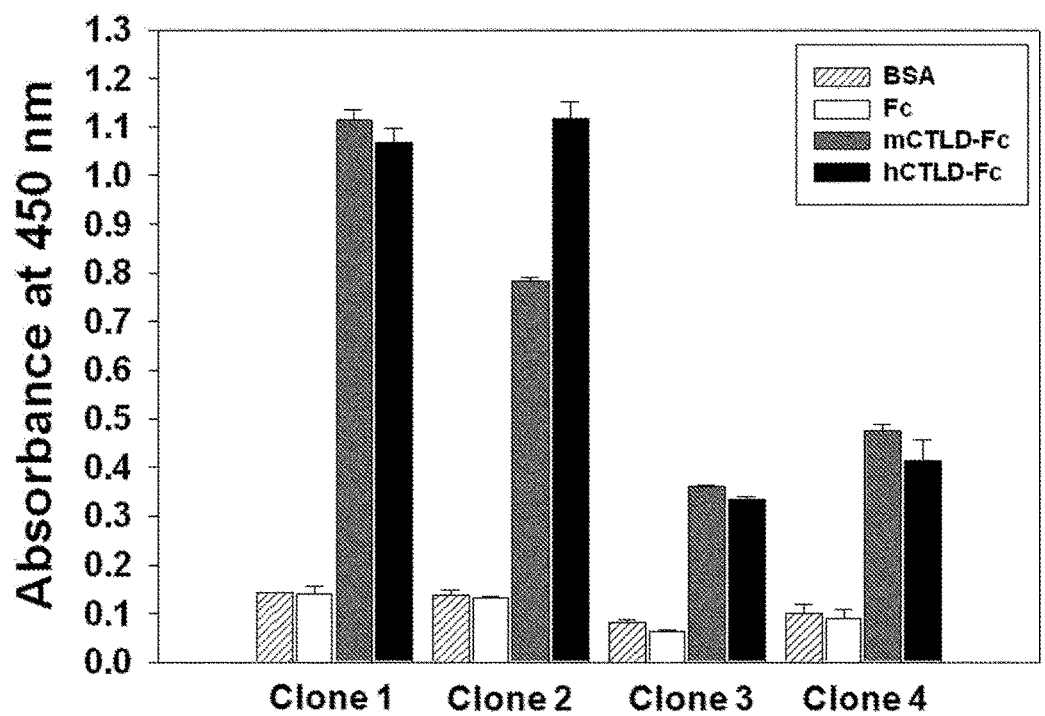

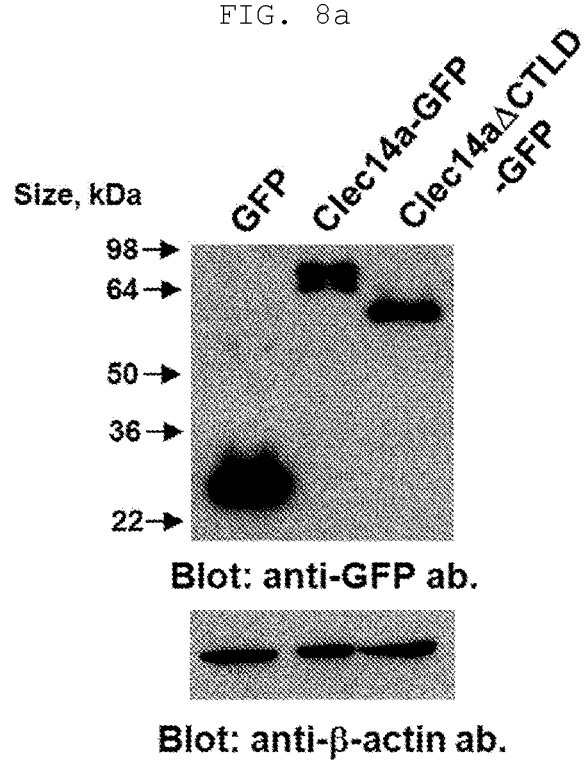

FIG. 10b
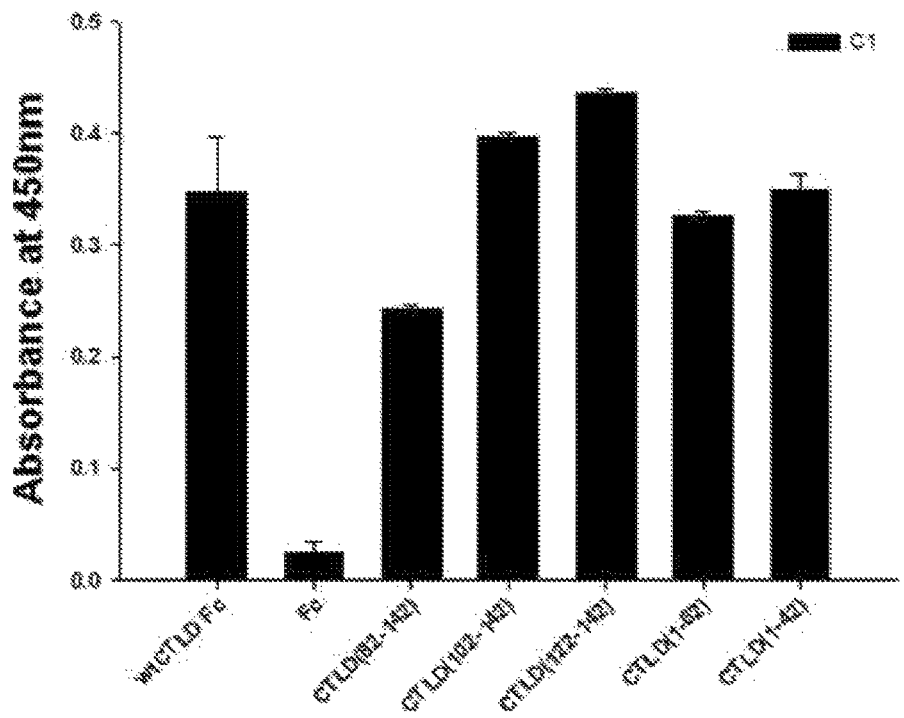
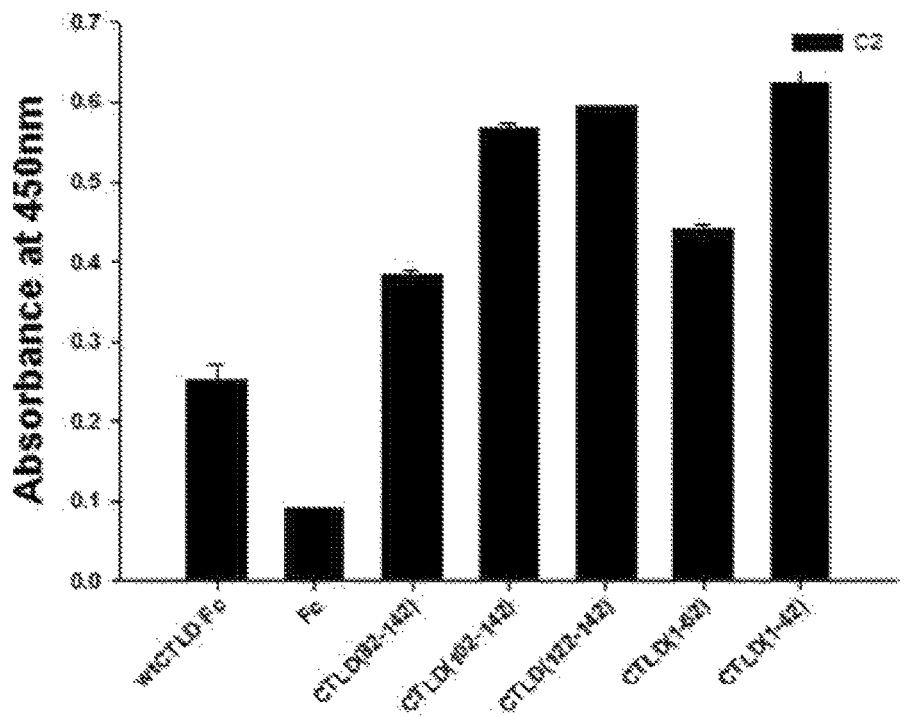

ANTIBODY SPECIFIC FOR CLEC14A AND USES THEREOF

The Sequence Listing submitted in text format (.txt) filed on Dec. 24, 2014, named "SequenceListing.txt", created on Dec. 24, 2014, 51.9 KB), is incorporated herein by reference.

TECHNICAL FIELD

The present invention relates to a novel antibody specifically binding to the C-type lectin domain family 14, member A (clec14a) and uses thereof. More particularly, the present invention relates to an antibody specifically binding to the C-type lectin like domain (CTLD) of clec14a, a method for preparing the antibody, a composition for the suppression of angiogenesis comprising the antibody, a method for suppressing angiogenesis by administering the antibody or the composition, a composition for preventing or treating cancer comprising the antibody, a method for treating cancer by administering the antibody or the composition, a composition for diagnosing cancer comprising the antibody, a kit for diagnosing cancer comprising the composition, a method for diagnosing cancer using the composition, a composition for the suppression of angiogenesis comprising a material for inhibiting expression of clec14a, a kit for angiogenesis comprising the composition, a method for suppressing angiogenesis or treating cancer using the composition, and the use of the CTLD of clec14a as an epitope for an antibody suppressive of angiogenesis.

BACKGROUND ART

The rapid recent development of recombinant antibody technology has produced approximately 30 antibodies that have been approved for human therapy and more than 270 that are currently in clinical development worldwide for a wide range of diseases. However, conventional antibody screening remains time- and labor-intensive and expensive. Traditionally, extracellular regions of target proteins have been used to screen antibodies. Consequently, most selected antibodies bind to cells, but are not functional antibodies with therapeutic potential. Due to recent advances in molecular biology and protein biochemistry, a large amount of information on protein domains and motifs that could link these structures to cell functions, is available. Use of a functional domain to screen recombinant antibodies may be an effective means of identifying functional antibodies and investigating underlying modes of action.

Tumor angiogenesis plays an important role in tumor progression. Vascular endothelial growth factor (VEGF) and epidermal growth factor receptor (EGFR) are key factors in angiogenesis, and targeting angiogenesis has become a promising strategy for cancer treatment. The anti-VEGF antibody bevacizumab has been used to treat patients with metastatic colorectal cancer, renal cell carcinoma, non-small-cell lung cancer, and malignant brain glioma. Cetuximab, an anti-EGFR antibody, may inhibit endothelial cell to cell contact and expression of angiogenic factors such as VEGF, interleukin-8, and basic fibroblast growth factor. However, due to the redundancy of tumor-secreted angiogenic factors, including placental growth factor, angiopoietin, basic fibroblast growth factor, and hepatocyte growth factor, these drugs generate a resistant phenotype in tumors (Kopetz S, et al., Phase II trial of infusional fluorouracil, irinotecan, and bevacizumab for metastatic colorectal cancer: efficacy and circulating angiogenic biomarkers associated with therapeutic resistance. Journal of Clinical Oncology. 28(3):453-9; Lucio-Eterovic A K, et al., Mediators of glioblastoma resistance and invasion during antivascular endothelial growth factor therapy. Clinical Cancer Research. 2009; 15(14):4589-99).

The human VEGF antibody, bevacizumab, is now being used to treat patients with a variety of cancers. However, because the VEGF receptor (VEGFR) is also expressed on normal cells, its use is likely to be associated with adverse effects including hypertension, proteinuria, and gastrointestinal perforation. Adverse effects may also limit the therapeutic use of many antibodies against pro-angiogenic factors such as VEGFR-2 and angiopoietin-2. Consequently, identification of new cancer-specific targets for treating cancer patients by inhibition of angiogenesis is critical for developing therapeutic antibodies with fewer adverse effects.

In addition, bevacizumab and cetuximab are therapeutic antibodies that suppress angiogenesis by inhibiting interaction of soluble angiogenic growth factors and their receptors. However, long-term use of these drugs generates a resistant tumor phenotype due to redundancy of tumor cell-secreted pro-angiogenic growth factors. This may pose the greatest challenge to use of antibodies against soluble growth factors in patients requiring long-term therapy.

Clec14a is a type I transmembrane protein, the extracellular domain of which consists of a C-type lectin-like domain (CTLD), a series of epidermal growth factorlike domains, and a sushi-like domain. Several reports suggest a role by clec14a in tumor angiogenesis. Rho et al. reported that clec14a is endothelial cell-specific and may play a key role in cell to cell contact in angiogenesis (Rho S S, et al., Clec14a is specifically expressed in endothelial cells and mediates cell to cell adhesion. Biochemical & Biophysical Research Communications. 404(1):103-8). Mura et al. showed that clec14a is critical for regulating pro-angiogenic phenotypes associated with filopodium formation, cell migration, and endothelial tube formation; this group also identified clec14a as a tumor endothelial cell marker not expressed on the endothelium of normal tissues (Mura M, et al., Identification and angiogenic role of the novel tumor endothelial marker CLEC14A. Oncogene. 31(3):293-305).

Despite increasing interest in clec14a in recent years, its molecular mechanism has not been clearly identified. Studies on the functional portion or domain of cle14a which accounts for the angiogenesis must be conducted so as to excavate and develop clinically applicable antibodies. In this context, there is a pressing demand for a monoclonal antibody that specifically binds mouse and human clec14a and that is convertible into a humanized antibody or human antibody for preclinical and clinical study. Preferably, an antibody which is clinically applicable to the inhibition of tumor angiogenesis and thus to the treatment of cancer is needed. In addition, a novel part which suppresses tumor angiogenesis is needed to identify and thus further the suppression of angiogenesis and treatment of cancer.

The above information disclosed in this Background section is only for enhancement of understanding of the background of the present invention, and therefore it may contain information that does not form the prior art that is already known to a person of ordinary skill in the art.

DISCLOSURE OF INVENTION

Technical Problem

The present inventors first identified CTLD functions in cell migration and filopodium formation, which are key events of angiogenesis. Using phage display technology the present inventors developed recombinant human antibodies against human and mouse clec14a CTLDs. Functional assays showed that the antibodies specifically inhibited endothelial cell migration and tube formation without affecting viability or activation. Finally, the present inventors propose a mechanism of action, whereby the antibodies may inhibit angiogenesis by modulating CTLD-mediated cell to cell interaction and down-regulating clec14a expression on the surface of endothelial cells. These results demonstrate the functional significance of CTLD in angiogenesis and the potential of CTLD-specific human antibodies to block clec14a-mediated tumor angiogenesis.

Solution to Problem

To achieve the above object, the present invention provides an antibody which binds specifically to clec14a (C-type lectin domain family 14, member A).

The present invention also provides a nucleic acid encoding said antibody.

The present invention also provides a vector comprising said nucleic acid.

The present invention also provides a host cell comprising said vector or said nucleic acid.

The present invention also provides a method of producing said antibody, comprising culturing said host cell such that the nucleic acid is expressed to produce the antibody.

The present invention also provides an antibody-drug conjugate comprising said antibody attached to a drug.

The present invention also provides a pharmaceutical composition for preventing or treating angiogenesis-related disease, comprising said antibody.

The present invention also provides a use of said antibody for preparation of a pharmaceutical composition for preventing or treating angiogenesis-related disease.

The present invention also provides said antibody for use in preventing or treating angiogenesis-related disease.

The present invention also provides a method for treating angiogenesis-related disease, comprising administering said antibody or said pharmaceutical composition to a subject in need thereof.

The present invention also provides a composition for the suppression of angiogenesis, comprising said antibody.

The present invention also provides a use of said antibody for preparation of a composition for suppression of angiogenesis.

The present invention also provides said antibody for use in suppression of angiogenesis.

The present invention also provides a method for suppressing angiogenesis, comprising administering said antibody or said pharmaceutical composition to a subject in need thereof.

The present invention also provides a diagnostic composition for angiogenesis-related disease, comprising said antibody.

The present invention also provides a use of said antibody for preparation of a diagnostic composition for angiogenesis-related disease.

The present invention also provides said antibody for use in in-vitro diagnosis of angiogenesis-related disease.

The present invention also provides a diagnostic kit for angiogenesis-related disease, comprising said diagnostic composition.

The present invention also provides a method for diagnosing angiogenesis-related disease, comprising detecting clec14a through antigen-antibody complexes in an isolated biological sample from a subject with suspected angiogenesis-related disease.

The present invention also provides a polypeptide, comprising isolated CTLD of clec14a, serving as an epitope capable of inducing production of an antibody suppressive of angiogenesis.

The present invention also provides a polypeptide, comprising isolated N-terminal or C-terminal of CTLD of clec14a as an epitope capable of inducing production of an antibody suppressive of angiogenesis.

The present invention also provides a polypeptide, comprising an amino acid fragment from 1st amino acid to 42nd amino acid in CTLD of clec14a or a amino acid fragment from 122nd amino acid to 142nd amino acid in CTLD of clec14a as an epitope capable of inducing production of an antibody suppressive of angiogenesis.

The present invention also provides a method for preparing an antibody binding specifically to clec14a (C-type lectin domain family 14, member A), comprising: biopanning using said polypeptide as an epitope.

The present invention also provides a composition for suppressing angiogenesis, comprising a material for inhibiting the expression of clec14a.

The present invention also provides a kit for suppressing angiogenesis, comprising said composition.

The present invention also provides a method for suppressing angiogenesis, comprising administering said composition to a subject in need thereof.

The present invention also provides a method for treating angiogenesis-related disease, comprising administering said composition to a subject in need thereof.

The present invention also provides a use of said material for inhibiting the expression of clec14a for preparation of a composition for suppressing of angiogenesis.

The present invention also provides said material for inhibiting the expression of clec14a for use in suppression of angiogenesis.

The present invention also provides a pharmaceutical composition for preventing or treating angiogenesis-related disease, comprising fusion protein of CTLD of clec14a and Fc.

The present invention also provides a use of said fusion protein of CTLD of clec14a and Fc for preparation of a pharmaceutical composition for preventing or treating angiogenesis-related disease.

The present invention also provides said fusion protein of CTLD of clec14a and Fc for use in preventing or treating angiogenesis-related disease.

The present invention also provides a method for treating angiogenesis-related disease, comprising administering said fusion protein of CTLD of clec14a and Fc or said pharmaceutical composition to a subject in need thereof.

Other features and embodiments of the present invention will be more apparent from the following detailed descriptions and the appended claims.

BRIEF DESCRIPTION OF THE DRAWINGS

FIG. 2. shows the effect of clec14a CTLD on filopodium formation. COS-7 cells (a) and HUVECs (b) transfected with GFP, clec14a-GFP, and clec14aΔCTLD-GFP were fixed, stained with rhodamine-phalloidin and Hoechst, and examined by fluorescence microscopy (1000×). Arrows indicate regions of filopodium formation. Results are representative of three independent experiments.

FIG. 4. shows cross-species reactivity of clec14a-CTLD IgGs to human and mouse CTLDs. ELISA was performed with purified, selected IgG scFv clones (clones 1-4) on 96-well microtiter plates coated with hCTLD-Fc (■, black), mCTLD-Fc (■, grey), and Fc (□). BSA (☒) served as a background control. Values represent mean±SD of triplicate measurements from one of two independent experiments.

BEST MODE FOR CARRYING OUT THE INVENTION

In accordance with an aspect thereof, the present invention provides an antibody binding specifically to clec14a (C-type lectin domain family 14, member A).

Preferably, the antibody may be an antibody binding specifically to CTLD (C-type lectin like domain) of clec14a (C-type lectin domain family 14, member A).

As used herein, the term "antibody" means a protein molecule which comprises an immunoglobulin molecule immunologically reactive to a certain antigen, serving as a receptor specifically recognizing the antigen, and is intended to encompass polyclonal antibodies, monoclonal antibodies, whole antibodies and antibody fragments. In addition, chimeric antibodies (e.g., humanized murine antibodies), bivalent or bispecific molecules (e.g., bispecific antibodies), diabodies, triabodies, and tetrabodies fall within the scope of the antibody useful in the present invention. A whole antibody consists of two full-length light chains and two full-length heavy chains, with disulfide bonds between the light and heavy chains. In mammals, there are five antibody isotypes known as IgA, IgD, IgE, IgM and IgG, and IgG is further divided into four subtypes of IgG1, IgG2, IgG3 and IgG4. The term "antibody fragment" refers to a fragment which retains at least the antigen-binding function, and may include Fab, F(ab'), F(ab')2, and Fv. Fab is composed of one variable region of each of the heavy and the light chain, the constant domain of the light chain, and the first constant domain (CH1) of the heavy chain, with an antigen binding site. Fab' is different from Fab in that it further comprises at least one cysteine residue at the C-terminus of the CH1 domain of the heavy chain. F(ab')2 consists of two molecules of Fab' with a disulfide bond between the cysteine residues of the hinge region. Fv (variable fragment), composed of one variable region of each of the heavy and the light chain, is the smallest antibody fragment containing the original specificity of the parent immunoglobulin. Disulfidestabilized Fv (dsFv) is formed by linking the variable region of the heavy chain to the variable region of the light chain via a disulfide bond. Single chain Fv (scFV) is an Fv in which the respective variable regions of the heavy and the light chain are covalently connected by a peptide linker. These antibody fragments can be obtained using proteases (for example, digestion of a whole antibody with papain or pepsin affords Fab or F(ab')2, respectively), and preferably may be constructed by genetic recombination technology.

Figure 3A:
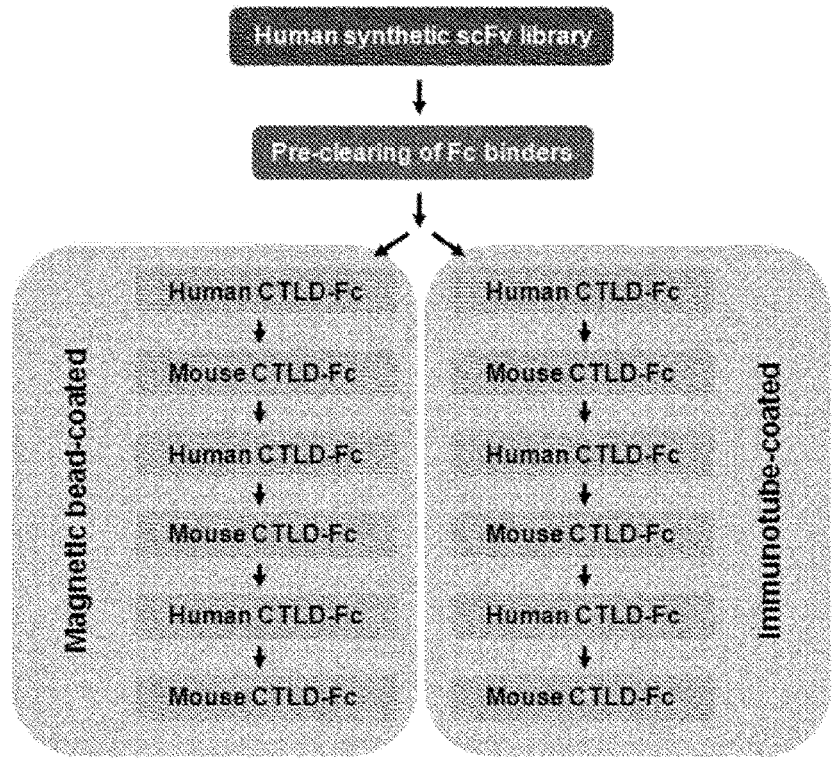
FIG. 3. shows isolation of scFv clones specific to human and mouse CTLDs. a. A human synthetic scFv antibody library was precleared of Fc binders and screened by alternative biopanning with recombinant hCTLD-Fc or mCTLD-Fc. b-d. Ninety-six phage clones (1-96) displaying scFv were randomly selected and the supernatants were analyzed by phage ELISA. Reactivity of the selected scFv clones to human and mouse CTLDs was assayed by measuring absorbance at 450 nm. Arrows indicate scFv clones reactive to hCTLD-Fc (■, black) and mCTLD-Fc (■, grey), and not reactive to Fc (□). BSA (☒) served as a background control.

Conventionally, antibody screening has been conducted using the overall extracellular regions of target proteins, resulting in problems with the separation of antibodies. In the present invention, an improvement in antibody screening is made with the use of a functional domain of the target protein, so as to produce antibodies more quickly. In one embodiment of the present invention, the CTLD of clec14a was identified as playing an important role in angiogenesis and was used in antibody screening. The process of antibody screening is schematically illustrated in FIG. 3a.

The term "monoclonal antibody", as used herein, refers to an antibody molecule with a uniform molecular composition, obtained from a substantially identical population of antibodies, which shows binding specificity and affinity for a single epitope.

Typically, an immunoglobulin has a basic structural unit composed two heavy and two light chains. Each heavy chain comprises one variable region (also known as "region") and three constant domains while each light chain is composed of one variable region and one constant domain. The variable region of each of the light and the heavy chain comprises three complementarity-determining regions (hereinafter referred to as "CDRs") and four framework regions. CDRs function to bind to an epitope of an antibody. CDRs on each chain start from the N terminus and are arranged sequentially as CDR1, CDR2, and CDR3. They are discriminated by the chain on which they are positioned.

As used herein, the term "human antibody" is a molecule which consists entirely of the amino acid sequence of all components of human immunoglobulin, including CDRs, framework regions, and the like. In the therapy of human diseases, human antibodies have at least three potential advantages. First, human antibodies more preferably interact with the human immune system to more effectively destroy target cells by, for example, complement-dependent cytotoxicity (CDC) or antibody-dependent cell-mediated cytotoxicity (ADCC). Another advantage is that the human immune system does not recognize human antibodies as foreign molecules. Moreover, the half-lives of human antibodies are similar to those of naturally occurring antibodies in the human circulatory system even when they are administered in smaller doses or with less frequency. Therefore, the antibody according to the present invention may be preferably a human monoclonal antibody that can be useful for the therapy of angiogenesis-related diseases or cancer not only because it has potent affinity for clec14a, preferably clec14a-CTLD expressed on human endothelial cells which effectively inhibits clec14a-mediated angiogenesis, but also because it shows low immunogenicity because both of its heavy and light chains are derived from a human.

The term "clec14a (C-type lectin domain family 14, member A)," as used herein, means a member of the C-type lectin/C-type lectin-like domain (CTL/CTLD) superfamily. Clec14a is a type I transmembrane protein, the extracellular domain of which consists of a C-type lectin-like domain (CTLD), a series of epidermal growth factor-like domains, and a sushi-like domain. Information about clec14a may be obtained from a public database such as NCBI GenBank. For example, human clec14a may have Gene ID No 161198, but is not limited thereto. Clec14a is known to be involved in cell to cell adhesion and angiogenesis, but its concrete mechanism and substantial domains responsible for angiogenesis have remained unidentified. It is the present inventors that first found that CTLD, a domain stretching from amino acids 31st to amino acids 172nd on the amino acid sequence of cle14a, plays a key role in angiogenesis.

The term "C-type lectin-like domain (CTLD) of clec14a (C-type lectin domain family 14, member A)," as used herein, is interchangeable with the term "clec14a-CTLD" or "clec14a CTLD".

In accordance with another aspect thereof, the present invention provides an isolated polypeptide of clec14a (C-type lectin domain family 14, member A)-CTLD (C-type lectin like domain) as an epitope available for the suppression of angiogenesis. Preferably, clec14a may be derived from human, chimpanzee or mouse.

As used herein, the term "epitope" refers to the part of an antigen that determines antigen specificity, and may be interchangeably used with an antigenic determinant or an antigen determining site. For the purpose of the present invention, the epitope refers to CTLD having an amino acid sequence stretching from amino acids 31st to amino acids 172nd on the amino acid sequence of clec14a, which is available for the suppression of angiogenesis, or may refer to a polypeptide having the same function with the CTLD. Thus the extra region of CTLD may be included. So long as it has the same role in CTLD, any polypeptide, for example, having an identity of 80%, 85%, 90%, 95%, 98% or 99% or higher with the amino acid sequence, may be used as the epitope. Amino acid sequences of human, mouse and chimpanzee CTLDs, stretching from amino acids 31st to amino acids 172nd, are given in Table 1, and named SEQ ID NOS: 9, 10, and 133, respectively. The present inventors first found that the amino acid sequences of SEQ ID NOS: 9, 10 and 133 can serve as epitopes which can be used to produce antibodies suppressive of angiogenesis.

Figure 10A:
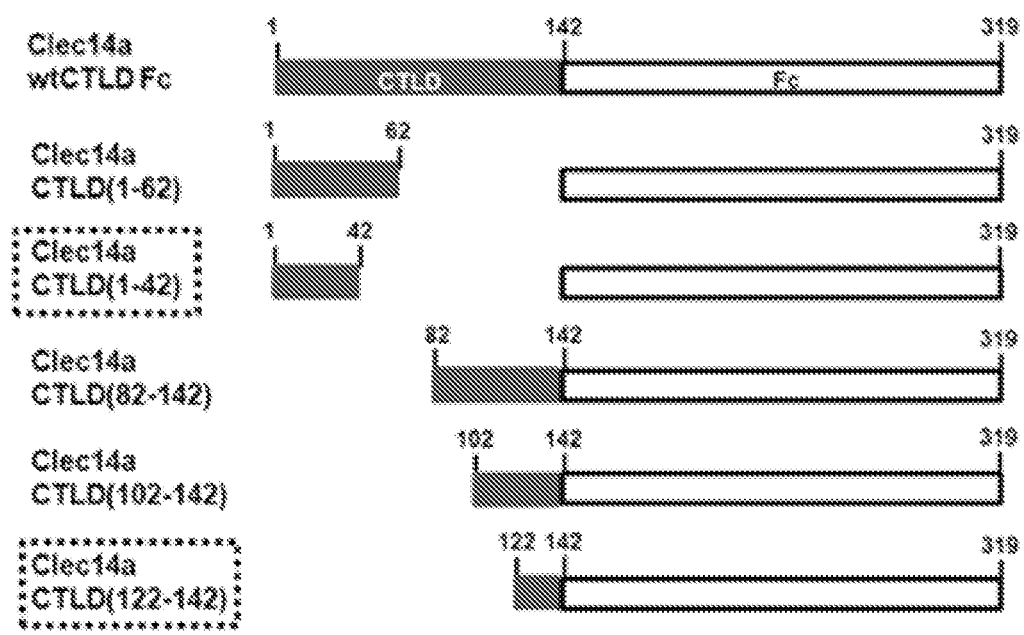
FIG. 10. shows the specificity of clec14a-CTLD IgGs to partial fragment of CTLD of clec14a. a. fusion proteins of Fc and partial fragment of CTLD of clec14a. b. the graph showing specificity of clec14a-CTLD IgGs of both clone 1 (upper graph) and clone 2 (lower graph) to the fusion proteins of Fc and partial fragment of CTLD of clec14a, wtCTLD-Fc and Fc, respectivity.

Also, in one preferred embodiment, it is suggested that the N-terminal or C-terminal region of CTLD can serve as epitopes which can be used to produce antibodies suppressive of angiogenesis (FIG. 10b). Preferably, the N-terminal region of CTLD may be a region comprising an amino acid fragment from 1st amino acid to 42nd amino acid in CTLD or an amino acid fragment from 1st amino acid to 62nd amino acid in CTLD. Preferably, the C-terminal region of CTLD may be a region comprising an amino acid fragment from 82nd amino acid to 142nd amino acid in CTLD, an amino acid fragment from 62nd amino acid to 142nd amino acid in CTLD, or an amino acid fragment from 122nd amino acid to 142nd amino acid in CTLD.

The antibodies may bind specifically to clec14a-CTLD or its effective fragments to inhibit angiogenesis, the present inventors suggest that clec14a-CTLD is a unique domain that regulates angiogenesis in a CTLD-CTLD interaction-dependent manner. First, clec14a-CTLD, particularly amino acids 31-172, played a key role in clec14a-mediated cell migration by regulating actin cytoskeletal rearrangement. Second, consistent with our observation that clec14a-CTLD IgG specifically suppresses clec14a-mediated cell-cell contacts. Third, clec14a modulation by clec14a-CTLD IgG specifically inhibited HUVEC migration and tube formation. Finally, formation of clec14a CTLD-CTLD complexes was specifically inhibited by clec14a-CTLD IgG.

The high-affinity clec14a-CTLD IgGs specifically inhibited endothelial cell migration and tube formation without affecting cell viability and activation. clec14a is expressed exclusively on endothelial cells and may be a specific, tumor endothelial cell marker. It is reasonable to speculate that the clec14a-CTLD antibodies might have fewer adverse effects in normal endothelium, target clec14a expressed exclusively on tumor endothelium, and suppress angiogenesis during clec14a-mediated tumor progression. Further, bevacizumab and cetuximab are therapeutic antibodies that suppress angiogenesis by inhibiting interaction of soluble angiogenic growth factors and their receptors. However, long-term use of these drugs generates a resistant tumor phenotype due to redundancy of tumor cell-secreted pro-angiogenic growth factors. This may pose the greatest challenge to use of antibodies against soluble growth factors in patients requiring long-term therapy. Clec14a is a type I transmembrane protein critical for endothelial cell to cell contact. The clec14a-CTLD IgG developed here specifically blocked CTLD-CTLD interaction in a concentration-dependent manner and clec14a cross-linking by IgG induced clec14a down-regulation on endothelial cell membranes. Within 2 hr of cross-linking, clec14a-CTLD IgG appeared in a dot-like pattern inside HUVECs, suggesting antibody-induced endocytosis. Thus, clec14a-CTLD IgG may have a dual mechanism of action in suppressing angiogenesis.

Accordingly, the antibody can suppress angiogenesis preferably by inhibiting cell migration, tube formation, or cell-cell contact, more preferably by inhibiting clec14a-mediated cell migration, tube formation, clec14a-mediated cell-cell contact, or clec14a CTLD-CTLD complex formation, or inducing the down-regulation of clec14a on the surface of vascular endothelial cells.

Having no influence on the viability and activation of endothelial cells (FIGS. 6A and 6B), the antibody of the present invention can be used as therapeutic antibodies.

Figure 7A:
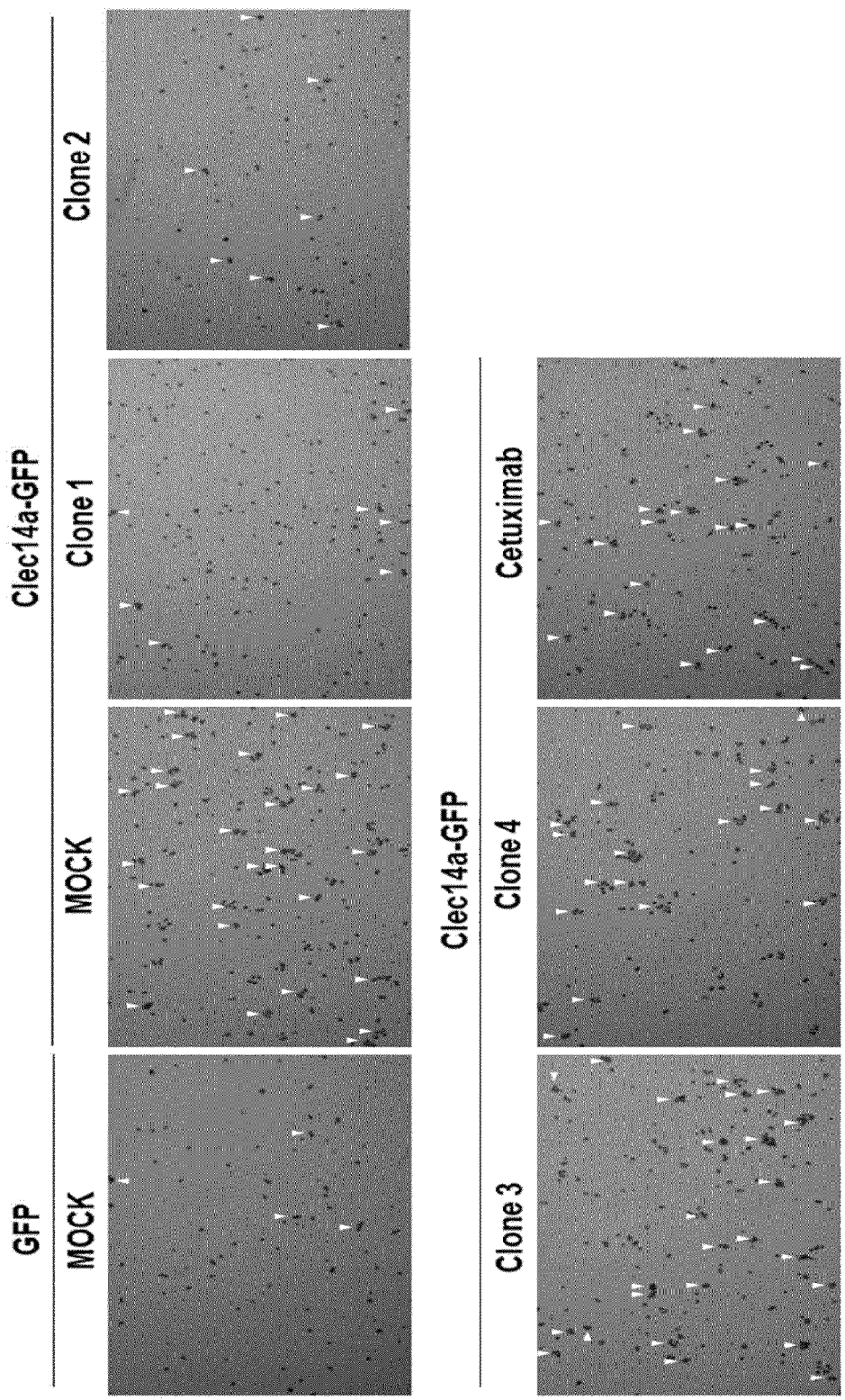
FIG. 7. shows the effect of clec14a-CTLD IgGs on clec14a-mediated cell-cell contact. a. HEK293F cells transfected with GFP and clec14a-GFP were incubated in the absence (MOCK) or presence of clec14a-CTLD IgGs or cetuximab for 8 hr. Cell aggregates (mass>4 cells; arrowheads) were counted under a optical microscope. The number of aggregates per field is shown in b. Values represent mean±SD of triplicate measurements from one of three independent experiments.
Figure 7B:
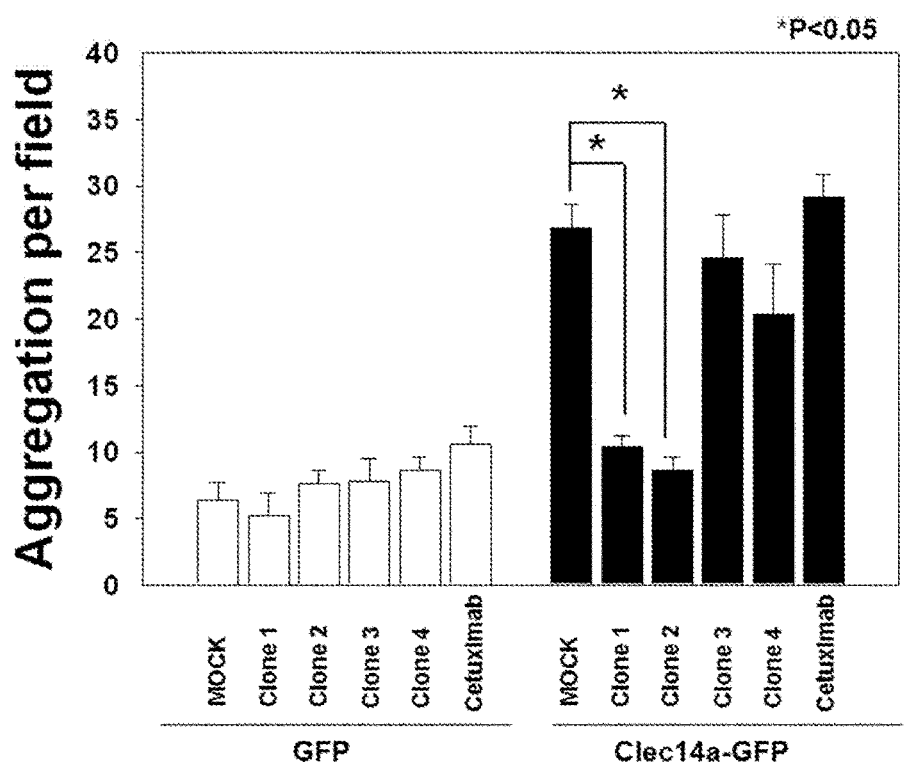
Figure 8B:
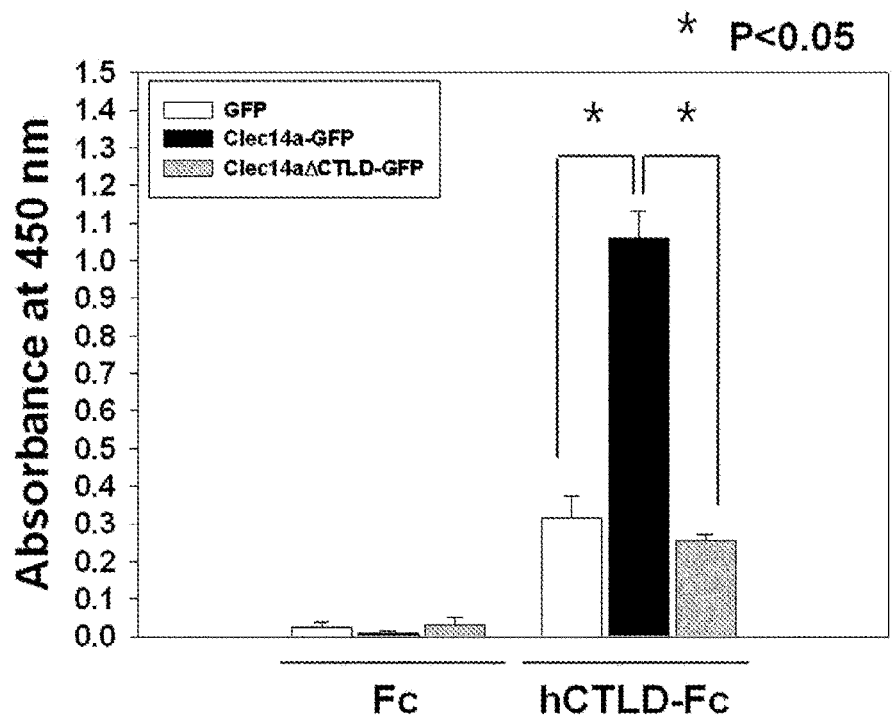
FIG. 8. shows the effect of clec14a-CTLD IgG on CTLD-CTLD interaction. a. Lysates of COS-7 cells transfected with GFP, clec14a-GFP, or clec14aΔCTLD-GFP were analyzed by immunoblotting with anti-GFP or anti-β-actin antibody. b. COS-7 cells expressing GFP (white), clec14a-GFP (black), or clec14aΔCTLD-GFP (light gray) were incubated with 0.15 µg hCTLD-Fc or Fc and CTLD-CTLD interaction was measured by ELISA. c. Lysates of COS-7 cells transfected with GFP or clec14a-GFP were incubated with hCTLD-Fc that had been pre-incubated with increasing concentrations of clec14a-CTLD IgG (clone 1). Values represent mean±SD of triplicate measurements from one of three independent experiments.
Figure 8C:
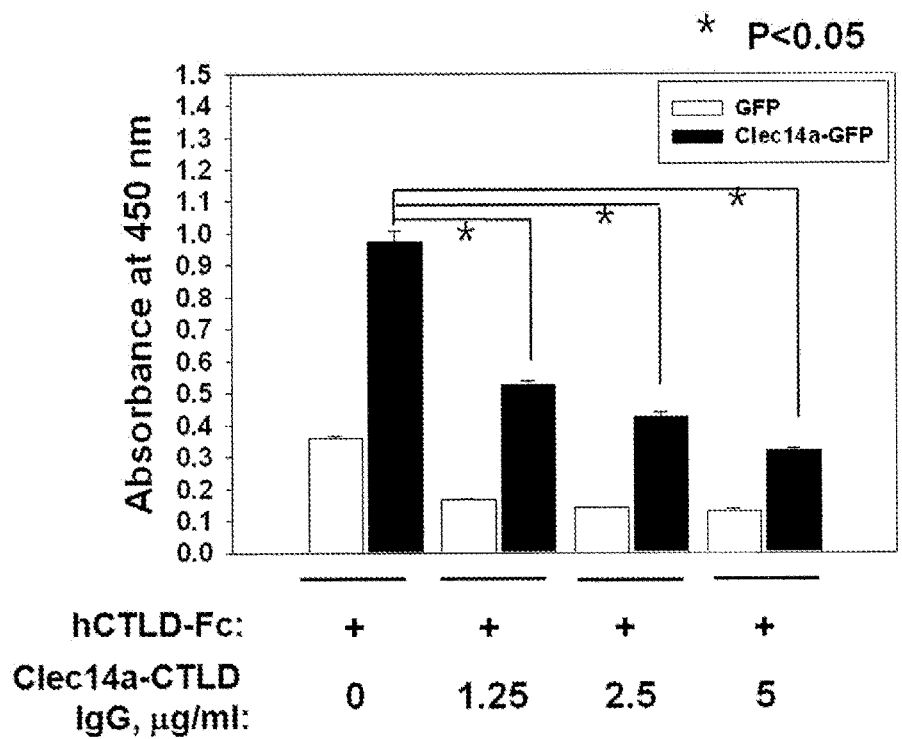
Figure 9A:
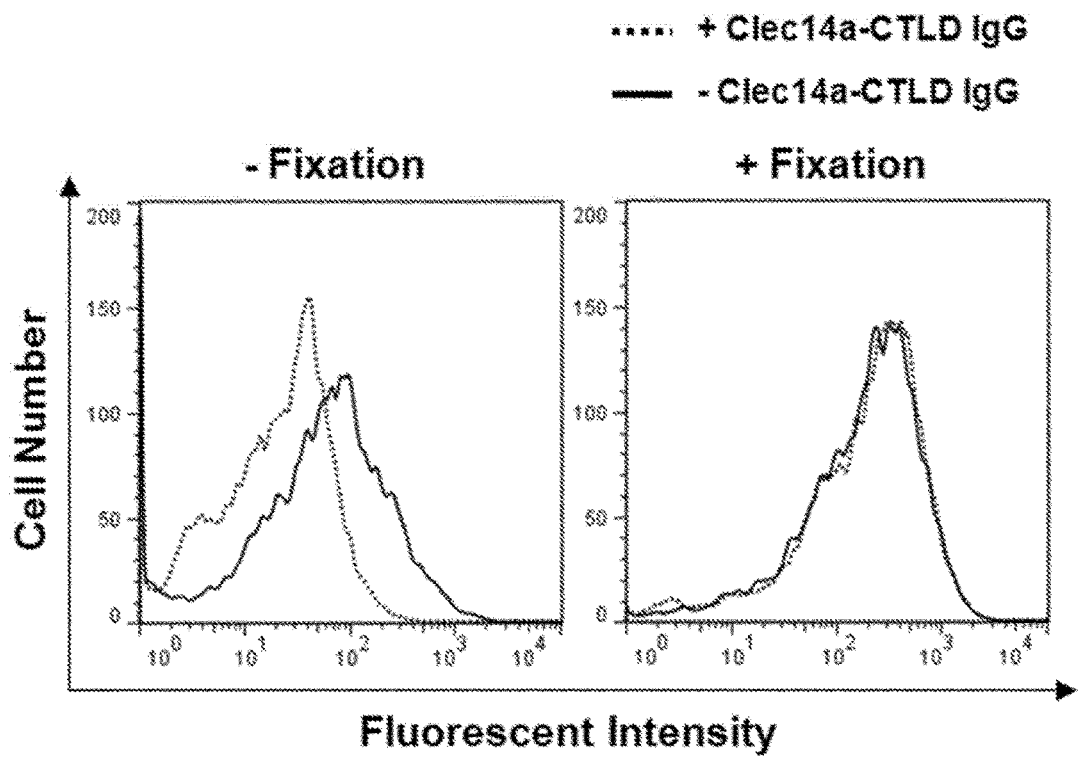
FIG. 9. shows the effect of clec14a-CTLD IgG on the down-regulation of clec14a on the surface of endothelial cells. a. Fixed and unfixed HUVECs were incubated in the presence (dotted line) or absence (solid line) of a clec14a-CTLD IgG (clone 1) and analyzed by flow cytometry. b. Clec14a on the surface of HUVECs incubated with clec14a-CTLD IgG (white) or Fc (black) for the indicated time was assayed by cell ELISA. Values represent mean±SD of triplicate measurements from one of three independent experiments.
Figure 9B:
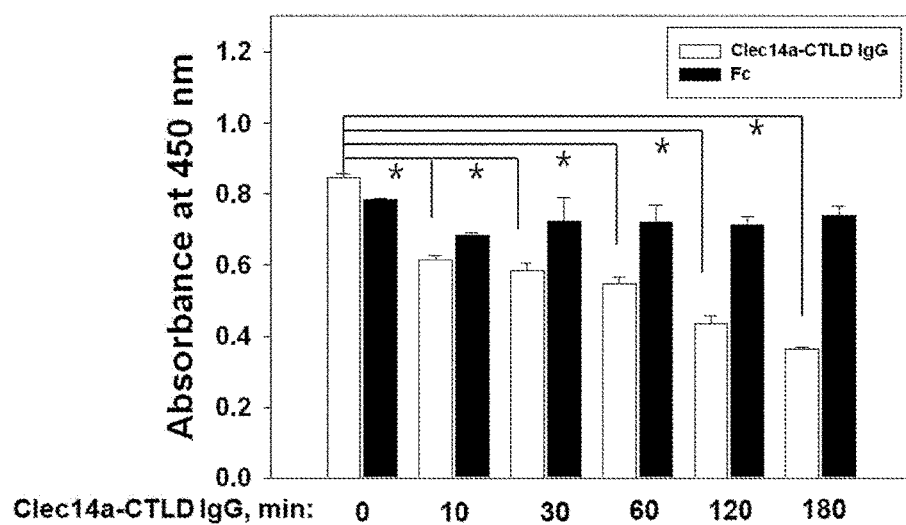

In one embodiment of the present invention, the clec14a-CTLD IgG of the present invention was identified as inhibiting endothelial cell migration (FIGS. 5a and 5b) and tube formation (FIGS. 5c and 5d), and to specifically suppress clec14a-mediated cell-cell contact (FIGS. 7a and 7b), indicating that the antibody can inhibit endothelial cell-cell contact during tumor angiogenesis. In addition, clec14a CTLD-CTLD interaction was blocked by the clec14a-CTLD IgG (FIGS. 8a, 8b and 8c). Moreover, the antibody of the present invention was found to induce the down-regulation of clec14a on the surface of HUVEC (FIGS. 9a and 9b). These results suggest that the antibody of the present invention effectively inhibits clec14a-mediated angiogenesis and thus can be applied to the therapy of angiogenesis-related diseases or cancer.

Preferably, the antibody of the present invention may comprise a heavy-chain variable region comprising heavy-chain CDR1 defined by the amino acid sequence of SEQ ID NO: 14, heavy-chain CDR2 defined by the amino acid sequence of SEQ ID NO: 16, and heavy-chain CDR3 defined by the amino acid sequence of SEQ ID NO: 18, and a light-chain variable region comprising light-chain CDR1 defined by the amino acid sequence of SEQ ID NO: 42, light-chain CDR2 defined by the amino acid sequence of SEQ ID NO: 44, and light-chain CDR3 defined by the amino acid sequence of SEQ ID NO: 46, and more preferably may comprise a heavy-chain variable region having the amino acid sequence of SEQ ID NO: 125 and a light-chain variable region having the amino acid sequence of SEQ ID NO: 129, but is not limited thereto. The nucleic acid encoding the antibody may comprise a heavy-chain nucleic acid sequence comprising heavy-chain CDR1 nucleotide sequence set forth in SEQ ID NO: 70, heavy-chain CDR2 nucleotide sequence set forth in SEQ ID NO: 72, and heavy-chain CDR3 nucleotide sequence set forth in SEQ ID NO: 74, and a light-chain nucleic acid sequence comprising light-chain CDR1 nucleotide sequence set forth in SEQ ID NO: 77, light-chain CDR2 nucleotide sequence set forth in SEQ ID NO: 79, and light-chain CDR3 nucleotide sequence set forth in SEQ ID NO: 81, but is not limited thereto. In one embodiment of the present invention, a human monoclonal antibody comprised of a heavy-chain variable region having the amino acid sequence of SEQ ID NO: 125 and a light-chain variable region having the amino acid sequence of SEQ ID NO: 129 is designated as clone 1. A nucleic acid encoding the antibody may comprise the nucleotide sequence of SEQ ID NO: 133 for the heavy-chain variable region, and the nucleotide sequence of SEQ ID NO: 134 for the light-chain variable region, but is not limited thereto.

In one preferred embodiment, the antibody of the present invention may comprise a heavy-chain variable region comprising heavy-chain CDR1 defined by the amino acid sequence of SEQ ID NO: 21, heavy-chain CDR2 defined by the amino acid sequence of SEQ ID NO: 23, and heavy-chain CDR3 defined by the amino acid sequence of SEQ ID NO: 25, and a light-chain variable region comprising light-chain CDR1 defined by the amino acid sequence of SEQ ID NO: 49, light-chain CDR2 defined by the amino acid sequence of SEQ ID NO: 51, and light-chain CDR3 defined by the amino acid sequence of SEQ ID NO: 53, and more preferably may comprise a heavy-chain variable region having the amino acid sequence of SEQ ID NO: 126 and a light-chain variable region having the amino acid sequence of SEQ ID NO: 130, but is not limited thereto. The nucleic acid encoding the antibody may comprise a heavy-chain nucleic acid sequence comprising heavy-chain CDR1 nucleotide sequence set forth in SEQ ID NO: 84, heavy-chain CDR2 nucleotide sequence set forth in SEQ ID NO: 86, and heavy-chain CDR3 nucleotide sequence set forth in SEQ ID NO: 88, and a light-chain nucleic acid sequence comprising light-chain CDR1 nucleotide sequence set forth in SEQ ID NO: 91, light-chain CDR2 nucleotide sequence set forth in SEQ ID NO: 93, and light-chain CDR3 nucleotide sequence set forth in SEQ ID NO: 95, but is not limited thereto. In one embodiment of the present invention, a human monoclonal antibody comprised of a heavy-chain variable region having the amino acid sequence of SEQ ID NO: 126 and a light-chain variable region having the amino acid sequence of SEQ ID NO: 130 is designated clone 2. A nucleic acid encoding the antibody may comprise the nucleotide sequence of SEQ ID NO: 135 for the heavy-chain variable region, and the nucleotide sequence of SEQ ID NO: 136 for the light-chain variable region, but is not limited thereto.

In another preferred embodiment, the antibody of the present invention may comprise a heavy-chain variable region comprising heavy-chain CDR1 defined by the amino acid sequence of SEQ ID NO: 28, heavy-chain CDR2 defined by the amino acid sequence of SEQ ID NO: 30, and heavy-chain CDR3 defined by the amino acid sequence of SEQ ID NO: 32, and a light-chain variable region comprising light-chain CDR1 defined by the amino acid sequence of SEQ ID NO: 56, light-chain CDR2 defined by the amino acid sequence of SEQ ID NO: 58, and light-chain CDR3 defined by the amino acid sequence of SEQ ID NO: 60, and more preferably may comprise a heavy-chain variable region having the amino acid sequence of SEQ ID NO: 127 and a light-chain variable region having the amino acid sequence of SEQ ID NO: 131, but is not limited thereto. The nucleic acid encoding the antibody comprises a heavy-chain nucleic acid sequence comprising heavy-chain CDR1 nucleotide sequence set forth in SEQ ID NO: 98, heavy-chain CDR2 nucleotide sequence set forth in SEQ ID NO: 100, and heavy-chain CDR3 nucleotide sequence set forth in SEQ ID NO: 102, and a light-chain nucleic acid sequence comprising light-chain CDR1 nucleotide sequence set forth in SEQ ID NO: 105, light-chain CDR2 nucleotide sequence set forth in SEQ ID NO: 107, and light-chain CDR3 nucleotide sequence set forth in SEQ ID NO: 109, but is not limited thereto. In one embodiment of the present invention, a human monoclonal antibody comprised of a heavy-chain variable region having the amino acid sequence of SEQ ID NO: 127 and a light-chain variable region having the amino acid sequence of SEQ ID NO: 131 is designated as clone 3. A nucleic acid encoding the antibody may comprise the nucleotide sequence of SEQ ID NO: 137 for the heavy-chain variable region, and the nucleotide sequence of SEQ ID NO: 138 for the light-chain variable region, but is not limited thereto.

In a further embodiment, the antibody of the present invention may comprise a heavy-chain variable region comprising heavy-chain CDR1 defined by the amino acid sequence of SEQ ID NO: 35, heavy-chain CDR2 defined by the amino acid sequence of SEQ ID NO: 37, and heavy-chain CDR3 defined by the amino acid sequence of SEQ ID NO: 39, and a light-chain variable region comprising light-chain CDR1 defined by the amino acid sequence of SEQ ID NO: 63, light-chain CDR2 defined by the amino acid sequence of SEQ ID NO: 65, and light-chain CDR3 defined by the amino acid sequence of SEQ ID NO: 67, and more preferably may comprise a heavy-chain variable region having the amino acid sequence of SEQ ID NO: 128 and a light-chain variable region having the amino acid sequence of SEQ ID NO: 132, but is not limited thereto. The nucleic acid encoding the antibody comprises a heavy-chain nucleic acid sequence comprising heavy-chain CDR1 nucleotide sequence set forth in SEQ ID NO: 112, heavy-chain CDR2 nucleotide sequence set forth in SEQ ID NO: 114, and heavy-chain CDR3 nucleotide sequence set forth in SEQ ID NO: 116, and a light-chain nucleic acid sequence comprising light-chain CDR1 nucleotide sequence set forth in SEQ ID NO: 119, light-chain CDR2 nucleotide sequence set forth in SEQ ID NO: 121, and light-chain CDR3 nucleotide sequence set forth in SEQ ID NO: 123, but is not limited thereto. In one embodiment of the present invention, a human monoclonal antibody comprised of a heavy-chain variable region having the amino acid sequence of SEQ ID NO: 128 and a light-chain variable region having the amino acid sequence of SEQ ID NO: 132 is designated as clone 4. A nucleic acid encoding the antibody may comprise the nucleotide sequence of SEQ ID NO: 139 for the heavy-chain variable region, and the nucleotide sequence of SEQ ID NO: 140 for the light-chain variable region, but is not limited thereto.

As such, even the antibodies composed of heterogeneous sequences were found to inhibit angiogenesis so long as they specifically recognize clec14a-CTLD. Therefore, they were identified as effectively applicable to the prophylaxis or therapy of angiogenesis-related diseases or cancer.

When the antibody of the present invention comprises a constant domain, it may be derived from IgG, IgA, IgD, IgE, IgM, or combinations or hybrids thereof.

The "combination", as used herein, means that polypeptides encoding single-chain immunoglobulin Fc fragments of the same origin are linked to a single-chain polypeptide of a different origin to form a dimer or multimer. That is, a dimer or multimer may be formed from two or more constant domains selected from the group consisting of constant domains of IgG, IgA, IgD, IgE and IgM.

The term "hybrid", as used herein, means that sequences encoding two or more heavy-chain constant domains of different origins are present in a single-chain immunoglobulin heavy-chain constant domain. For example, domain hybrids may be composed of one to four domains selected from the group consisting of CH1, CH2, CH3 and CH4 of IgG, IgA, IgD, IgE and IgM. Also, a combination or a hybrid may be made from heavy-chain constant domains of the IgG subtypes IgG1, IgG2, IgG3 and IgG4. The combination and the hybrid are as defined above.

In addition, when the antibody of the present invention further comprises a light-chain constant region, it may be derived from the lamda (λ) or kappa (κ) light chain.

Preferably, the antibody may be a human monoclonal antibody that can specifically bind to murine clec14a-CTLD as well as human clec14a-CTLD thereby inhibiting angiogenesis. The ability of the human antibody to function in both humans and mice, that is, the cross-reactivity, provides the advantage of rendering the human antibody applicable to a pre-clinical study in mice.

In accordance with a further aspect thereof, the present invention provides a vector comprising said nucleic acid, and a host cell comprising said vector or said nucleic acid.

In accordance with a further aspect thereof, the present invention provides a method for preparing an antibody specifically binding to clec14a (C-type lectin domain family 14, member A), preferably human clec14a-CTLD (C-type lectin like domain) or human and murine clec14a-CTLD. Preferably, the antibody may be a human monoclonal antibody. The method for preparing the antibody may comprise biopanning using functional domain. Additionally, the present invention provides a method of producing said antibody, comprising culturing said host cell such that the nucleic acid is expressed to produce the antibody.

The monoclonal antibody of the present invention may be easily prepared using a well-known technique. To quote an example, the production of monoclonal antibodies may be achieved by, but is not limited to, a hybridoma constructed with B lymphocytes from immunized animals (Koeher and Milstein, 1976, Nature, 256:495), or a phage display technology.

Preferably, the production of the monoclonal antibody of the present invention may be implemented using a phage display technology. The method of the present invention may be stepwise conducted with reference to, for example, Barbas et al. (METHODS: A Companion to Methods in Enzymology 2: 119, 1991 and J. Virol. 2001 July; 75(14): 6692-9), and Winter et al. (Ann. Rev. Immunol. 12:433, 1994). The phage useful for constructing an antibody library may be filamentous phage which may be exemplified by fd, M13, f1, If1, Ike, Zj/Z, Ff, Xf, Pf1 and Pf3, but is not limited thereto. Examples of the vector that can be used to display exogenous genes on the surface of the filamentous phage include phage vectors such as fUSE5, fAFF1, fdCAT1 and fdtetDOG, or phagemid vectors such as pHEN1, pComb3, pComb8 and pSEX, but are not limited thereto. A helper phage is used to supply a wild-type version of the coat proteins that are required for the successful reinfection of recombinant phage for amplification and may be exemplified by, but is not limited to, M13K07 and VSCM13.

A polynucleotide encoding the hybridoma-derived monoclonal antibody or phage display clone according to the present invention may be readily isolated and sequenced using a typical process. For example, oligonucleotide primers which are designed to specifically amplify heavy- and light-chain coding regions from a hybridoma or phage template DNA may be employed. Once it is isolated, the polynucleotide may be inserted into an expression vector which may be then introduced into a host cell. The resulting host cell (i.e., transformant) thus can produce the monoclonal antibody of interest. Accordingly, the preparation method of the antibody of the present invention may comprise amplifying an expression vector carrying a polynucleotide coding for the antibody. Preferably, a recombinant antibody may be prepared by pre-clearing a Fc binder from a human scFv library and conducting a biopanning technique with a functional domain to select a specific clone.

In accordance with still a further aspect thereof, the present invention provides a polynucleotide coding for the epitope or the antibody, an expression vector carrying the polynucleotide, and a transformant anchoring the vector therein.

The antibody is as described above.

The expression vector carrying the epitope or the antibody according to the present invention may include, but is not limited to, a vector that allows the replication and/or expression of the polynucleotide in eukaryotic or prokaryotic cells such as mammalian cells (e.g., humans, monkeys, rabbits, rats, hamsters, mice, etc.), plant cells, yeasts, insect cells and bacterial cells (e.g., E. coli). Preferably, the vector has a suitable promoter operably linked to the polynucleotide so as to induce the expression of the gene of interest, and at least one selection marker. For example, the polynucleotide may be introduced into a phage, a plasmid, a cosmid, a mini-chromosome, a virus, or a retroviral vector.

The expression vector carrying a polynucleotide coding for the antibody may be a combination of expression vectors carrying polynucleotides coding for the heavy chain of the antibody and the light chain of the antibody, respectively, or an expression vector carrying both the polynucleotides coding for the heavy chain of the antibody and the light chain of the antibody.

Examples of the transformant resulting from the introduction of the expression vector according to the present invention include, but are not limited to, bacterial cells, such as E. coli, streptomyces, Salmonella typhimurium; yeasts; fungi such as Pichia pastoria; insect cells, such as drosophila, spodoptera Sf9; animal cells, such as CHO (Chinese hamster ovary cells), SP2/0 (mouse myeloma), human lymphoblastoid, COS, NSO (mouse myeloma), 293T, melanoma cells, HT-1080, BHK (baby hamster kidney cells), HEK (human embryonic kidney cells), and PERC.6 (human retina cell); and plant cells.

The term "introduction", as used herein, is intended to mean the delivery of the polynucleotide coding for the epitope or the antibody into cells. The introduction can be carried out using various methods well known in the art, including calcium phosphate-DNA co-precipitation, DEAE-dextran-mediated transfection, polybrene-mediated transfection, electroporation, microinjection, liposome fusion, Lipofectamine transfection, and protoplast fusion. Transduction refers to a process whereby foreign DNA is transferred to another cell via a viral vector on the basis of infection. In addition, the delivery of a vector into host cells may be achieved by gene bombardment. In the present invention, introduction may be interchangeably used with transformation.

In accordance with still another aspect thereof, the present invention provides a composition for the suppression of angiogenesis, comprising the antibody.

Since the antibody of the present invention is able to effectively suppress angiogenesis, the composition comprising the antibody as an active ingredient can be useful for suppressing angiogenesis and further for preventing or treating angiogenesis-related diseases.

As used herein, the term "suppression of angiogenesis" means the suppression of the formation or growth of new blood vessels from pre-existing vessels. For the purpose of the present invention, the suppression of angiogenesis is achieved by inhibiting cell migration, cell to cell contacts, more preferably by inhibiting clec14a-mediated cell migration, clec14a-mediated cell-cell contacts, HUVEC migration, or tube formation, clec14a CLTD-CLTD complex formation.

The term "angiogenesis-related disease", as used herein, means a disease that involves angiogenesis in its onset or progression. So long as it can be treated with the antibody, any disease may be within the scope of the angiogenesis-related diseases without limitation. Examples of the angiogenesis-related disease include cancer, metastasis, diabetic retinopathy, retinopathy of prematurity, corneal graft rejection, macular degeneration, neovascular glaucoma, erythrosis, proliferative retinopathy, psoriasis, hemophilic arthritis, capillary formation in atherosclerotic plaques, keloid, wound granulation, vascular adhesion, rheumatoid arthritis, osteoarthritis, autoimmune diseases, Crohn's disease, restenosis, atherosclerosis, intestinal adhesions, cat scratch disease, ulcer, liver cirrhosis, nephritis, diabetic nephropathy, diabetes mellitus, inflammatory diseases, and neurodegenerative diseases, but are not limited thereto. Also, the cancer is selected from the group consisting of esophageal cancer, stomach cancer, large intestine cancer, rectal cancer, oral cancer, pharynx cancer, larynx cancer, lung cancer, colon cancer, breast cancer, uterine cervical cancer, endometrial cancer, ovarian cancer, prostate cancer, testis cancer, bladder cancer, renal cancer, liver cancer, pancreatic cancer, bone cancer, connective tissue cancer, skin cancer, brain cancer, thyroid cancer, leukemia, Hodgkin's lymphoma, lymphoma and multiple myeloid blood cancer, but are not limited thereto.

As used herein, the term "prevention" or "prophylaxis" is intended to refer to any action resulting in the suppression or delay of the onset of diseases of interest thanks to the administration of the antibody or composition according to the present invention. The term "treatment" or "therapy" is intended to refer to any action resulting in an improvement in the symptoms of a disease of interest or the beneficial alteration of the symptoms thanks to the administration of the antibody or composition according to the present invention.

The composition comprising the antibody of the present invention is preferably a pharmaceutical composition and may further comprise a suitable vehicle, excipient or diluent typically used in the art.

The pharmaceutical composition comprising a pharmaceutically acceptable vehicle may be in various oral or non-oral dosage forms, such as tablets, pills, powders, granules, capsules, suspension, internal use solutions, emulsions, syrups, sterile aqueous solutions, non-aqueous solutions, suspensions, lyophilizates, and suppositories. In this regard, the pharmaceutical composition of the present invention may be formulated in combination with a diluent or excipient such as a filler, a thickener, a binder, a wetting agent, a disintegrant, a surfactant, etc. Solid preparations intended for oral administration may be in the form of tablets, pills, powders, granules, capsules, and the like. In regards to these solid agents, the compound of the present invention is formulated in combination with at least one excipient such as starch, calcium carbonate, sucrose, lactose, or gelatin. In addition to a simple excipient, a lubricant such as magnesium stearate, talc, etc. may be used. Among liquid preparations intended for oral administration are suspensions, internal use solutions, emulsion, syrups, and the like. In addition to a simple diluent such as water or liquid paraffin, various excipients, such as wetting agents, sweeteners, aromatics, preservatives, and the like may be contained in the liquid preparations. Also, the pharmaceutical composition of the present invention may be in a parenteral dosage form such as sterile aqueous solutions, non-aqueous solvents, suspensions, emulsions, lyophilizates, suppositories, and the like. Injectable propylene glycol, polyethylene glycol, vegetable oils such as olive oil, and esters such as ethyl oleate may be suitable for the non-aqueous solvents and suspensions. The basic materials of suppositories include Witepsol, macrogol, Tween 61, cacao butter, laurin butter, and glycerogelatin.

The composition of the present invention is administered in a pharmaceutically effective amount.

The term "pharmaceutically effective amount", as used herein, is intended to refer to an amount of a pharmaceutical composition for treating a disease that is sufficient, at a reasonable benefit/risk ratio applicable to any medical treatment. The effective amount may vary depending on various factors including the severity of the disease being treated, the patient's age and sex, the kind of disease, drug activity, sensitivity to the drug, the time of administration, the route of administration, the rate of excretion, the period of time of treatment, the co-administration of drugs, and other parameters well known in the art. The composition of the present invention may be administered alone or in combination with other therapeutics. In this case, the administration may be conducted sequentially or simultaneously together with conventional therapeutics. Also, the composition may be administered in a single dose or may be divided into multiple doses. In full consideration of these factors, it is important to administer a minimal dose sufficient to being about a maximal effect without side effects. The dose can be readily determined by an expert in the art. The dose of the pharmaceutical composition of the present invention is not imparted with special limitations, but varies depending on various factors including patient's health state and weight, the severity of disease, the kind of drug, the route of administration, and the time of administration. The composition may be administered in a single dose or in multiple doses per day into mammals including rats, domestic animals, humans, etc. via any typically accepted route, for example, orally, rectally, intravenously, subcutaneously, intrauterinely, or intracerebrovascularly.

In accordance still another aspect thereof, the present invention provides a method for suppressing angiogenesis, comprising administering the antibody or the composition to a subject in need thereof.

The antibody, the composition and the suppression of angiogenesis are as elucidated above.

In detail, the suppressing method of the present invention comprises administering the pharmaceutical composition at a pharmaceutically effective dose to a subject in need of the suppression of angiogenesis. The subject may be a mammal, such as a dog, cow, horse, rabbit, mouse, rat, chicken, and human, but is not limited thereto. The pharmaceutical composition may be administered parenterally, subcutaneously, intraperitoneally, intrapulmonarily, or intranasally, or by a suitable method including, if necessary, intralesional injection for topical treatment. The preferred dose of the pharmaceutical composition of the present invention varies depending on various factors including in the subject's health state and weight, the severity of the disease, the kind of drug, the route of administration, and the time of administration, and can be readily determined by those skilled in the art.

In accordance with yet still another aspect thereof, the present invention provides a pharmaceutical composition for preventing or treating cancer, comprising the antibody.

The terms "antibody", "preventing", and "treating" are as described above.

So long as it is treatable with the peptide of the present invention, the cancer is not subject to any limitation. Preferred is a cancer in which clec14a-mediated tumor progression takes place. In detail, the onset or progression of cancer is prevented by suppressing angiogenesis with the antibody of the present invention. Examples of the cancer include esophageal cancer, stomach cancer, large intestine cancer, rectal cancer, oral cancer, pharynx cancer, larynx cancer, lung cancer, colon cancer, breast cancer, uterine cervical cancer, endometrial cancer, ovarian cancer, prostate cancer, testis cancer, bladder cancer, renal cancer, liver cancer, pancreatic cancer, bone cancer, connective tissue cancer, skin cancer, brain cancer, thyroid cancer, leukemia, Hodgkin's lymphoma, lymphoma and multiple myeloid blood cancer, but are not limited thereto.

In addition, the antibody of the present invention may be used in combination with other antibodies or biologically active agents or materials for various purposes.

In one embodiment of the present invention, the antibody of the present invention was found to suppress angiogenesis, resulting in the retardation or prevention of the onset or progression of cancer. Hence, the antibody of the present invention is effectively applicable to the prophylaxis or therapy of cancer.

In accordance with yet still a further aspect thereof, the present invention provides a method for treating cancer, comprising administering the antibody or the pharmaceutical composition for preventing or treating cancer to a subject in need thereof.

The antibody, the composition and the cancer are as described above.

In the treatment method, the pharmaceutical composition is administered at a pharmaceutically effective dose to a subject suspected of cancer. The subject may be a mammal, such as a dog, cow, horse, rabbit, mouse, rat, chicken, and human, but is not limited thereto. The pharmaceutical composition may be administered parenterally, subcutaneously, intraperitoneally, intrapulmonarily, or intranasally, or by a suitable method including, if necessary, intralesional injection for topical treatment. The preferred dose of the pharmaceutical composition of the present invention varies depending on various factors including the subject's health state and weight, the severity of the disease, the kind of drug, the route of administration, and the time of administration, and can be readily determined by those skilled in the art.

In accordance with yet still a further aspect thereof, the present invention provides a diagnostic composition for cancer, comprising the antibody.

The antibody and the cancer are as described above.

Preferred is a cancer in which clec14a is expressed specifically.

The term "diagnosis", as used herein, refers to evaluation of the presence or properties of pathological states. With respect to the objects of the present invention, the diagnosis is to determine the incidence of cancer.

In accordance with yet still a further aspect thereof, the present invention provides a diagnostic kit for cancer, comprising the diagnostic composition.

The kit of the present invention can detect the marker for cancer, clec14a, preferably CTLD of clec14a. The detection kit of the present invention may comprise an antibody selectively recognizing the marker, as well as one or more kinds of a composition, a solution, or an apparatus, which are suitable for the analysis method.

Preferably, the diagnostic kit may include a matrix, a suitable buffer solution, a coloring enzyme, or a secondary antibody labeled with a fluorescent substance, a coloring substrate or the like for the immunological detection of antibody. As for the matrix, a nitrocellulose membrane, a 96 well plate made of polyvinyl resin, a 96 well plate made of polystyrene resin, and a slide glass may be used. As for the coloring enzyme, peroxidase and alkaline phosphatase may be used. As for the fluorescent substance, FITC and RITC may be used, and as for the coloring substrate solution, ABTS (2,2'-azino-bis (3-ethylbenzthiazoline-6-sulfonic acid)), OPD (o-phenylenediamine), or TMB (tetramethyl benzidine) may be used.

In accordance with yet still a further aspect thereof, the present invention provides a method for diagnosing cancer, comprising detecting clec14a, preferably clec14a-CTLD through antigen-antibody complexes in a isolated biological sample from a subject with suspected cancer.

The antibody, the cancer, and diagnosis are as described above.

More specifically, the isolation of protein from a biological sample may be achieved using a known process.

The term "biological sample", as used herein includes samples displaying a difference in expression levels of a cancer marker clec14a, preferably clec14a-CTLD, such as tissues, cells, whole blood, serum, plasma, saliva, sputum, cerebrospinal fluid or urine, but is not limited thereto.

With the detection methods, the occurrence of cancer can be diagnosed by comparing the clec14a, preferably clec14a-CTLD, expression level in a patient with suspected cancer to that in a normal control group. That is, the expression level of the marker of the present invention in suspected cancer cell is compared to that in normal cell. If a significant increase in the expression level of the marker is observed in the suspected cancer cell, the suspected cancer can be diagnosed as cancer.

Analysis methods for measuring protein levels include, but are not limited to, Western blotting, ELISA, radioimmunoassay, radialimmunodiffusion, Ouchterlony immunodiffusion, rocket immunoelectrophoresis, immunohistostaining, immunoprecipitation assay, complement fixation assay, FACS, and protein chip assay. With the analysis methods, a patient with suspected cancer is compared with a normal control for the amount of formed antigen-antibody complexes, and the patient's suspected cancer is diagnosed by evaluating a significant increase in expression levels of a protein from the cancer marker gene.

The term "antigen-antibody complexes", as used herein, refers to binding products of a cancer marker protein to an antibody specific thereto. The amount of formed antigen-antibody complexes may be quantitatively determined by measuring the signal intensity of a detection label.

Such a detection label may be selected from the group consisting of enzymes, fluorescent substances, ligands, luminescent substances, microparticles, redox molecules and radioactive isotopes, but the present invention is not limited to the examples. Examples of enzymes available as detection labels include, but are not limited to, β-glucuronidase, β-D-glucosidase, β-D-galactosidase, urase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase. Examples of the fluorescent substances include, but are not limited to, fluorescein, isothiocyanate, rhodamine, phycoerythrin, phycocyanin, allophycocyanin, ophthaldehyde and fluorescamine. Examples of the ligands include, but are not limited to, biotin derivatives. Examples of luminescent substances include, but are not limited to, acridinium esters, luciferin and luciferase. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$. Examples of the radioactive isotopes include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Preferably, the protein expression levels are measured by ELISA. Examples of ELISA include direct ELISA using a labeled antibody recognizing an antigen immobilized on a solid support, indirect ELISA using a labeled antibody recognizing a capture antibody forming complexes with an antigen immobilized on a solid support, direct sandwich ELISA using another labeled antibody recognizing an antigen in an antigen-antibody complex immobilized on a solid support, and indirect sandwich ELISA, in which another labeled antibody recognizing an antigen in an antigen-antibody complex immobilized on a solid support is reacted, and then a secondary labeled antibody recognizing the another labeled antibody is used. More preferably, the protein expression levels are detected by sandwich ELISA, where a sample reacts with an antibody immobilized on a solid support, and the resulting antigen-antibody complexes are detected by adding a labeled antibody specific for the antigen, followed by enzymatic color development, or by adding a secondary labeled antibody specific to the antibody which recognizes the antigen of the antigen-antibody complex, followed by enzymatic development. The incidence of cancer may be diagnosed by measuring the degree of complex formation of a cancer marker protein and an antibody thereto.

Further, the protein expression levels are preferably measured by Western blotting using one or more antibodies to the cancer markers. Total proteins are isolated from a sample, electrophoresed to be separated according to size, transferred onto a nitrocellulose membrane, and reacted with an antibody. The amount of proteins produced by gene expression is determined by measuring the amount of produced antigen-antibody complexes using a labeled antibody, thereby diagnosing the incidence of cancer. The detection methods are composed of methods of assessing expression levels of marker genes in a control and cells in which cancer occurs. mRNA or protein levels may be expressed as an absolute (e.g., μg/ml) or relative (e.g., relative intensity of signals) difference in the amount of marker proteins.

In addition, the protein expression levels are preferably measured by immunohistostaining using one or more antibodies against the cancer markers. Normal epithelial tissues and suspected cancer tissues were collected and fixed, and then paraffin-embedded blocks were prepared according to a widely known method. The blocks were cut into small sections (several μm in thickness), and attached to glass slides to be reacted with one or more selected from the antibodies according to a known method.

Subsequently, the unreacted antibodies were washed, and the reacted antibodies were labeled with an above mentioned detection label selected from the above, and then observed under a microscope.

It is also preferable to analyze the protein level using a protein chip in which one or more antibodies against the cancer marker are arranged and fixed at a high density at predetermined positions on a substrate. In this regard, proteins are separated from a sample and hybridized with a protein chip to form an antigen-antibody complex, which is then read to examine the presence or expression level of the protein of interest, thereby diagnosing the occurrence of cancer.

In accordance with yet still a further aspect thereof, the present invention provides a composition for suppressing angiogenesis, comprising a material for inhibiting the expression of clec14a.

Preferably, the material may be a material for inhibiting the expression of CTLD of clec14a.

In one embodiment of the present invention, the CTLD of clec14a was identified as playing an important role in inhibiting cell migration and tube formation (eg. filopodium formation) (FIGS. 1a, 1b, 2a and 2b). These results suggest that the material for inhibiting the expression of clec14a, preferably clec14a-CTLD, makes to suppress angiogenesis.

The material for inhibiting the expression of clec14a, preferably clec14a-CTLD, includes antisense oligonucleotides, siRNA oligonucleotides, antibodies, aptamers, single chain variable region fragments, peptides, low-molecular-weight compounds, and natural extracts, but is not limited thereto.

Preferably, the material for inhibiting the expression of clec14a, preferably clec14a-CTLD, is antisense oligonucleotides or siRNA oligonucleotides specifically binding to material for inhibiting the expression of clec14a, preferably clec14a-CTLD gene.

As used herein, the term "antisense oligonucleotide" means DNA or RNA or derivatives thereof containing a nucleic acid sequence complementary to a particular mRNA sequence, and binds to the complementary sequence within mRNA to inhibit translation of mRNA into protein. The antisense oligonucleotide sequence may be a DNA or RNA sequence that is complementary to clec14a, preferably clec14a-CTLD mRNA, and is able to bind to clec14a, preferably clec14a-CTLD mRNA, and it is able to inhibit translation, cytoplasmic translocation, or maturation of clec14a, preferably clec14a-CTLD mRNA or all other activities essential for overall biological functions. The antisense oligonucleotide has a length of 6 to 100 bases, preferably 8 to 60 bases, and more preferably 10 to 40 bases.

The antisense oligonucleotide may be modified at one or more positions of the bases, sugars or backbones in order to have improved effectiveness (De Mesmaeker et al., Curr Opin Struct Biol., 5(3):343-55(1995)). The oligonucleotide backbone may be modified, for example, with phosphorothioates, phosphotriesters, methyl phosphonates, short chain alkyl, cycloalkyl, or short chain heteroatomic or heterocyclic intersugar linkages. Also, the antisense oligonucleotide may contain one or more substituted sugar moieties. The antisense oligonucleotide may also contain modified bases. Examples of the modified bases include hypoxanthine, 6-methyladenine, 5-methyl-pyrimidines (especially, 5-methylcytosine), 5-hydroxymethylcytosine (HMC), glycosyl HMC, gentiobiosyl HMC, 2-aminoadenine, 2-thiouracil, 2-thiothymine, 5-bromouracil, 5-hyroxymethyluracil, 8-azaguanine, 7-deazaguanine, N6 (6-aminohexyl) adenine, and 2,6-diaminopurine. In addition, the antisense oligonucleotide of the present invention may be chemically bonded to one or more moieties or conjugates enhancing the activity and cellular uptake of the antisense oligonucleotide. For example, liphophilic moieties include, but are not limited to, a cholesterol moiety, a cholesteryl moiety, cholic acid, a thioether, a thiocholesterol, an aliphatic chain, a phospholipid, a polyamine chain, a polyethylene glycol chain, adamantane acetic acid, a palmityl moiety, an octadecylamine moiety and a hexylamino-carbonyl-oxycholesterol moiety. A method of preparing oligonucleotides including lipid moieties is well known in the art (U.S. Pat. Nos. 5,138,045, 5,218,105 and 5,459,255). The modified oligonucleotide may have enhanced stability in the presence of nucleases and enhanced binding affinity to target mRNA.

The antisense oligonucleotide may be synthesized in vitro by an ordinary method and administered to the body, or may be synthesized in vivo. A method for synthesizing antisense oligonucleotide in vitro employs RNA polymerase I. A method for synthesizing antisense RNA in vivo involves performing transcription of antisense RNA using a vector containing a multicloning site (MCS) in the opposite direction. Such antisense RNA preferably contains a translation stop codon in its sequence to block translation into a peptide sequence.

Design of the antisense oligonucleotide useful in the present invention may be easily performed by the method known in the art with reference to the nucleotides sequence of clec14a, preferably clec14a-CTLD (Weiss, B. (ed.): Antisense Oligodeoxynucleotides and Antisense RNA: Novel Pharmacological and Therapeutic Agents, CRC Press, Boca Raton, Fla., 1997; Weiss, B., et al., Antisense RNA gene therapy for studying and modulating biological processes. Cell. Mol. Life Sci., 55:334-358(1999)).

As used herein, the term "siRNA" refers to a nucleic acid molecule that is able to mediate RNA interference or gene silencing (reference: WO 00/44895, WO 01/36646, WO 99/32619, WO 01/29058, WO 99/07409 and WO 00/44914). Since siRNA can suppress the expression of the target gene, it provides an effective way of gene knockdown or genetic therapy. First discovered in plants, worms, fruit flies and parasites, siRNA has been recently developed and used for studies of mammalian cells.

In the case in which the siRNA molecule is used in the present invention, it may have a structure in which its sense strand (a sequence corresponding to the clec14a, preferably clec14a-CTLD mRNA sequence) and its antisense strand (a sequence complementary to the clec14a, preferably clec14a-CTLD mRNA sequence) form a double strand. Alternatively, it may have a single-stranded structure having self-complementary sense and antisense strands.

The siRNA is not limited to those in which double-stranded RNA moieties constitute complete pairs, but includes the unpaired moieties such as mismatch (corresponding bases are not complementary), bulge (no corresponding base in one chain), etc. The total length of the siRNA may be 10 to 100 bases, preferably 15 to 80 bases, more preferably 20 to 70 bases.

The end of the siRNA may be either blunt or cohesive as long as it is capable of suppressing the expression of the clec14a, preferably clec14a-CTLD gene via RNA interference (RNAi). The cohesive end may be either 3'- or 5'-cohesive end.

In the present invention, the siRNA molecule may have a short nucleotide sequence (e.g., about 5-15 nucleotides) inserted between the self-complementary sense and antisense strands. In this case, the siRNA molecule formed from the expression of the nucleotide sequence forms a hairpin structure via intramolecular hybridization, resulting in a stem-and-loop structure overall. The stem-and-loop structure is processed in vitro or in vivo to give an activated siRNA molecule capable of mediating RNAi.

As used herein, the term "aptamer" refers to a nucleic acid molecule having a binding affinity for a particular target molecule. The aptamer can also inhibit the activity of a particular target molecule by binding to the particular target molecule. The aptamer of the present invention may be an RNA, a DNA, a modified nucleic acid or a mixture thereof. The aptamer of the present invention can also be in a linear or circular form. The aptamer of the present invention is not particularly limited to its length. Typically, it may have a length of approximately 15-200 nucleotides, for example, approximately 100 nucleotides or less, preferably approximately 80 nucleotides or less, more preferably approximately 60 nucleotides or less, and most preferably approximately 45 nucleotides or less. The aptamer of the present invention may also have a length of approximately 18, 20 or 25 nucleotides or more. When the total number of nucleotides is smaller, chemical synthesis and mass-production will be easier, and there is a major advantage in terms of cost. Chemical modification is also easy, stability in the body is high, and toxicity is low.

The aptamer of the present invention can be prepared by utilizing the SELEX method or an improved version thereof (for example, Ellington et al., Nature, 1990 346, 818-822; Tuerk et al., Science, 1990 249, 505-510). The SELEX method is a method of selecting an oligonucleotide specifically binding to the target molecule from an oligonucleotide pool having 10-14 different nucleotide sequences. The oligonucleotide used has a random sequence of about 40 residues, which is flanked by primer sequences. This oligonucleotide pool is allowed to mix with a target molecule, and only the RNA that has bound to the target molecule is collected using a filter or the like. The oligonucleotide collected is amplified by RT-PCR, and this is used as a template for the next round. By repeating this operation about 10 times, an aptamer that binds specifically to the target molecule can be acquired. By increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces or binding modes, and aptamers with the same binding force or binding mode but different base sequences can be obtained in some cases. The SELEX method includes a process of amplification by PCR; by causing a mutation by using manganese ions or the like in the process, it is possible to perform SELEX with higher diversity.

In addition to the known SELEX method, aptamers can be also obtained using the Cell-SELEX method for complex targets, living cells or tissues (Guo et al. Int. J. Mol. Sci., 9(4): 668, 2008), and the Cell-SELEX method has the advantage of direct selection of aptamers against disease without previous knowledge of the target molecule on the surface. Moreover, the Cell-SELEX method is advantageous over the conventional SELEX method in that a functional approach for the target protein in its physiological state is possible during the selection procedure because it may not show its intrinsic properties when isolated.

Meanwhile, an aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target molecule can be substituted. In particular, because the region of the stem structure has already formed base pairs and faces the inside of the double helical structure, nucleic acid bases are unlikely to bind directly to the target molecule. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible. For example, at the 2'-position of ribose, a hydroxy group is substituted by any atom or group. Examples of the atom or group may include hydrogen atom, fluorine atom or —O-alkyl group (e.g., —O—$CH_3$), —O-acyl group (e.g., —O—CHO), and amino group (e.g., —$NH_2$). The aptamer, unless the functional group involved in the direct binding to the target molecule is substituted or deleted, often retains the activity thereof.

In addition, aptamers are easily modifiable because they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

The aptamer of the present invention may be one wherein a sugar residue (e.g., ribose) of each nucleotide has been modified to increase the binding activity, stability, drug deliverability and the like. As examples of the modification in a sugar residue, replacement of the oxygen atom at the 2'-position, 3'-position and/or 4'-position of the sugar residue with another atom, and the like can be mentioned. As the kind of the modification, fluorination, O-alkylation (e.g., O-methylation, O-ethylation), Oarylation, S-alkylation (e.g., S-methylation, S-ethylation), S-arylation, and amination (e.g., —NH) can be mentioned. Such alterations in the sugar residue can be performed by a method known per se (e.g., Sproat et al., Nucle. Acid. Res. 1991 19, 733-738; Cotton et al., Nucl. Acid. Res. 1991 19, 2629-2635; Hobbs et al., Biochemistry 1973 12, 5138-5145).

The aptamer of the present invention may also have a nucleic acid base (e.g., purine or pyrimidine) altered (e.g., by chemical substitution) to increase binding activity. As examples of such alterations, pyrimidine alteration at the 5-position, purine alteration at the 6- and/or 8-position(s), alteration with an extracyclic amine, substitution with 4-thiouridine, and substitution with 5-bromo or 5-iodo-uracil can be mentioned.

The phosphate group contained in the aptamer of the present invention may be altered to confer resistance to nuclease and hydrolysis. For example, the P(O)O group may be substituted with P(O)S (thioate), P(S)S (dithioate), P(O) NR2 (amidate), P(O)R, R(O)OR', CO or $CH_2$ (formacetal) or 3'-amine (—NH—$CH_2$—$CH_2$—) [wherein each unit of R or R' is independently H or a substituted or unsubstituted alkyl (e.g., methyl, ethyl)]. The joining group is, for example, —O—, —N— or —S—, and nucleotides can bind to an adjoining nucleotide via these joining groups.

The alterations may also include alterations such as capping at 3' and 5'. An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agents, toxins, enzymes, radioactive substances, biotin and the like. For such alterations, see, for example, U.S. Pat. Nos. 5,660,985 and 5,756,703.

In addition, aptamers are attached to the surface of liposomes or nanoparticles to deliver an anticancer agent, a toxin, a tumor suppressor gene, and a siRNA (small interfering RNA) encapsulated in the liposomes or nanoparticles to the target cell.

In the present invention, the material for inhibiting the expression of clec14a, preferably clec14a-CTLD, in particular, its activity is preferably an antibody, a peptide, a low-molecular-weight compound, or a natural extract that specifically binds to clec14a, preferably clec14a-CTLD.

The antibody which can specifically bind to clec14a, preferably clec14a-CTLD, is as elucidated above.

The peptide that specifically binds to clec14a, preferably clec14a-CTLD to inhibit its activity may be obtained by the typical method known in the art, for example, by phage display (Smith G P, "Filamentous fusion phage: novel expression vectors that display cloned antigens on the virion surface". Science 228 (4705):1315-1317(1985); Smith G P, Petrenko V A, "Phage display". Chem. Rev. 97(2):391-410 (1997)).

Preferably, the composition for suppressing angiogenesis may treat cancer by suppressing angiogenesis.

Preferably, the composition for suppressing angiogenesis may treat angiogenesis-related disease by suppressing angiogenesis.

In accordance with yet still a further aspect thereof, the present invention provides a kit for suppressing angiogenesis, comprising the composition, and wherein the composition comprises material for inhibiting the expression of clec14a, preferably clec14a-CTLD.

In accordance with yet still a further aspect thereof, the present invention provides a method for suppressing angiogenesis, comprising administering the composition to a subject in need thereof, and wherein the composition comprises material for inhibiting the expression of clec14a, preferably clec14a-CTLD. In accordance with yet still a further aspect thereof, the present invention provides a method for treating cancer, comprising administering the composition to a subject in need thereof, and wherein the composition comprises material for inhibiting the expression of clec14a, preferably clec14a-CTLD.

In accordance with yet still a further aspect thereof, the present invention provides an antibody-drug conjugate comprising said antibody of any one among claims 1 to 17 attached to a drug. The drug may be any one selected from the group consisting of a toxin, a chemotherapeutic agent, an anticancer drug, an antibiotic, ADP-ribosyl transferase, a radioactive isotope and a nucleolytic enzyme, but are not limited thereto.

Preferably, the antibody-drug conjugate may be capable of being internalized into a cell. More preferably, the cell may be a cancer cell. In one embodiment of the present invention, clec14a-CTLD IgG can be internalized into a cell expressing clec14a such as a cancer cell (FIG. 9a, 9b).

In accordance with yet still a further aspect thereof, the present invention provides a pharmaceutical composition for preventing or treating angiogenesis-related disease, comprising fusion protein of CTLD of clec14a and Fc.

Figure 11:
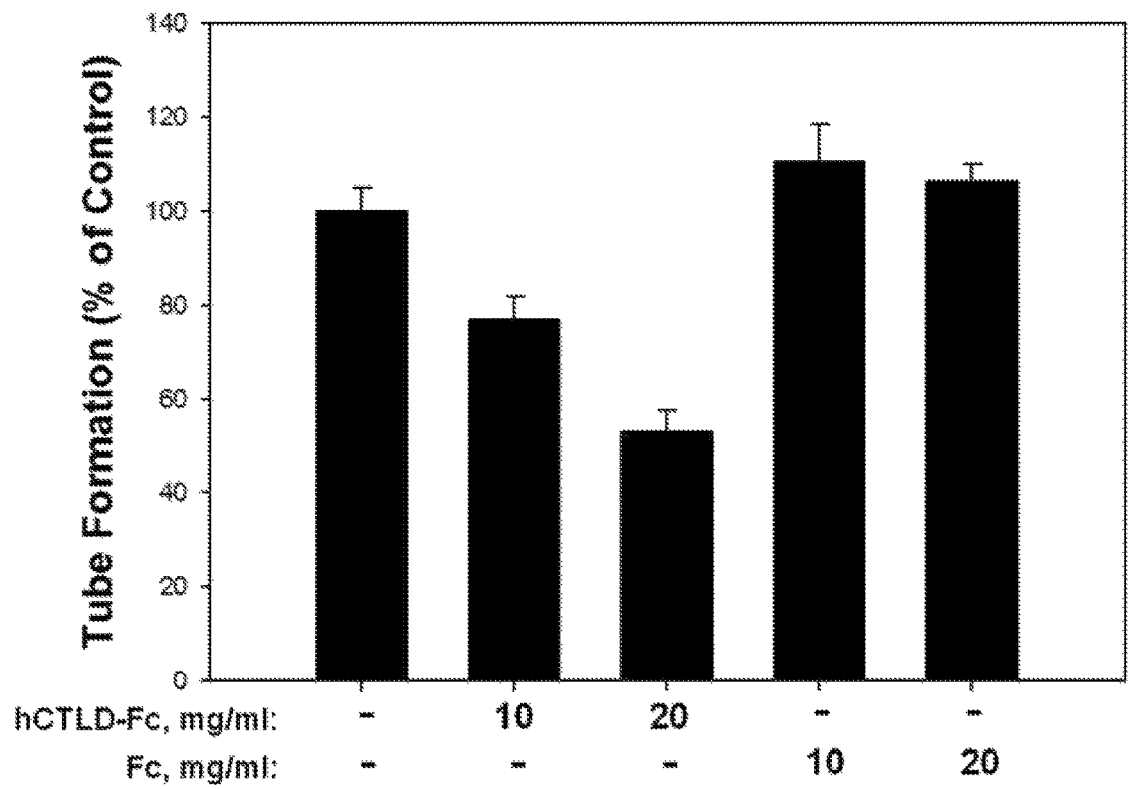
FIG. 11. is a graph showing the inhibitory effect of hCTLD-Fc on tube formation.

In one embodiment of the present invention, hCTLD-Fc inhibited tube formation in a concentration-dependent manner (FIG. 11).

MODE FOR THE INVENTION

Hereinafter, the present invention will be described in further detail with reference to examples. It will be obvious to a person having ordinary skill in the art that these examples are illustrative purposes only and are not to be construed to limit the scope of the present invention.

Example 1: Cell Culture and Transfection

Human umbilical vein endothelial cells (HUVECs, Lonza, Baltimore, Md., USA) were maintained in endothelial growth medium-2 (EGM-2). Mouse aortic endothelial cells (MAECs) and COS-7 cells were grown in Dulbecco's modified Eagle medium containing 10% (v/v) fetal bovine serum and 1% (v/v) penicillin/streptomycin. Cells were maintained in a humidified, $CO_2$-controlled incubator (Sanyo, Panasonic Healthcare Company, Secaucus, N.J., USA) at 37° C. and 5% $CO_2$. HEK293F cells were maintained in Freestyle™ 293 expression media (Invitrogen) supplemented with 1% (v/v) penicillin/streptomycin in a humidified Multitron incubation shaker (Infors HT, Bottmingen (Switzerland) at 37° C. and 8% $CO_2$. HUVECs and COS-7 cells were transfected with vectors encoding GFP, clec14a-GFP (wild-type clec14a), or clec14aΔCTLD-GFP (clec14a CTLD deletion mutant) using Lipofectamine 2000 (Invitrogen, Carlsbad, Calif., USA) according to the manufacturer's instruction.

Example 2: Construction and Preparation of Human and Mouse CTLD Fc Fusion Proteins DNA encoding amino acid residues 31-172 of hCTLD was amplified using the primers 5'-TCGCGCGGCCGCT-GCTCGGCCTCGGGGGCCTGC-3' (SEQ ID NO:1) and 5'-TCGCCTCGAGCTTGCACAGGTAGCCGTTGG-3' (SEQ ID NO:2). DNA encoding the same residues of mCTLD was amplified using the primers 5'-TCGCGGC-CCAGGCGGCCTGTTCGGCCTCGGGGGCTTG-3' (SEQ ID NO:3) and 5'-TCGCGGCCGGCCTGGCCCTTG-CATAGGTAGCCATCGG-3' (SEQ ID NO:4). PCR fragments were digested with SfiI (NEB, Ipswich, Mass., USA) and cloned into the modified mammalian expression vector pCEP4 (Invitrogen) encoding the hinge and CH2-CH3 domain of human IgG1 in the 3' region of the cloning site (gift of Dr. Chung, Seoul National University, Seoul, South Korea). Ligated products were transformed into competent *Escherichia coli* DH5a cells and plasmid DNA was prepared. HEK293F cells ($6 \times 10^8$ cells) were transfected with 0.75 mg each DNA using 1.5 mg polyethylenimine (Polysciences, Inc., Warrington, Pa., USA). The transfected cells were maintained in Freestyle™ 293 expression media supplemented with 1% (v/v) penicillin/streptomycin. After 7 days in culture, culture medium was collected and fusion proteins were purified by affinity chromatography on protein A Sepharose (RepliGen, Waltham, Mass., USA). Protein concentration was quantified using a NanoDrop spectrophotometer (Wilmington, Del., USA). Samples were dialyzed against PBS and analyzed by SDS-PAGE and Coomassie brilliant blue staining. Aliquots of the final pooled fraction were stored at −80° C.

Example 3: Pre-Clearing of Human Synthetic scFv Library

A human synthetic scFv library was re-amplified (Barbas C F. Phage display: a laboratory manual. Cold Spring Harbor, N.Y.: Cold Spring Harbor Laboratory Press; 2001). To pre-clear Fc binders, human immunoglobulin-G (Green Cross Pharma Derivatives Corp, Yong-in, Korea) was immobilized on protein A Sepharose and the antibody-protein A complexes were incubated with the library at 37° C. for 2 hr. Following brief centrifugation, the supernatant was collected and the pellet was discarded. This procedure was repeated two times. The final supernatant was analyzed by phage ELISA to assess the extent of clearing.

Example 4: Selection of CTLD-Specific scFvs Using Phage Display

Three rounds of biopanning were carried out with immunotubes (Immuno™ tube maxisorp, Nunc, Rochester, N.Y., USA) or magnetic beads (Dynabeads M-270 epoxy, Invitrogen) coated with 4 μg recombinant human (hCTLD-Fc) or mouse (mCTLD-Fc) fusion protein to select clones with cross-species reactivity, as described previously (Barbas C F. Phage display: a laboratory manual. Cold Spring Harbor, N.Y.: Cold Spring Harbor Laboratory Press; 2001; Vestweber D. Lymphocyte trafficking through blood and lymphatic vessels: more than just selectins, chemokines and integrins. European Journal of Immunology. 2003; 33(5):1361-4). Ninety-six phage clones were randomly selected from colonies grown on output plates and tested for reactivity to human and mouse CTLDs by phage enzyme immunoassay. DNA of the final scFv clones was sequenced and classified as four scFv clones identified having different complementarity determining region sequences.

Example 5: Preparation of Clec14a-CTLD IgG

The variable heavy chain (VH) gene of selected scFv clones (clones 1-4) was amplified using the primers 5'-CGGGAATTCGCCGCCACCATGGAATG-GAGCTGGGTCTTTCTCTTCTTCCT GCTGTCAG-TAACTACAGGTGTCCTCTCCGAGGTGCAGCTGTTG-GAGTCTG-3' (SEQ ID NO: 5) and 5'-GGCGGGCCCTTGGTGGAGGCTGAGCTCACGGT-GACCAGTGCCCTTGGCC CC-3'(SEQ ID NO: 6). The variable light chain (VL) gene of the clones was amplified using the primers 5'-CCCAAGCTTGCCGCCACCATGGA-GACACATTCTCAGGTCTTTGTATACAT GTTGCT-GTGGTTGTCTGGTGTTGAAGGACCAGTCTGTGCT-GACTCAGCC-3'(S EQ ID NO: 7) and 5'-GGCCGTA CGTAGGACCGTCAGCTTGGTGCCTCCGCCTAAGA-CATAACCACC-3' (SEQ ID NO: 8). $V_H$ primers were designed to add EcoRI and ApaI restriction sites to both the 5' and 3' ends. VL primers were designed to add HindIII and BsiWI sites to both ends. PCR fragments were digested with the appropriate restriction enzymes (NEB, Ipswich, Mass., USA) and cloned into the bicistronic mammalian expression vector pCDNA3.1 (Invitrogen) encoding the hinge and CH2-CH3 domain of human IgG1 3' of the $V_H$ cloning site, (gift of Dr. Hong, Kangwon National University, Chuncheon, Kangwon, South Korea) (Sambrook J, Russell D W. Molecular cloning: a laboratory manual. 3rd ed. Cold Spring Harbor, N.Y.: Cold Spring Harbor Laboratory Press; 2001). Clec14a-CTLD IgG was produced and purified as described previously (Kim H Y, Tsai S, Lo S C, Wear D J, Izadjoo M J. Production and characterization of chimeric monoclonal antibodies against *Burkholderia pseudomallei* and *B. mallei* using the DHFR expression system. PLoS ONE [Electronic Resource]. 6(5):e19867).

Example 6: Wound Healing and Cell Migration Assay

A CytoSelect™ 24-well wound healing assay kit (Cell Biolabs Inc, San Diego, Calif., USA) was used according to the manufacturer's instructions. Briefly, COS-7 cells transfected with GFP, clec14a-GFP, or clec14aΔCTLD-GFP were added to each well by carefully inserting the pipette tip through the open end at the top of the wound healing insert. When cells had grown to confluence, inserts were removed from the wells, and cells were washed twice with phosphate-buffered saline (PBS). Images were captured 20 hr after wounding.

To analyze endothelial cell migration, HUVECs were cultured in the insert until monolayer formation and incubated in the absence or presence of 20 μg/ml clec14a-CTLD IgG or cetuximab for 9 hr at 37° C. Cells were washed twice with PBS and stained with crystal violet (Sigma, St. Louis, Mo., USA). For quantitative analysis, five fields per plate were photographed under a light microscope (Nikon TS 100, Melville, N.Y., USA), and distance migrated was measured manually.

Example 7: Immunocytochemistry

Immunocytochemistry was performed as described previously (Lee S, et al., Hydrogen peroxide increases human leukocyte adhesion to porcine aortic endothelial cells via NFkappaB-dependent up-regulation of VCAM-1. Int Immunol. 2007 December; 19(12):1349-5926). Briefly, COS-7 cells and HUVECs transfected with GFP, clec14a-GFP, or clec14aΔCTLD-GFP grown on collagen-coated coverslips for 1 day were fixed with 4% (w/v) paraformaldehyde for 30 min at 37° C. Cells were washed twice with PBS and blocked by incubation in PBS containing 5% (w/v) bovine serum albumin (BSA) and 0.1% TX-100 for 1 hr at 37° C. Cells were incubated with 0.1 unit/well rhodamine phalloidin and 2 μg/ml Hoechst for 1 hr and viewed under a fluorescence microscope (Leica DM2500, Wetzlar, Germany).

Example 8: ELISA 25 nM recombinant hCTLD-Fc, mCTLD-Fc, or Fc fragment of IgG1 in PBS was added to the 96-wells of a microtiter plate. After incubation overnight at 37° C., plates were washed three times with PBS containing 0.05% (v/v) Tween 20 (PBST), and incubated with 3% (w/v) BSA in PBST for 1 hr at 37° C. Plates were then incubated with 67 nM clec14a-CTLD IgG in PBST containing 3% (w/v) BSA for 3 hr at 37° C. Plates were washed twice with PBST and incubated with horseradish peroxide (HRP)-conjugated anti-human lambda light chain antibody (Bethyl Laboratories, Montgomery, Tex., USA) diluted 1:1000) in PBST containing 3% (w/v) BSA, for 1 hr at 37° C.

To measure CTLD-CTLD interaction, lysates (20 μg) of COS-7 cells transfected with GFP, clec14a-GFP, or clec14aΔCTLD-GFP were added to wells of 96-well plates and incubated with 3% (w/v) BSA in PBST for 1 hr at 37° C., followed by addition of 0.15 μg of hCTLD-Fc or Fc in the same buffer and incubated for 2 hr at 37° C. To assay competition with clec14a-CTLD IgG, hCTLD-Fc was pre-incubated with increasing concentrations of clec14a-CTLD IgG in PBST containing 3% (w/v) BSA for 2 hr at 37° C. The protein complexes were then added to wells and incubated for 2 hr at 37° C. Wells were washed three times in PBST, and HRP-conjugated donkey anti-human Fc IgG (1:5000; Jackson Immunoresearch Laboratories, Inc., West Grove, Pa., USA) was added and incubated for 1 hr at 37° C. Wells were washed three times in PBST and 100 µl TMB substrate solution (BD Biosciences, San Jose, Calif., USA) were added to each well. Optical density was measured at 450 nm using a microtiter plate reader (VICTOR™ X4, Perkin Elmer, Waltham, Mass., USA).

Example 9: Flow Cytometry

HUVECs ($3 \times 10^5$) grown in 6-well microtiter plates were incubated in the absence or presence of 20 ng/ml hTNFα (Millipore, Billerica, Mass., USA) or 20 µg/ml clec14a-CTLD IgG or cetuximab for 24 hr. Cells were harvested and stained with 20 µg/ml anti-VCAM-1 or ICAM-1 polyclonal antibody in flow cytometry buffer for 1 hr at 37° C. Cells were washed three times with flow cytometry buffer, centrifuged at 1000×g for 10 min, and incubated for 1 hr at 37° C. with Alexa Fluor 488-labeled antirabbit antibody (1:1000; Jackson ImmunoResearch) in flow cytometry buffer.

HUVECs ($3 \times 10^5$) grown in 6-well microtiter plates were fixed with 4% (w/v) paraformaldehyde. Fixed and unfixed cells were washed twice with PBS and incubated in the absence or presence of 20 µg/ml clec14a-CTLD IgG for 2 hr at 37° C. Cells were stained with 7.5 µg/ml sheep anti-clec14a polyclonal antibody for 2 hr at 37° C. Cells were washed three times with flow cytometry buffer, incubated with Northern Lights™ 493 Fluorochrome (NL493)-labeled anti-sheep antibody (1:200; R&D Systems, Minneapolis, Minn., USA) in flow cytometry buffer, and analyzed by flow cytometry (BD FACSCalibur, BD Bioscience, Miami, Fla., USA).

Example 10: Tube Formation

Tube formation assays were performed as described previously (Rho S S, et al., Clec14a is specifically expressed in endothelial cells and mediates cell to cell adhesion. Biochemical & Biophysical Research Communications. 404(1): 103-8). Briefly, 250 µl Matrigel (BD Biosciences, Bedford, Mass.) was added to wells of a 24-well plate and allowed to polymerize for 20 min at 37° C. HUVECs cultured in EGM-2 were harvested, resuspended in EGM-2, and seeded onto the Matrigel ($1 \times 10^5$ cells/well). Cultures were incubated in the absence or presence of clec14a-CTLD IgGs or cetuximab at 37° C. and photographed at 21 hr. Tubes were counted manually.

Example 11: HUVEC Cell Viability Assay

HUVECs ($10^4$) were seeded in 96-well microtiter plates and incubated with 20 µg/ml clec14a-CTLD IgGs, cetuximab, or 5-FU (Sigma) for 2 days at 37° C. Cell viability was measured using Cell Counting Kit-8 (Dojindo, Kumamoto, Japan) according to the manufacturer's instructions. Absorbance was measured at 450 nm with a VICTOR™ X4 spectrophotometer (Perkin Elmer).

Example 12: Measurement of Cell-Cell Contact

Cell-cell contact assays were performed as described previously (Rho S S, et al., Clec14a is specifically expressed in endothelial cells and mediates cell to cell adhesion. Biochemical & Biophysical Research Communications. 404 (1):103-8). Briefly, $1.5 \times 10^7$ HEK293F cells in suspension were transfected with plasmids expressing GFP, Clec14a-GFP, and Clec14aΔCTLD-GFP, cultured in Freestyle™ 293 expression medium overnight, and seeded in 6-well plates ($5 \times 10^5$ cells/well). Cells were maintained in the absence or presence of 20 µg/ml clec14a-CTLD IgG or cetuximab for 8 hr. Cell aggregates (mass>4 cells) were counted in at least 10 fields and mean±standard deviation (SD) were determined.

Example 13: Immunoblot Analysis

Immunoblot analysis were performed as described previously (Van Meter K E, et al., A monoclonal antibody that inhibits translation in Sf21 cell lysates is specific for glyceraldehyde-3-phosphate dehydrogenase. Archives of Insect Biochemistry & Physiology. 2008; 69(3):107-17). Briefly, lysates (20 µg) of COS-7 cells transfected with GFP-, clec14a-GFP-, or clec14aΔCTLD-GFP were separated by electrophoresis in a 12% polyacrylamide gel. Proteins were transferred to nitrocellulose membranes using a wet transfer system (GE Healthcare Life Sciences, Pittsburgh, Pa., USA). Membranes incubated in 10 mM Tris/HCl, pH 7.5, 150 mM NaCl, and 0.05 (v/v) % Tween 20 (TTBS), containing 5% (w/v) skim milk at room temperature for 1 hr, followed by incubation with anti-GFP monoclonal antibody (1:5000; Santa Cruz Biotechnology, Santa Cruz, Calif., USA) or anti-β-actin monoclonal antibody (1:5000; Applied Biological Materials, Richmond, BC, Canada) in the same solution overnight at 4° C. The membrane was washed with TTBS and incubated with HRP-conjugated Affinipure goat anti-mouse IgG (1:5000; Jackson ImmunoResearch, West Grove, Pa., USA) in TTBS containing 5% (w/v) skim milk at room temperature for 1 hr. Following several washes with TTBS, protein bands were visualized using SuperSignal West Pico Chemiluminescent Substrate (Pierce, Rockford, Ill., USA) according to the manufacturer's instructions.

Example 14: Cell ELISA

HUVECs ($10^4$) plated on 96-well plates were incubated with 20 µg/ml clec14a-CTLD IgG or Fc for 0, 10, 30, 60, 120, or 180 min at 37° C. Cells were washed twice with ice-cold PBS, blocked in 3% (w/v) BSA in PBS for 1 hr at 4° C., and incubated with sheep anti-clec14a polyclonal antibody (1:1000) in the blocking solution for 2 hr at 4° C. Cells were washed three times with ice-cold PBS and incubated with HRP-conjugated anti-sheep IgG (1:5000; Santa Cruz Biotechnology) for 1 hr at 4° C. After several washes with PBS, 100 µl TMB substrate solution was added to each well. Optical density was measured at 450 nm using a microtiter plate reader.

Example 15: ELISA for Epitope Mapping

Each of 10 µg/ml hCTLD-Fc, Fc, or N-terminal or C-terminal fragments of hCTLD-Fc in PBS was added to 96-well plates. Plates were incubated overnight at 37° C., washed three times with PBS containing 0.05% (v/v) Tween 20 (PBST), and incubated with 3% (w/v) BSA in PBST for 1 hr at 37° C. Plates were incubated with 10 µg/ml clec14a-CTLD IgG in PBST containing 3% (w/v) BSA for 2 hr at 37° C. Following two times washings with PBST, horseradish peroxide (HRP)-conjugated anti-human lambda light chain antibody (1:1000; Bethyl Laboratories, TX, USA) in PBST containing 3% (w/v) BSA was incubated for 1 hr at 37° C.

Example 16: Tube Formation Assay in the Absense or Presense of hCTLD-Fc

250 µl of Matrigel (BD Biosciences) was added to 24-well plates and allowed to polymerize for 20 min at 37° C. HUVECs cultured in EGM-2 were harvested, resuspended in EGM-2, and seeded onto the Matrigel (1×10$^5$ cells/well). Cultures were incubated in the absence or presence of 10 and 25 µg/ml hCTLD Fc or Fc at 37° C. and photographed at 8 hr.

Figure 1A:
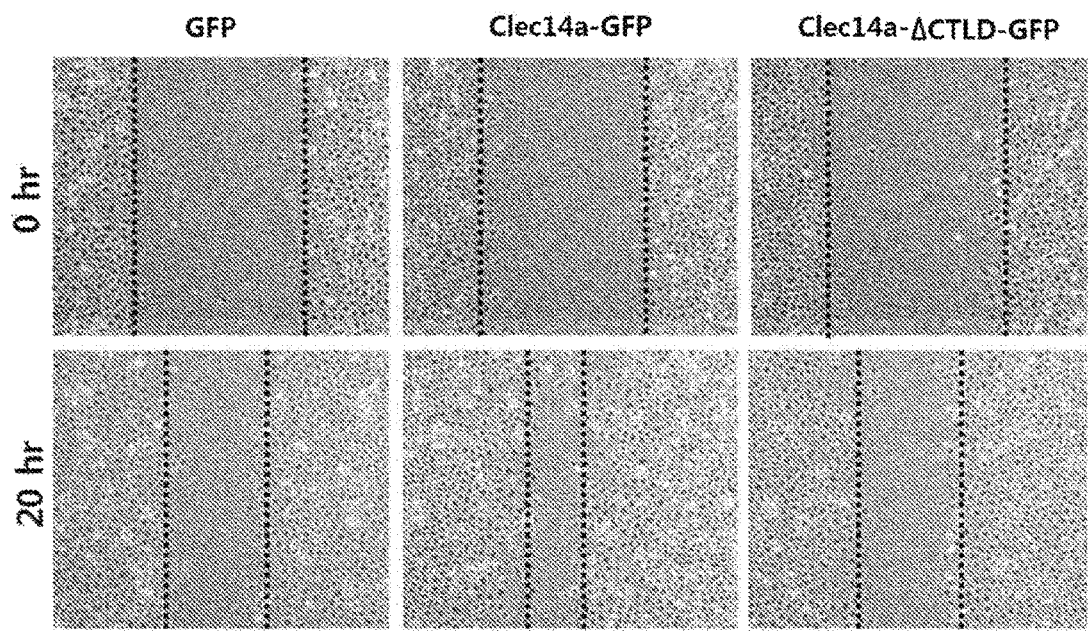
FIG. 1. shows the effect of clec14a CTLD in cell migration. a. Migration of COS-7 cells transfected with GFP, clec14a-GFP, or clec14aΔCTLD-GFP in the wound healing assay was monitored under a light microscope. Images were captured at 0 hr (top) and 20 hr (bottom). b. Distance migrated is expressed as percent of control migration. Values represent mean±SD of triplicate measurements from one of three independent experiments.
Figure 1B:
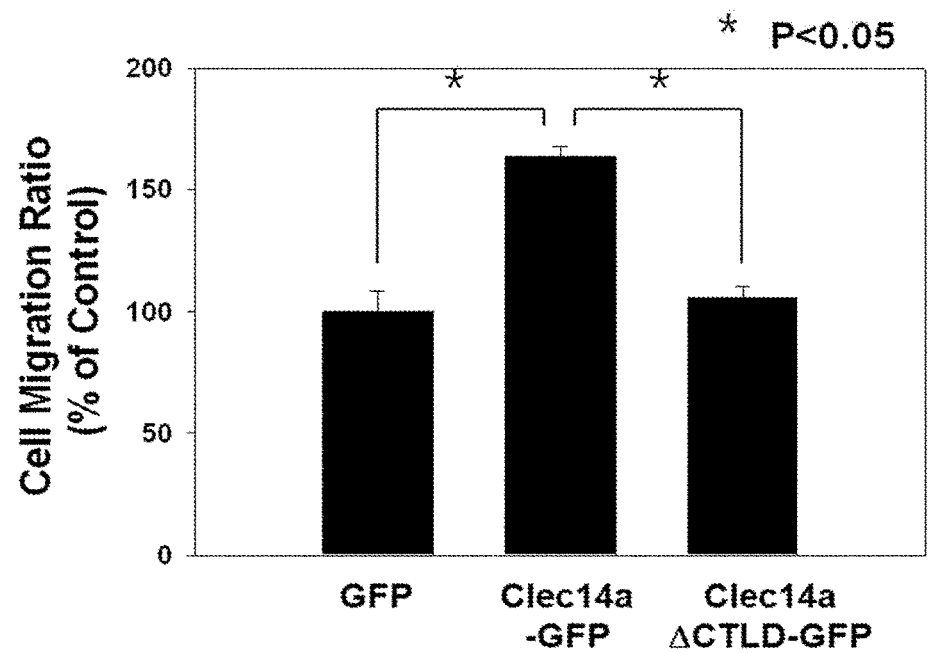

Experimental Example 1: Clec14a CTLD May Play a Key Role in Cell Migration and Filopodium Formation To elucidate the role of CTLD in clec14a-mediated cell migration, COS-7 cells were transfected with green fluorescent protein (GFP), wild-type clec14a fused to GFP (clec14a-GFP), or a clec14a CTLD deletion mutant fused to GFP (clec14aΔCTLD-GFP), and assayed migration in a wound healing assay at 0 and 20 hr. The extent of migration of cells expressing wild-type clec14a was approximately 1.6-fold greater than that of cells expressing GFP alone, whereas expression of the clec14aΔCTLD deletion mutant had little effect on migration (FIGS. 1a and 1b).

Because cell migration is specifically regulated by actin cytoskeletal rearrangement, immunocytochemistry was used to investigate actin network organization in COS-7 cells and human umbilical vein endothelial cells (HUVECs) expressing GFP, clec14a-GFP, or clec14aΔCTLD-GFP. In both cell types, clec14a-GFP overexpression dramatically increased filopodium formation, whereas GFP or clec14aΔCTLD-GFP had minimal effect (FIGS. 2a and 2b).

Together, these results suggest that CTLD may play a crucial role in endothelial cell migration by regulating actin cytoskeletal rearrangements.

Experimental Example 2: Isolation of CTLD-Specific Single-Chain Variable Fragments (scFvs)

Because CTLD of human, mouse or chimpanzee clec14a (Table 1) were Fc fusion proteins, two sequential pre-clearing steps were performed for removing Fc binders from a human synthetic scFv library; removal of approximately 90% was confirmed by phage enzyme-linked immunosorbent assay.

TABLE 1

| Amino acid sequences of clec14a-CTLDs | | |
|---|---|---|
| Human clec14a-lectin (a.a 31-172) | CSASGACYSLHHATMKRQAAEEACILRGGA LSTVRAGAELRAVLALLRAGPGPGGGSKDL LFWVALERRRSHCTLENEPLRGFSWLSSDPG GLESDTLQWVEEPQRSCTARRCAVLQATGG VEPAGWKEMRCHLRANGYLCK | SEQ ID NO: 9 |
| Mouse clec14a-lectin (a.a 31-172) | CSASGACYSLHHATFKRRAAEEACSLRGGT LSTVHSGSEFQAVLLLLRAGPGPGGGSKDLL FWVALERSISQCTQEKEPLRGFSWLHPDSED SEDSPLPWVEEPQRSCTVRKCAALQATRGV EPAGWKEMRCHLRTDGYLCK | SEQ ID NO: 10 |
| Chimpanzee clec14a-lectin (a.a 31-172) | CSASGACYSLHHATMKRQAAEEACILRGGA LSTVRAGAELRAVLALLRAGPGPGGGSKDL LFWVALERRRSHCTLENEPLRGFSWLSSDPG GLESDTLQWVEEPQRSCTARRCAVLQATGG VEPAGWKEMRCHLRANGYLCK | SEQ ID NO: 141 |

TABLE 1-continued

| Nucleotide sequences of clec14a-CTLDs | | |
|---|---|---|
| Human clec14a-lectin (nt 91-516) | tgctcggcctcggggcctgctacagcctgc accacgctaccatgaagcggcaggcggccga ggaggcctgcatcctgcgaggtgggcgctc agcaccgtgcgtgcgggcgccgagctgcgcg ctgtgctcgcgctcctgcgggcaggcccagg gcccggaggggctccaaagacctgctgttc tgggtcgcactggagcgcaggcgttcccact gcaccctggagaacgagcctttgcgggttt ctcctggctgtcctccgaccccggcggtctc gaaagcgacacgctgcagtgggtggaggagc cccaacgctcctgcaccgcgcggagatgcgc ggtactccaggccaccggtggggtcgagccc gcaggctggaaggagatgcgatgccacctgc gcgccaacggctacctgtgcaag | SEQ ID NO: 11 |
| Mouse clec14a-lectin (nt 91-516) | tgttcggcctcggggcttgctacagccttc accacgctaccttcaagagaagggcggcgga ggaggcctgcagcctaaggggcgggactctc agcaccgtgcactcaggctcggagtttcaag ctgtgctcctgctcttgcgtgcaggtcccgg gcctggcggaggctccaaagatcttctgttc tgggtggctctggaacgcagcatctcacagt gcactcaggagaaagagcctttaagggggttt ctcctggttgcacccggactcagaagactca gaggacagcccactaccgtgggtggaagagc cacaacgttcctgtacagtgagaaagtgcgc tgcgctccaggccaccaggggagtggagcct gctggttggaaggagatgcgctgtcatctgc gcaccgatggctacctatgcaag | SEQ ID NO: 12 |
| Chimpanzee clec14a-lectin (nt 91-516) | tgctcggcctcggggcctgctacagcctgc accacgctaccatgaagcggcaggcggccga ggaggcctgcatcctgcgaggtgggcgctc agcaccgtgcgtgcgggcgccgagctgcgcg ctgtgctcgcgctcctgcgggcaggcccagg gcccggaggggctccaaagacctgctgttc tgggtcgcactggagcgcaggcgttcccact gcaccctggagaacgagcctttgcgggttt ctcctggctgtcctccgaccccggcggtctc gaaagcgacacgctgcagtgggtggaggagc cccaacgctcctgcaccgcgcggagatgcgc ggtactccaggccaccggtggggtcgagccc gcaggctggaaggagatgcgatgccacctgc gcgccaacggctacctgtgcaag | SEQ ID NO: 142 |

Amino acid residues on the amino acid sequences used in the present invention are expressed by abbreviations according to the IUPAC-IUB nomenclature.

Figure 3B:
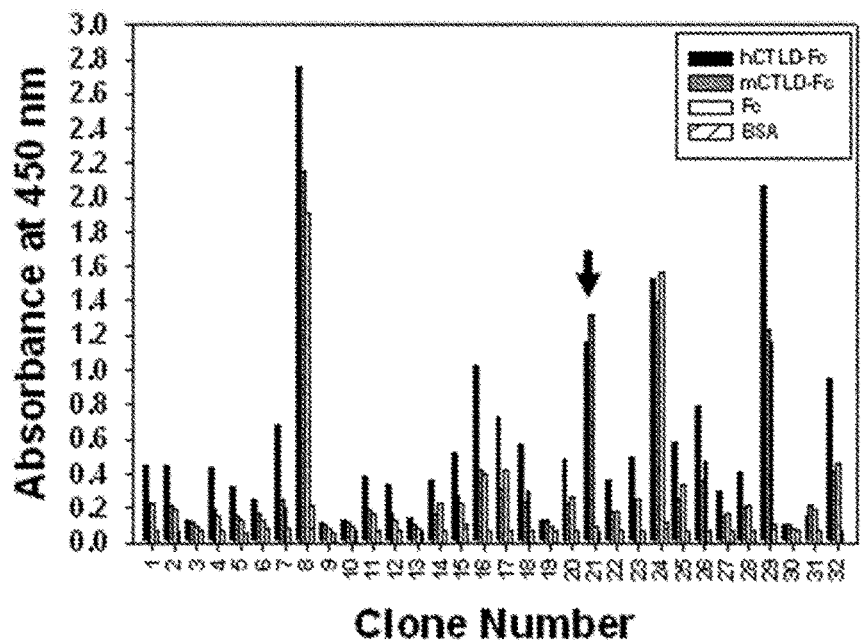
Figures 3C, 3D:
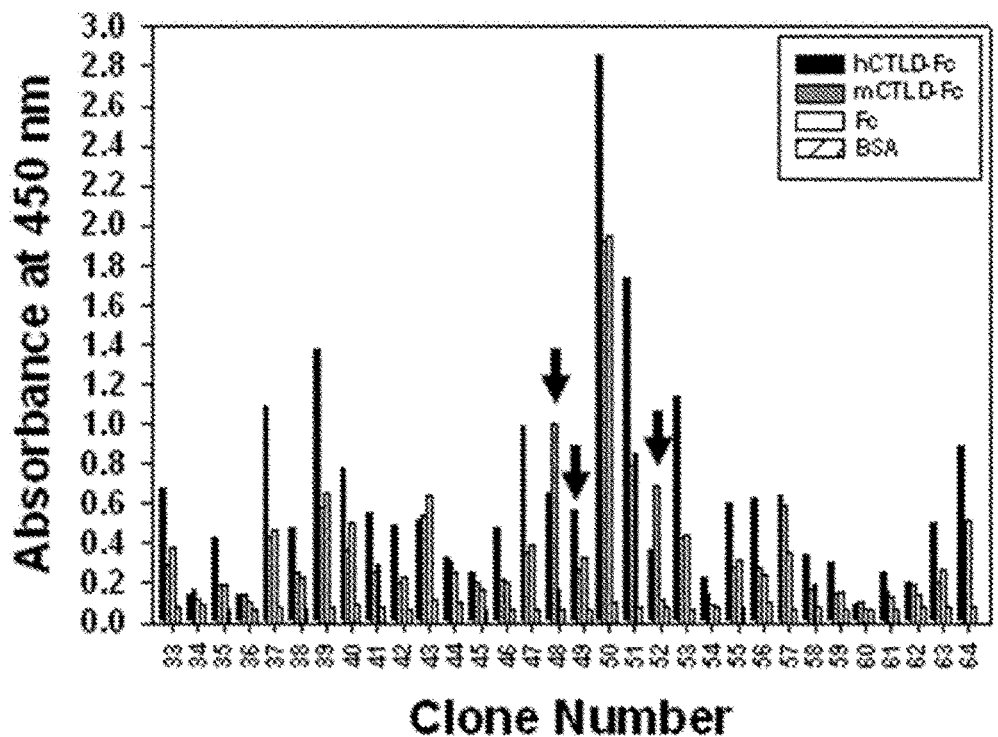

Alanine: A Arginine: R
Asparagine: N Aspartic acid: D
Cysteine: C Glutamic acid: E
Glutamine: Q Glycine: G
Histidine: H Isoleucine: I
Leucine: L Lysine: K
Methionine: M Phenylalanine: F
Proline: P Serine: S
Threonine: T Tryptophane: W
Tyrosine: Y Valine: V The library was then alternately biopanned with human (hCTLD-Fc) or mouse (mCTLD-Fc) CTLD fusion proteins, using CTLD-Fc-coated immunotubes and magnetic beads, to isolate clones having cross-species CTLD reactivity (FIG. 3a); several such clones were identified only with beads (FIG. 3b-3d). Ninety-six phage clones were randomly selected, rescued by phage enzyme immunoassay. Clone DNA was sequenced and four clones (clones 1-4), recognizing both human and mouse CTLDs and having different complementarity determining region sequences, were selected (Tables 2 to 9). Meanwhile, four clones can specifically recognize chimpanzee CTLD, having cross-reactivity because amino acid sequence of chimpanzee clec14a-lectin is the same as that of the human clec14a-lectin.

TABLE 2

Amino acid sequences of $V_H$ domains of clec14a-CTLD IgGs

| Clone 1 | FR1 | EVQLLESGGGLVQPGGSLRLSCAAS | SEQ ID NO: 13 |
|---|---|---|---|
| | CDR1 | GFTFSGYDMS | SEQ ID NO: 14 |
| | FR2 | WVRQAPGKGLEWVS | SEQ ID NO: 15 |
| | CDR2 | GIYPDGGNTYYADSVKG | SEQ ID NO: 16 |
| | FR3 | RFTISRDNSKNTLYLQMNSLRAEDTAVYYCAR | SEQ ID NO: 17 |
| | CDR3 | GATWWVLGPFDY | SEQ ID NO: 18 |
| | FR4 | WGQGTLVTVSS | SEQ ID NO: 19 |

TABLE 3

Amino acid sequences of $V_H$ domains of clec14a-CTLD IgGs

| Clone 2 | FR1 | EVQLLESGGGLVQPGGSLRLSCAAS | SEQ ID NO: 20 |
|---|---|---|---|
| | CDR1 | GFTFSSYDMS | SEQ ID NO: 21 |
| | FR2 | WVRQAPGKGLEWVS | SEQ ID NO: 22 |
| | CDR2 | VISPDSSTYYADSVKG | SEQ ID NO: 23 |
| | FR3 | RFTISRDNSKNTLHLQMNSLRAEDTAVYYCAR | SEQ ID NO: 24 |
| | CDR3 | HTGWQSRPHTYYDYGMDV | SEQ ID NO: 25 |
| | FR4 | WGQGTLVTVSS | SEQ ID NO: 26 |

TABLE 4

Amino acid sequences of $V_H$ domains of clec14a-CTLD IgGs

| Clone 3 | FR1 | EVQLLESGGGLVQPGGSLRLSCAAS | SEQ ID NO: 27 |
|---|---|---|---|
| | CDR1 | GFTFSDYYMS | SEQ ID NO: 28 |
| | FR2 | WVRQAPGKGLEWVS | SEQ ID NO: 29 |
| | CDR2 | LISYDGGSTYYADSVKG | SEQ ID NO: 30 |
| | FR3 | RFTISRDNSKNTLYLQMNSLRAEDTAVYYCAR | SEQ ID NO: 31 |
| | CDR3 | SNDWFDY | SEQ ID NO: 32 |
| | FR4 | WGQGTLVTVSS | SEQ ID NO: 33 |

TABLE 5

Amino acid sequences of $V_H$ domains of clec14a-CTLD IgGs

| Clone 4 | FR1 | EVQLLESGGGLVQPGGSLRLSCAAS | SEQ ID NO: 34 |
|---|---|---|---|
| | CDR1 | GFTFSGYYMS | SEQ ID NO: 35 |
| | FR2 | WVRQAPGKGLEWVS | SEQ ID NO: 36 |
| | CDR2 | VIYSGDGSTYYADSVKG | SEQ ID NO: 37 |
| | FR3 | RFTISRDNSKNTLYLQMNSLRAEDTAVYYCAR | SEQ ID NO: 38 |
| | CDR3 | GLNSSSALPFDY | SEQ ID NO: 39 |
| | FR4 | WGQGTLVTVSS | SEQ ID NO: 40 |

TABLE 6

Amino acid sequences of $V_L$ domains of clec14a-CTLD IgGs

| Clone 1 | FR1 | QSVLTQPPSASGTPGQRVTISC | SEQ ID NO: 41 |
|---|---|---|---|
| | CDR1 | TGSSSNIGNNSVT | SEQ ID NO: 42 |
| | FR2 | WYQQLPGTAPKLLIY | SEQ ID NO: 43 |
| | CDR2 | ADSHRPS | SEQ ID NO: 44 |
| | FR3 | GVPDRFSGSKSGTSASLAISGLRSEDEADYYC | SEQ ID NO: 45 |
| | CDR3 | GAWDDSLSGYV | SEQ ID NO: 46 |
| | FR4 | FGGGTKLTVL | SEQ ID NO: 47 |

TABLE 7

Amino acid sequences of $V_L$ domains of clec14a-CTLD IgGs

| Clone 2 | FR1 | QSVLTQPPSASGTPGQRVTISC | SEQ ID NO: 48 |
|---|---|---|---|
| | CDR1 | SGSSSNIGNNAVT | SEQ ID NO: 49 |

TABLE 7 -continued

Amino acid sequences of $V_L$ domains of clec14a-CTLD IgGs

|  |  |  |  |
|---|---|---|---|
|  | FR2 | WYQQLPGTAPKLLIY | SEQ ID NO: 50 |
|  | CDR2 | SDNHRPS | SEQ ID NO: 51 |
|  | FR3 | GVPDRFSGSKSGTSASLAISGLRSEDE ADYYC | SEQ ID NO: 52 |
|  | CDR3 | GTWDASLSGYV | SEQ ID NO: 53 |
|  | FR4 | FGGGTKLTVL | SEQ ID NO: 54 |

TABLE 8

Amino acid sequences of $V_L$ domains of clec14a-CTLD IgGs

| Clone 3 | FR1 | QSVLTQPPSASGTPGQRVTISC | SEQ ID NO: 55 |
|---|---|---|---|
|  | CDR1 | SGSSSNIGSNNVY | SEQ ID NO: 56 |
|  | FR2 | WYQQLPGTAPKLLIY | SEQ ID NO: 57 |
|  | CDR2 | YDSQRPS | SEQ ID NO: 58 |
|  | FR3 | GVPDRFSGSKSGTSASLAISGLRSEDE ADYYC | SEQ ID NO: 59 |
|  | CDR3 | GAWDDSLSAYV | SEQ ID NO: 60 |
|  | FR4 | FGGGTKLTVL | SEQ ID NO: 61 |

TABLE 9

Amino acid sequences of $V_L$ domains of clec14a-CTLD IgGs

| Clone 4 | FR1 | QSVLTQPPSASGTPGQRVTISC | SEQ ID NO: 62 |
|---|---|---|---|
|  | CDR1 | SGSSSNIGSNAVN | SEQ ID NO: 63 |
|  | FR2 | WYQQLPGTAPKLLIY | SEQ ID NO: 64 |
|  | CDR2 | ADSNRPS | SEQ ID NO: 65 |
|  | FR3 | GVPDRFSGSKSGTSASLAISGLRSEDE ADYYC | SEQ ID NO: 66 |
|  | CDR3 | GSWDYSLSAYV | SEQ ID NO: 67 |
|  | FR4 | FGGGTKLTVL | SEQ ID NO: 68 |

Also, the nucleic acid sequences of clones 1-4 is the same as the following tables 10 to 17.

TABLE 10

Nucleotide sequences of $V_H$ domains of clec14a-CTLD IgGs

| Clone 1 | FR1 | gaggtgcagctgttggagtctgggggag gcttggtacagcctggggggtccctgag actctcctgtgcagcctct | SEQ ID NO: 69 |
|---|---|---|---|
|  | CDR1 | ggattcacctttagcggttatgatatgagc | SEQ ID NO: 70 |
|  | FR2 | tgggtccgccaggctccagggaaggggctg gagtgggtctca | SEQ ID NO: 71 |
|  | CDR2 | gggatctatcctgatggtggtaatacatat tacgctgattctgtaaaaggt | SEQ ID NO: 72 |
|  | FR3 | cggttcaccatctccagagacaattccaag aacacgctgtatctgcaaatgaacagcctg agagccgaggacacggccgtgtattactgt gcgaga | SEQ ID NO: 73 |
|  | CDR3 | ggtgctacgtggtgggtgcttggtcctttc gactac | SEQ ID NO: 74 |
|  | FR4 | tggggccagggtacactggtcaccgtgagc tca | SEQ ID NO: 75 |

TABLE 11

Nucleotide sequences of $V_L$ domains of clec14a-CTLD IgGs

| Clone 1 | FR1 | cagtctgtgctgactcagccaccctcag cgtctgggaccccggggcagagggtcac catctcttgt | SEQ ID NO: 76 |
|---|---|---|---|
|  | CDR1 | actggctcttcatctaatattggcaata attctgtcacc | SEQ ID NO: 77 |
|  | FR2 | tggtaccagcagctcccaggaacggccc ccaaaactcctcatctat | SEQ ID NO: 78 |
|  | CDR2 | gctgatagtcatcggccaagc | SEQ ID NO: 79 |
|  | FR3 | ggggtccctgaccgattctctggctccaa gtctggcacctcagcctcccctggccatca gtgggctccggtccgaggatgaggctgat tattactgt | SEQ ID NO: 80 |
|  | CDR3 | ggtgcttgggatgatagcctgagtggtta tgtc | SEQ ID NO: 81 |
|  | FR4 | ttcggcggaggcaccaagctgacggt ccta | SEQ ID NO: 82 |

TABLE 12

Nucleotide sequences of $V_H$ domains of clec14a-CTLD IgGs

| Clone 2 | FR1 | gaggtgcagctgttggagtctgggggaggc ttggtacagcctggggggtccctgagactc tcctgtgcagcctct | SEQ ID NO: 83 |
|---|---|---|---|
|  | CDR1 | ggattcacctttagcagttatgatatgagc | SEQ ID NO: 84 |
|  | FR2 | tgggtccgccaggctccagggaaggggctg gagtgggtctca | SEQ ID NO: 85 |
|  | CDR2 | gtgatctctcctgatagtagtagtacatat tacgctgattctgtaaaaggt | SEQ ID NO: 86 |
|  | FR3 | cggttcaccatctccagagacaattccaag | SEQ ID |

TABLE 12-continued

Nucleotide sequences of $V_H$ domains of clec14a-CTLD IgGs

| | | | |
|---|---|---|---|
| | | aacacgctgcatctgcaaatgaacagcctg agagccgaggacacggccgtgtattactgt gcgaga | SEQ ID NO: 87 |
| | CDR3 | catactggttggcagagtcggcctcatacg tattatgattatggtatggacgtc | SEQ ID NO: 88 |
| | FR4 | tggggccagggtacactggtcaccgtga gctca | SEQ ID NO: 89 |

TABLE 13

Nucleotide sequences of $V_L$ domains of clec14a-CTLD IgGs

| | | | |
|---|---|---|---|
| Clone 2 | FR1 | cagtctgtgctgactcagccaccctcag cgtctgggaccccgggcagagggtcac catctcttgt | SEQ ID NO: 90 |
| | CDR1 | agtggctcttcatctaatattggcaata atgctgtcacc | SEQ ID NO: 91 |
| | FR2 | tggtaccagcagctcccaggaacggccc ccaaactcctcatctat | SEQ ID NO: 92 |
| | CDR2 | tctgataatcatcggccaagc | SEQ ID NO: 93 |
| | FR3 | ggggtccctgaccgattctctggctcca agtctggcacctcagcctcnctggccat cagtgggctccggtccgaggatgaggct gattattactgt | SEQ ID NO: 94 |
| | CDR3 | ggtacttgggatgctagcctgagtggtt atgtc | SEQ ID NO: 95 |
| | FR4 | ttcggcggaggcaccaagctgacggt ccta | SEQ ID NO: 96 |

TABLE 14

Nucleotide sequences of $V_H$ domains of clec14a-CTLD IgGs

| | | | |
|---|---|---|---|
| Clone 3 | FR1 | gaggtgcagctgttggagtctggggga ggcttggtacagcctggggggtccctg agactctcctgtgcagcctct | SEQ ID NO: 97 |
| | CDR1 | ggattcacctttagcgattattatatgc | SEQ ID NO: 98 |
| | FR2 | tgggtccgccaggctccagggaaggg ctggagtgggtctca | SEQ ID NO: 99 |
| | CDR2 | ttgatctcttatgatggtggtagtaca tattacgctgattctgtaaaaggt | SEQ ID NO: 100 |
| | FR3 | cggttcaccatctccagagacaattcc aagaacacgctgtatctgcaaatgaac agcctgagagccgaggacacggccgtg tattactgtgcgaga | SEQ ID NO: 101 |
| | CDR3 | agtaatgattggttcgactac | SEQ ID NO: 102 |
| | FR4 | tggggccagggtacactggtcaccgt gagctca | SEQ ID NO: 103 |

TABLE 15

Nucleotide sequences of $V_L$ domains of clec14a-CTLD IgGs

| | | | |
|---|---|---|---|
| Clone 3 | FR1 | cagtctgtgctgactcagccaccctcag cgtctgggaccccgggcagagggtcac catctcttgt | SEQ ID NO: 104 |
| | CDR1 | agtggctcttcatctaatattggcagta ataatgtctac | SEQ ID NO: 105 |
| | FR2 | tggtaccagcagctcccaggaacggctc ccaaactcctcatctat | SEQ ID NO: 106 |
| | CDR2 | tatgatagtcagcggccaagc | SEQ ID NO: 107 |
| | FR3 | ggggtccctgaccgattctctggctcca agtctggcacctcagcctccctggccat cagtgggctccggtccgaggatgaggct gattattactgt | SEQ ID NO: 108 |
| | CDR3 | ggtgcttgggatgatagcctgagtgctt atgtc | SEQ ID NO: 109 |
| | FR4 | ttcggcggaggcaccaagctgacggt cctat | SEQ ID NO: 110 |

TABLE 16

Nucleotide sequences of $V_H$ domains of clec14a-CTLD IgGs

| | | | |
|---|---|---|---|
| Clone 4 | FR1 | gaggtgcagctgttggagtctggggag gcttggtacagcctggggggtccctgag actctcctgtgcagcctct | SEQ ID NO: 111 |
| | CDR1 | ggattcacctttagcggttattatatgagc | SEQ ID NO: 112 |
| | FR2 | tgggtccgccaggctccagggaaggggctg gagtgggtctca | SEQ ID NO: 113 |
| | CDR2 | gtgatctattctggtgatggtagtacata ttacgctgattctgtaaaaggt | SEQ ID NO: 114 |
| | FR3 | cggttcaccatctccagagacaactccaa gaacacgctgtatctgcaaatgaacagcc tgagagccgaggacacggccgtgtattac tgtgcgaga | SEQ ID NO: 115 |
| | CDR3 | ggtcttaattcgtcttcggctctgccgttcg actac | SEQ ID NO: 116 |
| | FR4 | tggggccagggtacactggtcaccgtga gctca | SEQ ID NO: 117 |

TABLE 17

Nucleotide sequences of $V_L$ domains of clec14a-CTLD IgGs

| | | | |
|---|---|---|---|
| Clone 4 | FR1 | cagtctgtgctgactcagccaccctcagcg tctgggaccccgggcagagggtcaccatc tcttgt | SEQ ID NO: 118 |
| | CDR1 | agtggctcttcatctaatattggcagtaat gctgtcaac | SEQ ID NO: 119 |
| | FR2 | tggtaccagcagctcccaggaacggccccc aaactcctcatctat | SEQ ID NO: 120 |
| | CDR2 | gctgatagtaatcggccaagc | SEQ ID NO: 121 |

TABLE 17-continued

Nucleotide sequences of $V_L$ domains of clec14a-CTLD IgGs

| | | |
|---|---|---|
| FR3 | ggggtccctgaccgattctctggctccaag tctggcacctcagcctccctggccatcagt gggctccggtccgaggatgaggctgattat tactgt | SEQ ID NO: 122 |
| CDR3 | ggttcttgggattatagcctgagtggttat gtc | SEQ ID NO: 123 |
| FR4 | ttcggcggaggtaccaagctgacggtccta | SEQ ID NO: 124 |

Experimental Example 3: Clec14a-CTLD IgGs Specifically Recognized Human and Mouse Clec14a-CTLDs The scFv clones were converted to IgG, expressed in human embryonic kidney 293F (HEK293F) cells, and purified. The four IgG clones was shown to be greater than 90% pure by sodium dodecyl sulfate polyacrylamide gel electrophoresis (SDS-PAGE) and Coomassie staining. ELISA showed that the purified CTLD-specific IgGs (clec14a-CTLD IgGs) specifically bound both human and mouse CTLD-Fc, and not Fc alone. Clones 1 and 2 showed much greater affinity than clones 3 and 4 (FIG. 4).

Figure 5A:
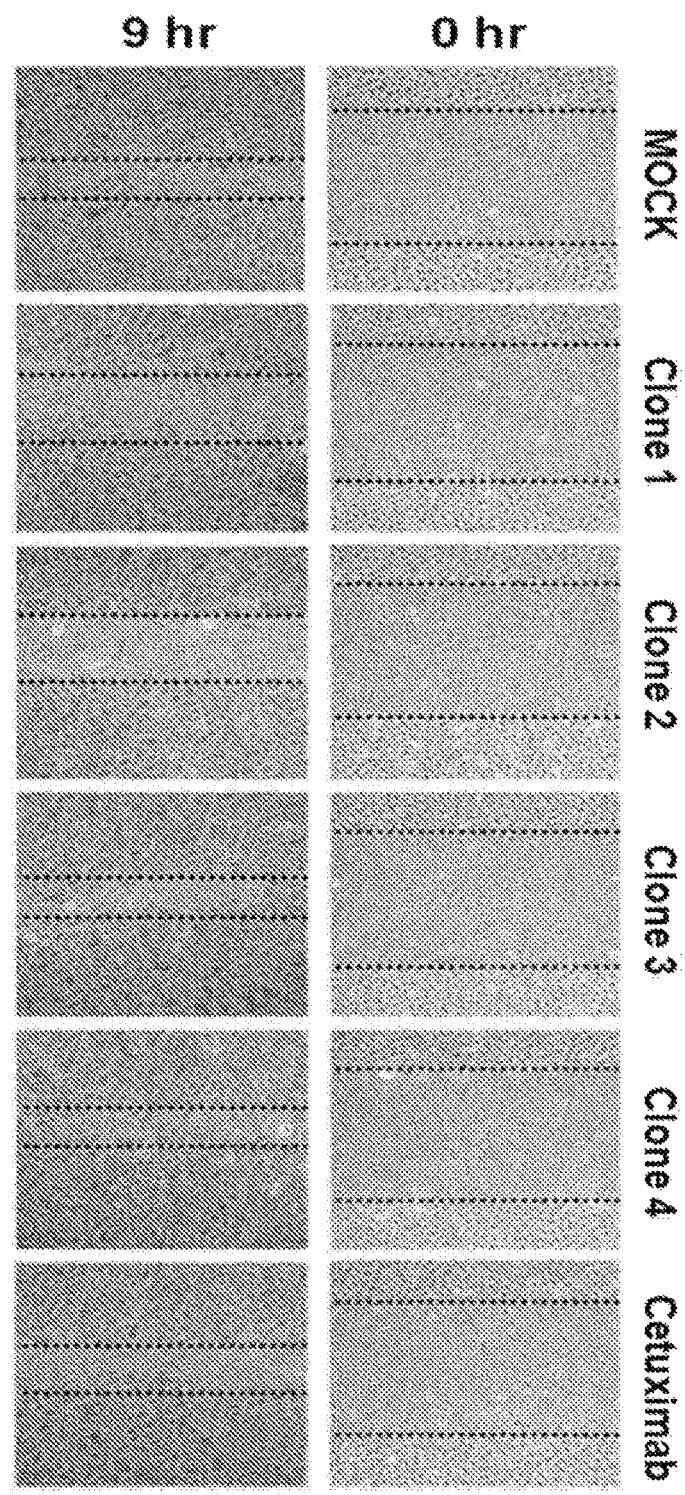
FIG. 5. shows the effect of clec14a-CTLD IgGs on endothelial cell migration and tube formation. a. After wounding, migration of HUVECs incubated in the absence (MOCK) or presence of clec14a-CTLD IgG (clones 1-4) or cetuximab was monitored by light microscopy. Images were captured at 0 hr (top) and 9 hr (bottom). b. Distance migrated is expressed as percent of control (MOCK) migration. Values represent mean±SD of triplicate measurements from one of three independent experiments. c. Tube formation was assayed in the absence (MOCK) or presence of clec14a-CTLD IgG (clones 1-4) or cetuximab. d. Extent of tube formation is expressed as percent of control (MOCK) tube formation. Values represent mean±SD of triplicate measurements from one of three independent experiments.
Figure 5B:
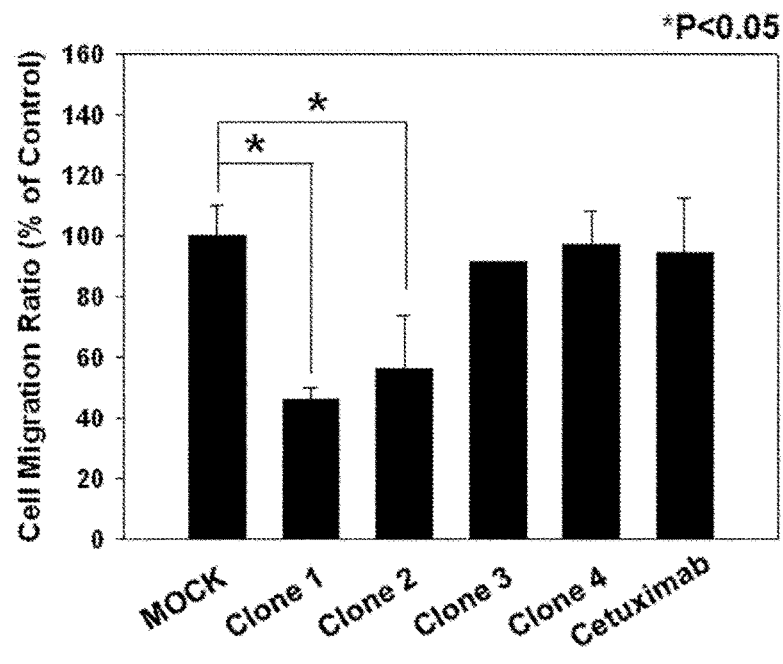

Experimental Example 4: Clec14a-CTLD IgGs Specifically Suppressed Endothelial Cell Migration and Tube Formation To investigate the inhibitory effect of clec14a-CTLD IgGs on endothelial cell migration, wound healing assays with HUVECs were performed in the absence or presence of clec14a-CTLD IgGs. Cetuximab, an anti-EGFR antibody, was used as control IgG. Of the selected clec14a-CTLD IgGs, clones 1 and 2 significantly suppressed HUVEC cell migration to approximately 44% and 54%, respectively, whereas clones 3 and 4 and cetuximab alone had little effect. (FIGS. 5a and 5b).

Figure 5C:
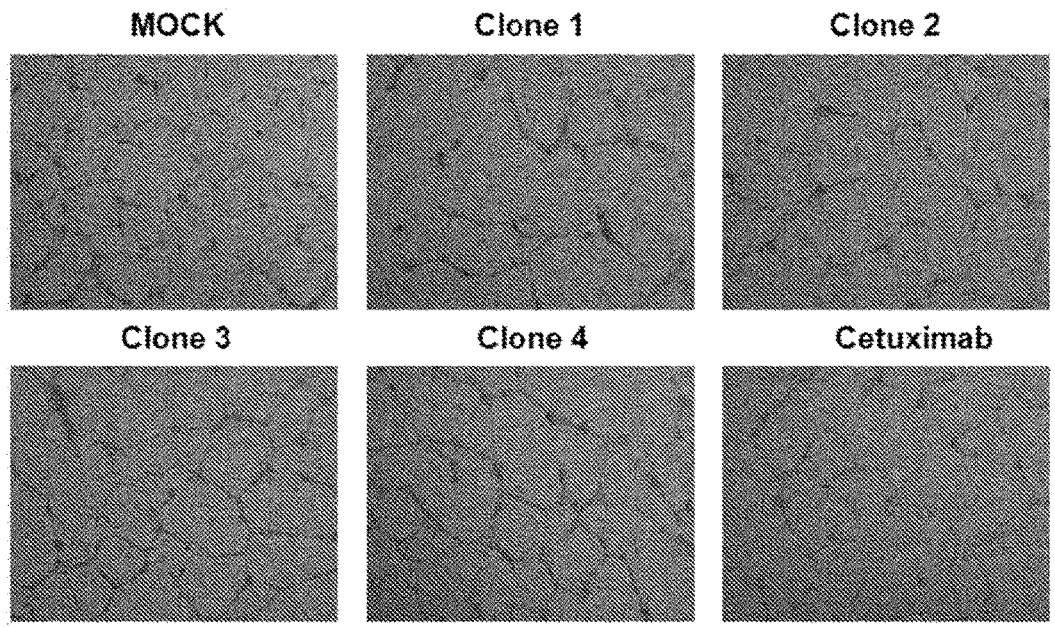
Figure 5D:
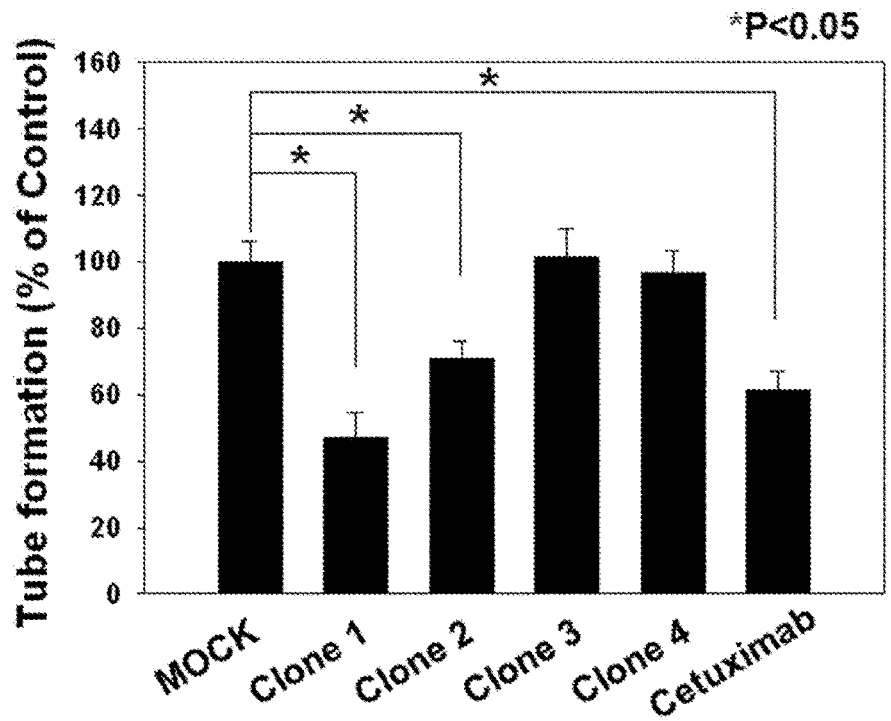

To determine the effect of clec14a-CTLD IgGs on tube formation, tube formation was assayed in the absence or presence of the clec14a-CTLD IgGs and cetuximab. Clones 1 and 2, and cetuximab as previously reported specifically blocked HUVEC tube formation, whereas the other clones did not have a significant effect (FIGS. 5c and 5d).

These results strongly suggest that clec14a-CTLD IgGs specifically inhibits tumor angiogenesis.

Figure 6A:
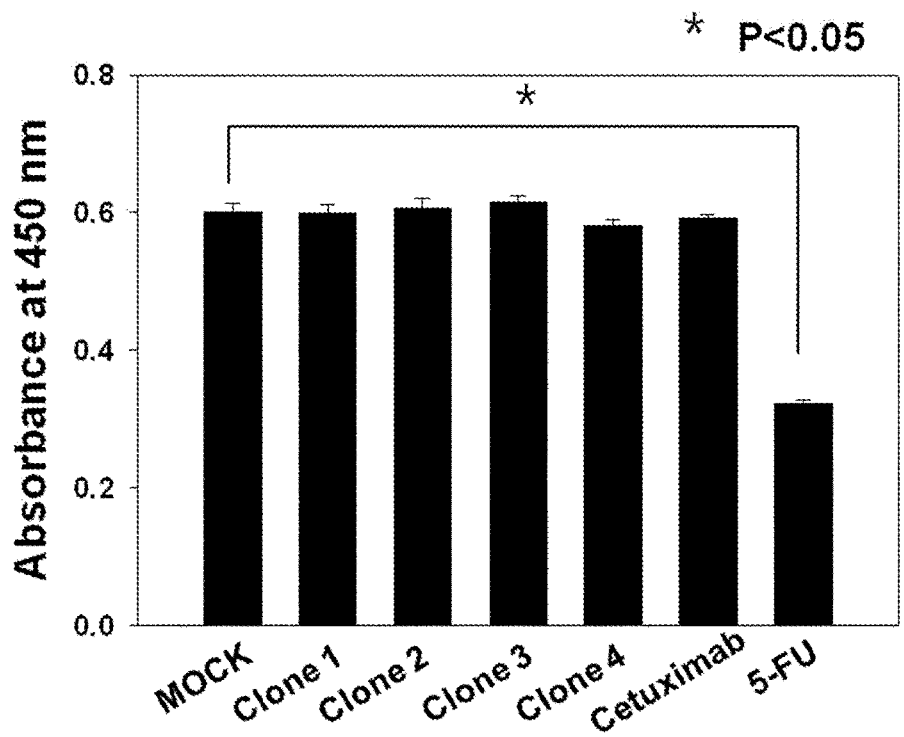
FIG. 6. shows the effect of clec14a-CTLD IgGs on endothelial cell proliferation and activation. a. HUVECs were incubated in the absence (MOCK) or presence of clec14a-CTLD IgGs, cetuximab, or 5-FU (positive control) for 2 days. Cell viability was assessed by measuring absorbance at 450 nm. Values represent mean±SD of triplicate measurements from one of two independent experiments. b. HUVECs were cultured in the absence (dashed line) or presence (solid line) of hTNFα, clec14a-CTLD IgGs, or cetuximab; stained with anti-VCAM-1 (upper) or ICAM-1 (lower) polyclonal antibody; and analyzed by flow cytometry. hTNFα served as a positive control for endothelial cell activation. Results are representative of three independent experiments.

Experimental Example 5: Effect of Clec14a-CTLD IgGs on Endothelial Cell Viability and Activation To investigate the effect of clec14a-CTLD IgGs on endothelial cell viability, HUVECs were cultured in the absence or presence of clec14a-CTLD IgGs, cetuximab, or 5-fluorouracil (5-FU), an apoptosis inducer, for 2 days, and cell viability was checked using a cell counting kit. The antibodies had little effect on HUVEC viability, whereas 5-FU specifically decreased viability (FIG. 6a).

Figure 6B:
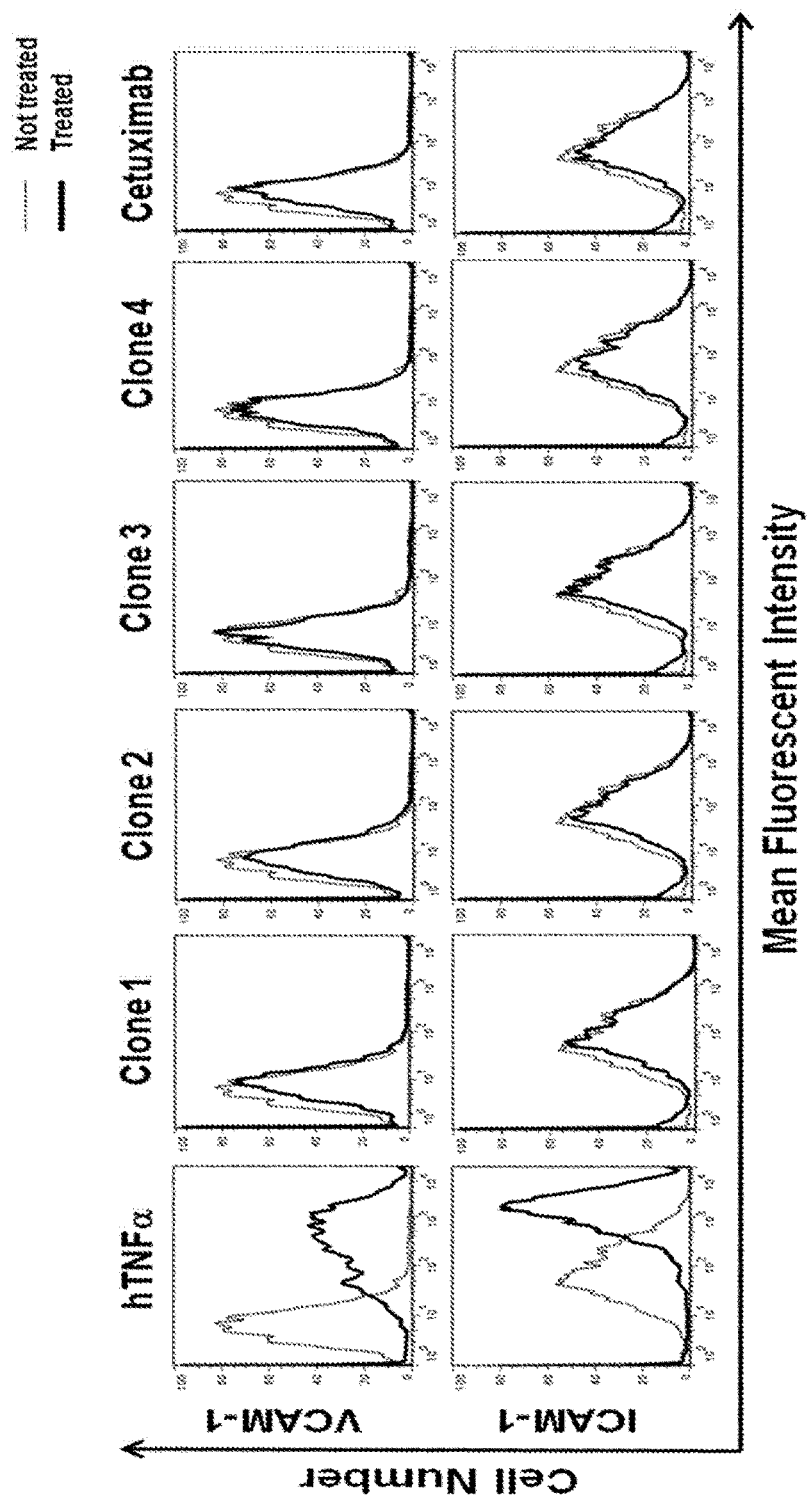

To determine the effect of clec14a-CTLD IgGs on endothelial cell activation, HUVECs were cultured in the absence or presence of clec14a-CTLD IgGs, cetuximab, or human tumor necrosis factor alpha (hTNFα). Activation was determined based on the expression of vascular cell adhesion molecule-1 (VCAM-1) and intercellular cell adhesion molecule-1 (ICAM-1) measured by flow cytometry. Cells were treated with hTNFα, which induces up-regulation of VCAM-1 and ICAM-1, as a positive control. The antibodies and cetuximab had no effect on HUVEC activation (FIG. 6b).

Taken together, these results suggest that clec14a-CTLD IgGs have little effect on endothelial cell viability or activation.

Experimental Example 6: Clec14a-CTLD IgGs Specifically Inhibited Clec14a-Mediated Cell-Cell Contact To elucidate the role of clec14a-CTLD IgGs in endothelial cell-cell contact, the number of cell aggregates, an indicator of clec14a-mediated cell-cell contacts, formed by HEK293F cells transfected with GFP or clec14a-GFP and grown in the absence or presence of clec14a-CTLD IgGs or cetuximab was determined. The number of cell aggregates was approximately 4-fold greater in cells expressing clec14a-GFP than in those expressing GFP alone (FIGS. 7a and 7b). Furthermore, clones 1 and 2 significantly suppressed the aggregation of cells transfected with clec14a-GFP, whereas the other clones and cetuximab had little effect.

Taken together, these results suggest that clec14a-CTLD IgGs may play an inhibitory role in clec14a-mediated endothelial cell-cell contact during tumor angiogenesis.

Experimental Example 7: Clec14a-CTLD IgG Specifically Blocked Clec14a CTLD-CTLD Interactions Immunoanalysis was used to confirm the expression of GFP, clec14a-GFP, and clec14aΔCTLD-GFP in lysates of transfected COS-7 cells (FIG. 8a). Lysates were then incubated with hCTLD-Fc or Fc to observe interactions between CTLDs. Although hCTLD-Fc may interact with some other proteins in COS-7 cell lysates, it bound strongly to clec14a-GFP but not to clec14aΔCTLD-GFP, suggesting a specific CTLDCTLD interaction in endothelial cells (FIG. 8b).

To determine if clec14a-CTLD IgG blocks CTLD-CTLD interactions, hCTLD-Fc was incubated with increasing concentrations of clec14a-CTLD IgG (clone 1) and the protein complexes were incubated with lysates of GFP- or clec14a-GFP-transfected cells. Competitive ELISA showed that clec14a-CTLD IgG specifically inhibited CTLD-CTLD interactions in a concentration-dependent manner (FIG. 8c), suggesting that clec14a-CTLD IgG may specifically block clec14a CTLD-CTLD interactions in endothelial cells.

Experimental Example 8: Cross-Linking with Clec14a-CTLD IgG Downregulated Clec14a on the Surface of HUVECs To investigate a possible role of clec14a-CTLD IgG in suppressing pro-angiogenenic phenotypes, flow cytometry was used to compare the level of clec14a expression on HUVEC membranes before and after treatment with clec14a-CTLD IgG (clone 1). IgG treatment significantly reduced clec14a on live, but not paraformaldehyde-fixed, cells (FIG. 9a).

To confirm down-regulation of clec14a on HUVEC membranes by clec14a-CTLD IgG, cells were treated with IgG (clone 1) or Fc, and membrane clec14a was measured by cell ELISA. Clec14a-CTLD IgG down-regulated clec14a on HUVEC membranes in a time-dependent manner (FIG. 9b).

These results strongly suggest that clec14a-CTLD IgG cross-linking of clec14a specifically down-regulates clec14a on endothelial cell membranes. Additionally, these results suggest that clec14a-CTLD IgG is capable of being internalized into a cell expressing clec14a such as a cancer cell.

Experimental Example 9: Fine Mapping of Epitope

For fine mapping of epitope, specificity of clec14a-CTLD IgGs to Clec14awtCTLD and the fragments of hCTLD-Fc (FIG. 10a) were tested by ELISA.

As a result, as can be seen FIG. 10b, clec14a-CTLD IgGs of both clone 1 and clone 2 specifically bound the N-terminal and C-terminal of hCTLD as well as wthCTLD.

These results strongly suggest that the N-terminal or C-terminal region of CTLD such as clec14a-CTLD IgGs of both clone 1 and clone 2 specifically bound a fusion protein comprising an amino acid fragment from 1st amino acid to 42nd amino acid in hCTLD, a fusion protein comprising an amino acid fragment from 1st amino acid to 62nd amino acid in hCTLD, a fusion protein comprising an amino acid fragment from 82nd amino acid to 142nd amino acid in hCTLD, a fusion protein comprising an amino acid fragment from 62nd amino acid to 142nd amino acid in hCTLD and a fusion protein comprising an amino acid fragment from 122nd amino acid to 142nd amino acid in hCTLD can be used as an epitope.

Experimental Example 10: Test for Examining if CTLD-Fc Inhibits Tube Formation

To investigate the inhibitory effect of hCTLD-Fc on angiogenesis, tube formation was assayed in the presence hCTLD-Fc or Fc according to example 16.

As a result, as can be seen FIG. 11, hCTLD-Fc inhibited tube formation in a concentration-dependent manner.

These results strongly suggest that hCTLD-Fc specifically inhibits tumor angiogenesis.

INDUSTRIAL APPLICABILITY

Based on the novel finding that the CTLD of clec14a plays an important role in cell migration and filopodium formation, the present invention identified the function of a novel antibody against CTLD in suppressing angiogenesis. Accordingly, the present invention provides a novel target domain which will be available for suppressing angiogenesis. Further, the antibody of the present invention can be effective for preventing or treating angiogenesis-related diseases or clec14a-mediated cancer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

SEQUENCE LISTING FREE TEXT

Attach electronic file.

---

The invention claimed is:

1. An antibody, binding specifically to CTLD (C-type lectin like domain) of clec14a (C-type lectin domain family 14, member A), wherein the antibody comprises at least one selected from the group consisting of:

(a) a heavy-chain variable region comprising heavy-chain CDR1 defined by an amino acid sequence of SEQ ID NO: 14, heavy-chain CDR2 defined by an amino acid sequence of SEQ ID NO: 16, and heavy-chain CDR3 defined by an amino acid sequence of SEQ ID NO: 18, and a light-chain variable region comprising light-chain CDR1 defined by an amino acid sequence of SEQ ID NO: 42, light-chain CDR2 defined by an amino acid sequence of SEQ ID NO: 44, and light-chain CDR3 defined by an amino acid sequence of SEQ ID NO: 46;

(b) a heavy-chain variable region comprising heavy-chain CDR1 defined by an amino acid sequence of SEQ ID NO: 21, heavy-chain CDR2 defined by an amino acid sequence of SEQ ID NO: 23, and heavy-chain CDR3 defined by an amino acid sequence of SEQ ID NO: 25, and a light-chain variable region comprising light-chain CDR1 defined by an amino acid sequence of SEQ ID NO: 49, light-chain CDR2 defined by an amino acid sequence of SEQ ID NO: 51, and light-chain CDR3 defined by an amino acid sequence of SEQ ID NO: 53;

(c) a heavy-chain variable region comprising heavy-chain CDR1 defined by an amino acid sequence of SEQ ID NO: 28, heavy-chain CDR2 defined by an amino acid sequence of SEQ ID NO: 30, and heavy-chain CDR3 defined by an amino acid sequence of SEQ ID NO: 32, and a light-chain variable region comprising light-chain CDR1 defined by an amino acid sequence of SEQ ID NO: 56, light-chain CDR2 defined by an amino acid sequence of SEQ ID NO: 58, and light-chain CDR3 defined by an amino acid sequence of SEQ ID NO: 60; and (d) a heavy-chain variable region comprising heavy-chain CDR1 defined by an amino acid sequence of SEQ ID NO: 35, heavy-chain CDR2 defined by an amino acid sequence of SEQ ID NO: 37, and heavy-chain CDR3 defined by an amino acid sequence of SEQ ID NO: 39, and a light-chain variable region comprising light-chain CDR1 defined by an amino acid sequence of SEQ ID NO: 63, light-chain CDR2 defined by an amino acid sequence of SEQ ID NO: 65, and light-chain CDR3 defined by an amino acid sequence of SEQ ID NO: 67.

2. The antibody of claim 1, wherein the antibody is selected from the group consisting of:

an antibody comprising a heavy-chain variable region having an amino acid sequence of SEQ ID NO: 125 and a light-chain variable region having an amino acid sequence of SEQ ID NO: 129;

an antibody comprising a heavy-chain variable region having an amino acid sequence of SEQ ID NO: 126 and a light-chain variable region having an amino acid sequence of SEQ ID NO: 130;

an antibody comprising a heavy-chain variable region having an amino acid sequence of SEQ ID NO: 127 and a light-chain variable region having an amino acid sequence of SEQ ID NO: 131; and an antibody comprising a heavy-chain variable region having an amino acid sequence of SEQ ID NO: 128 and a light-chain variable region having an amino acid sequence of SEQ ID NO: 132.

3. An antibody-drug conjugate comprising the antibody of claim 1 attached to a drug, wherein the drug is any one selected from the group consisting of a toxin, a chemotherapeutic agent, an anticancer drug, an antibiotic, ADP-ribosyl transferase, a radioactive isotope and a nucleolytic enzyme.

4. A diagnostic kit for angiogenesis-related disease, comprising the antibody of claim 1.

* * * * *

SEQUENCE LISTING

```
<160> NUMBER OF SEQ ID NOS: 142

<210> SEQ ID NO 1
<211> LENGTH: 33
<212> TYPE: DNA
<213> ORGANISM: Artificial Sequence
<220> FEATURE:
<223> OTHER INFORMATION: Primer for hCTLD

<400> SEQUENCE: 1
tcgcgcggcc gctgctcggc ctcgggggcc tgc                                    33

<210> SEQ ID NO 2
<211> LENGTH: 30
<212> TYPE: DNA
<213> ORGANISM: Artificial Sequence
<220> FEATURE:
<223> OTHER INFORMATION: Primer for hCTLD

<400> SEQUENCE: 2
tcgcctcgag cttgcacagg tagccgttgg                                        30

<210> SEQ ID NO 3
<211> LENGTH: 37
<212> TYPE: DNA
<213> ORGANISM: Artificial Sequence
<220> FEATURE:
<223> OTHER INFORMATION: Primer for mCTLD

<400> SEQUENCE: 3
tcgcggccca ggcggcctgt tcggcctcgg gggcttg                                37
```

<210> SEQ ID NO 4
<211> LENGTH: 37
<212> TYPE: DNA
<213> ORGANISM: Artificial Sequence
<220> FEATURE:
<223> OTHER INFORMATION: Primer for mCTLD

<400> SEQUENCE: 4
tcgcggccgg cctggccctt gcataggtag ccatcgg        37

<210> SEQ ID NO 5
<211> LENGTH: 100
<212> TYPE: DNA
<213> ORGANISM: Artificial Sequence
<220> FEATURE:
<223> OTHER INFORMATION: Primer for VH

<400> SEQUENCE: 5
cgggaattcg ccgccaccat ggaatggagc tgggtctttc        40
tcttcttcct gctgtcagta actacaggtg tcctctccga        80
ggtgcagctg ttggagtctg        100

<210> SEQ ID NO 6
<211> LENGTH: 51
<212> TYPE: DNA
<213> ORGANISM: Artificial Sequence
<220> FEATURE:
<223> OTHER INFORMATION: Primer for VH

<400> SEQUENCE: 6
ggcgggccct tggtggaggc tgagctcacg gtgaccagtg        40
cccttggccc c        51

<210> SEQ ID NO 7
<211> LENGTH: 99
<212> TYPE: DNA
<213> ORGANISM: Artificial Sequence
<220> FEATURE:
<223> OTHER INFORMATION: Primer for VL

<400> SEQUENCE: 7
cccaagcttg ccgccaccat ggagacacat tctcaggtct        40
ttgtatacat gttgctgtgg ttgtctggtg ttgaaggacc        80
agtctgtgct gactcagcc        99

<210> SEQ ID NO 8
<211> LENGTH: 51
<212> TYPE: DNA
<213> ORGANISM: Artificial Sequence
<220> FEATURE:
<223> OTHER INFORMATION: Primer for VL

<400> SEQUENCE: 8
ggccgtacgt aggaccgtca gcttggtgcc tccgcctaag        40
acataaccac c        51

<210> SEQ ID NO 9
<211> LENGTH: 142
<212> TYPE: PRT
<213> ORGANISM: Homo sapiens
<220> FEATURE:
<221> NAME/KEY: DOMAIN
<222> LOCATION: (1)..(142)

<223> OTHER INFORMATION: Human clec14a-lectin (a.a 31-172)

<400> SEQUENCE: 9

Cys Ser Ala Ser Gly Ala Cys Tyr Ser Leu His His Ala Thr Met Lys
 1               5                  10                  15

Arg Gln Ala Ala Glu Glu Ala Cys Ile Leu Arg Gly Gly Ala Leu Ser
             20                  25                  30

Thr Val Arg Ala Gly Ala Glu Leu Arg Ala Val Leu Ala Leu Leu Arg
         35                  40                  45

Ala Gly Pro Gly Pro Gly Gly Gly Ser Lys Asp Leu Leu Phe Trp Val
     50                  55                  60

Ala Leu Glu Arg Arg Arg Ser His Cys Thr Leu Glu Asn Glu Pro Leu
 65                  70                  75                  80

Arg Gly Phe Ser Trp Leu Ser Ser Asp Pro Gly Gly Leu Glu Ser Asp
                 85                  90                  95

Thr Leu Gln Trp Val Glu Glu Pro Gln Arg Ser Cys Thr Ala Arg Arg
            100                 105                 110

Cys Ala Val Leu Gln Ala Thr Gly Gly Val Glu Pro Ala Gly Trp Lys
        115                 120                 125

Glu Met Arg Cys His Leu Arg Ala Asn Gly Tyr Leu Cys Lys
    130                 135                 140

<210> SEQ ID NO 10
<211> LENGTH: 142
<212> TYPE: PRT
<213> ORGANISM: Mus musculus
<220> FEATURE:
<221> NAME/KEY: DOMAIN
<222> LOCATION: (1)..(142)
<223> OTHER INFORMATION: Mouse clec14a-lectin (a.a 31-172)

<400> SEQUENCE: 10

Cys Ser Ala Ser Gly Ala Cys Tyr Ser Leu His His Ala Thr Phe Lys
 1               5                  10                  15

Arg Arg Ala Ala Glu Glu Ala Cys Ser Leu Arg Gly Gly Thr Leu Ser
             20                  25                  30

Thr Val His Ser Gly Ser Glu Phe Gln Ala Val Leu Leu Leu Leu Arg
         35                  40                  45

Ala Gly Pro Gly Pro Gly Gly Gly Ser Lys Asp Leu Leu Phe Trp Val
     50                  55                  60

Ala Leu Glu Arg Ser Ile Ser Gln Cys Thr Gln Glu Lys Glu Pro Leu
 65                  70                  75                  80

Arg Gly Phe Ser Trp Leu His Pro Asp Ser Glu Asp Ser Glu Asp Ser
                 85                  90                  95

Pro Leu Pro Trp Val Glu Glu Pro Gln Arg Ser Cys Thr Val Arg Lys
            100                 105                 110

Cys Ala Ala Leu Gln Ala Thr Arg Gly Val Glu Pro Ala Gly Trp Lys
        115                 120                 125

Glu Met Arg Cys His Leu Arg Thr Asp Gly Tyr Leu Cys Lys
    130                 135                 140

<210> SEQ ID NO 11
<211> LENGTH: 426
<212> TYPE: DNA
<213> ORGANISM: Homo sapiens
<220> FEATURE:
<221> NAME/KEY: exon
<222> LOCATION: (1)..(426)
<223> OTHER INFORMATION: Human clec14a-lectin (nt 91-516)

-continued

```
<400> SEQUENCE: 11
tgctcggcct cggggccctg ctacagcctg caccacgcta                           40
ccatgaagcg gcaggcggcc gaggaggcct gcatcctgcg                           80
aggtggggcg ctcagcaccg tgcgtgcggg cgccgagctg                          120
cgcgctgtgc tcgcgctcct gcgggcaggc ccagggcccg                          160
gagggggctc caaagacctg ctgttctggg tcgcactgga                          200
gcgcaggcgt tcccactgca ccctggagaa cgagcctttg                          240
cggggtttct cctggctgtc ctccgacccc ggcggtctcg                          280
aaagcgacac gctgcagtgg gtggaggagc cccaacgctc                          320
ctgcaccgcg cggagatgcg cggtactcca ggccaccggt                          360
ggggtcgagc ccgcaggctg gaaggagatg cgatgccacc                          400
tgcgcgccaa cggctacctg tgcaag                                         426

<210> SEQ ID NO 12
<211> LENGTH: 426
<212> TYPE: DNA
<213> ORGANISM: Mus musculus
<220> FEATURE:
<221> NAME/KEY: exon
<222> LOCATION: (1)..(426)
<223> OTHER INFORMATION: Mouse clec14a-lectin (nt 91-516)

<400> SEQUENCE: 12
tgttcggcct cggggcttg ctacagcctt caccacgcta                            40
ccttcaagag aagggcggcg gaggaggcct gcagcctaag                           80
gggcgggact ctcagcaccg tgcactcagg ctcggagttt                          120
caagctgtgc tcctgctctt gcgtgcaggt cccgggcctg                          160
gcggaggctc caaagatctt ctgttctggg tggctctgga                          200
acgcagcatc tcacagtgca ctcaggagaa agagccttta                          240 aggggttttct cctggttgca cccggactca gaagactcag                         280
aggacagccc actaccgtgg gtggaagagc cacaacgttc                          320
ctgtacagtg agaaagtgcg ctgcgctcca ggccaccagg                          360
ggagtggagc ctgctggttg gaaggagatg cgctgtcatc                          400
tgcgcaccga tggctaccta tgcaag                                         426

<210> SEQ ID NO 13
<211> LENGTH: 25
<212> TYPE: PRT
<213> ORGANISM: Artificial Sequence
<220> FEATURE:
<223> OTHER INFORMATION: FR1 of a heavy chain variable region of clone1

<400> SEQUENCE: 13

Glu Val Gln Leu Leu Glu Ser Gly Gly Gly Leu Val Gln Pro Gly Gly
 1               5                  10                  15

Ser Leu Arg Leu Ser Cys Ala Ala Ser
            20                  25

<210> SEQ ID NO 14
<211> LENGTH: 10
<212> TYPE: PRT
```

-continued

```
<213> ORGANISM: Artificial Sequence
<220> FEATURE:
<223> OTHER INFORMATION: CDR1 of a heavy chain variable region of clone1

<400> SEQUENCE: 14

Gly Phe Thr Phe Ser Gly Tyr Asp Met Ser
1               5                   10

<210> SEQ ID NO 15
<211> LENGTH: 14
<212> TYPE: PRT
<213> ORGANISM: Artificial Sequence
<220> FEATURE:
<223> OTHER INFORMATION: FR2 of a heavy chain variable region of clone1

<400> SEQUENCE: 15

Trp Val Arg Gln Ala Pro Gly Lys Gly Leu Glu Trp Val Ser
1               5                   10

<210> SEQ ID NO 16
<211> LENGTH: 17
<212> TYPE: PRT
<213> ORGANISM: Artificial Sequence
<220> FEATURE:
<223> OTHER INFORMATION: CDR2 of a heavy chain variable region of clone1

<400> SEQUENCE: 16

Gly Ile Tyr Pro Asp Gly Gly Asn Thr Tyr Tyr Ala Asp Ser Val Lys
1               5                   10                  15

Gly

<210> SEQ ID NO 17
<211> LENGTH: 32
<212> TYPE: PRT
<213> ORGANISM: Artificial Sequence
<220> FEATURE:
<223> OTHER INFORMATION: FR3 of a heavy chain variable region of clone1

<400> SEQUENCE: 17

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 18
<211> LENGTH: 12
<212> TYPE: PRT
<213> ORGANISM: Artificial Sequence
<220> FEATURE:
<223> OTHER INFORMATION: CDR3 of a heavy chain variable region of clone1

<400> SEQUENCE: 18

Gly Ala Thr Trp Trp Val Leu Gly Pro Phe Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: FR4 of a heavy chain variable region of clone1

<400> SEQUENCE: 19

Trp Gly Gln Gly Thr Leu Val Thr Val Ser Ser
1               5                   10
```

```
<210> SEQ ID NO 20
<211> LENGTH: 25
<212> TYPE: PRT
<213> ORGANISM: Artificial Sequence
<220> FEATURE:
<223> OTHER INFORMATION: FR1 of a heavy chain variable region of clone2

<400> SEQUENCE: 20

Glu Val Gln Leu Leu Glu Ser Gly Gly Gly Leu Val Gln Pro Gly Gly
 1               5                  10                  15

Ser Leu Arg Leu Ser Cys Ala Ala Ser
            20                  25

<210> SEQ ID NO 21
<211> LENGTH: 10
<212> TYPE: PRT
<213> ORGANISM: Artificial Sequence
<220> FEATURE:
<223> OTHER INFORMATION: CDR1 of a heavy chain variable region of clone2

<400> SEQUENCE: 21

Gly Phe Thr Phe Ser Ser Tyr Asp Met Ser
 1               5                  10

<210> SEQ ID NO 22
<211> LENGTH: 14
<212> TYPE: PRT
<213> ORGANISM: Artificial Sequence
<220> FEATURE:
<223> OTHER INFORMATION: FR2 of a heavy chain variable region of clone2

<400> SEQUENCE: 22

Trp Val Arg Gln Ala Pro Gly Lys Gly Leu Glu Trp Val Ser
 1               5                  10

<210> SEQ ID NO 23
<211> LENGTH: 17
<212> TYPE: PRT
<213> ORGANISM: Artificial Sequence
<220> FEATURE:
<223> OTHER INFORMATION: CDR2 of a heavy chain variable region of clone2

<400> SEQUENCE: 23

Val Ile Ser Pro Asp Ser Ser Ser Thr Tyr Tyr Ala Asp Ser Val Lys
 1               5                  10                  15

Gly

<210> SEQ ID NO 24
<211> LENGTH: 32
<212> TYPE: PRT
<213> ORGANISM: Artificial Sequence
<220> FEATURE:
<223> OTHER INFORMATION: FR3 of a heavy chain variable region of clone2

<400> SEQUENCE: 24

Arg Phe Thr Ile Ser Arg Asp Asn Ser Lys Asn Thr Leu His Leu Gln
 1               5                  10                  15

Met Asn Ser Leu Arg Ala Glu Asp Thr Ala Val Tyr Tyr Cys Ala Arg
            20                  25                  30

<210> SEQ ID NO 25
<211> LENGTH: 18
<212> TYPE: PRT
<213> ORGANISM: Artificial Sequence
<220> FEATURE:
```

```
<223> OTHER INFORMATION: CDR3 of a heavy chain variable region of clone2

<400> SEQUENCE: 25

His Thr Gly Trp Gln Ser Arg Pro His Thr Tyr Tyr Asp Tyr Gly Met
 1               5                  10                  15

Asp Val

<210> SEQ ID NO 26
<211> LENGTH: 22
<212> TYPE: PRT
<213> ORGANISM: Artificial Sequence
<220> FEATURE:
<223> OTHER INFORMATION: FR4 of a heavy chain variable region of clone2

<400> SEQUENCE: 26

Trp Gly Gln Gly Thr Leu Val Thr Val Ser Ser Trp Gly Gln Gly Thr
 1               5                  10                  15

Leu Val Thr Val Ser Ser
            20

<210> SEQ ID NO 27
<211> LENGTH: 25
<212> TYPE: PRT
<213> ORGANISM: Artificial Sequence
<220> FEATURE:
<223> OTHER INFORMATION: FR1 of a heavy chain variable region of clone3

<400> SEQUENCE: 27

Glu Val Gln Leu Leu Glu Ser Gly Gly Gly Leu Val Gln Pro Gly Gly
 1               5                  10                  15

Ser Leu Arg Leu Ser Cys Ala Ala Ser
            20                  25

<210> SEQ ID NO 28
<211> LENGTH: 10
<212> TYPE: PRT
<213> ORGANISM: Artificial Sequence
<220> FEATURE:
<223> OTHER INFORMATION: CDR1 of a heavy chain variable region of clone3

<400> SEQUENCE: 28

Gly Phe Thr Phe Ser Asp Tyr Tyr Met Ser
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: FR2 of a heavy chain variable region of clone3

<400> SEQUENCE: 29

Trp Val Arg Gln Ala Pro Gly Lys Gly Leu Glu Trp Val Ser
 1               5                  10

<210> SEQ ID NO 30
<211> LENGTH: 17
<212> TYPE: PRT
<213> ORGANISM: Artificial Sequence
<220> FEATURE:
<223> OTHER INFORMATION: CDR2 of a heavy chain variable region of clone3

<400> SEQUENCE: 30

Leu Ile Ser Tyr Asp Gly Gly Ser Thr Tyr Tyr Ala Asp Ser Val Lys
 1               5                  10                  15
```

```
<210> SEQ ID NO 31
<211> LENGTH: 32
<212> TYPE: PRT
<213> ORGANISM: Artificial Sequence
<220> FEATURE:
<223> OTHER INFORMATION: FR3 of a heavy chain variable region of clone3

<400> SEQUENCE: 31

Arg Phe Thr Ile Ser Arg Asp Asn Ser Lys Asn Thr Leu Tyr Leu Gln
  1               5                  10                  15

Met Asn Ser Leu Arg Ala Glu Asp Thr Ala Val Tyr Tyr Cys Ala Arg
             20                  25                  30

<210> SEQ ID NO 32
<211> LENGTH: 7
<212> TYPE: PRT
<213> ORGANISM: Artificial Sequence
<220> FEATURE:
<223> OTHER INFORMATION: CDR3 of a heavy chain variable region of clone3

<400> SEQUENCE: 32

Ser Asn Asp Trp Phe Asp Tyr
  1               5

<210> SEQ ID NO 33
<211> LENGTH: 11
<212> TYPE: PRT
<213> ORGANISM: Artificial Sequence
<220> FEATURE:
<223> OTHER INFORMATION: FR4 of a heavy chain variable region of clone3

<400> SEQUENCE: 33

Trp Gly Gln Gly Thr Leu Val Thr Val Ser Ser
  1               5                  10

<210> SEQ ID NO 34
<211> LENGTH: 25
<212> TYPE: PRT
<213> ORGANISM: Artificial Sequence
<220> FEATURE:
<223> OTHER INFORMATION: FR1 of a heavy chain variable region of clone4

<400> SEQUENCE: 34

Glu Val Gln Leu Leu Glu Ser Gly Gly Gly Leu Val Gln Pro Gly Gly
  1               5                  10                  15

Ser Leu Arg Leu Ser Cys Ala Ala Ser
             20                  25

<210> SEQ ID NO 35
<211> LENGTH: 10
<212> TYPE: PRT
<213> ORGANISM: Artificial Sequence
<220> FEATURE:
<223> OTHER INFORMATION: CDR1 of a heavy chain variable region of clone4

<400> SEQUENCE: 35

Gly Phe Thr Phe Ser Gly Tyr Tyr Met Ser
  1               5                  10

<210> SEQ ID NO 36
<211> LENGTH: 14
<212> TYPE: PRT
<213> ORGANISM: Artificial Sequence
```

```
<220> FEATURE:
<223> OTHER INFORMATION: FR2 of a heavy chain variable region of clone4

<400> SEQUENCE: 36

Trp Val Arg Gln Ala Pro Gly Lys Gly Leu Glu Trp Val Ser
 1               5                  10

<210> SEQ ID NO 37
<211> LENGTH: 17
<212> TYPE: PRT
<213> ORGANISM: Artificial Sequence
<220> FEATURE:
<223> OTHER INFORMATION: CDR2 of a heavy chain variable region of clone4

<400> SEQUENCE: 37

Val Ile Tyr Ser Gly Asp Gly Ser Thr Tyr Tyr Ala Asp Ser Val Lys
 1               5                  10                  15

Gly

<210> SEQ ID NO 38
<211> LENGTH: 32
<212> TYPE: PRT
<213> ORGANISM: Artificial Sequence
<220> FEATURE:
<223> OTHER INFORMATION: FR3 of a heavy chain variable region of clone4

<400> SEQUENCE: 38

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 39
<211> LENGTH: 12
<212> TYPE: PRT
<213> ORGANISM: Artificial Sequence
<220> FEATURE:
<223> OTHER INFORMATION: CDR3 of a heavy chain variable region of clone4

<400> SEQUENCE: 39

Gly Leu Asn Ser Ser Ser Ala Leu Pro Phe Asp Tyr
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: FR4 of a heavy chain variable region of clone4

<400> SEQUENCE: 40

Trp Gly Gln Gly Thr Leu Val Thr Val Ser Ser
 1               5                  10

<210> SEQ ID NO 41
<211> LENGTH: 22
<212> TYPE: PRT
<213> ORGANISM: Artificial Sequence
<220> FEATURE:
<223> OTHER INFORMATION: FR1 of a light chain variable region of clone1

<400> SEQUENCE: 41

Gln Ser Val Leu Thr Gln Pro Pro Ser Ala Ser Gly Thr Pro Gly Gln
 1               5                  10                  15

Arg Val Thr Ile Ser Cys
```

<210> SEQ ID NO 42
<211> LENGTH: 13
<212> TYPE: PRT
<213> ORGANISM: Artificial Sequence
<220> FEATURE:
<223> OTHER INFORMATION: CDR1 of a light chain variable region of clone1

<400> SEQUENCE: 42

Thr Gly Ser Ser Ser Asn Ile Gly Asn Asn Ser Val Thr
 1               5                  10

<210> SEQ ID NO 43
<211> LENGTH: 15
<212> TYPE: PRT
<213> ORGANISM: Artificial Sequence
<220> FEATURE:
<223> OTHER INFORMATION: FR2 of a light chain variable region of clone1

<400> SEQUENCE: 43

Trp Tyr Gln Gln Leu Pro Gly Thr Ala Pro Lys Leu Leu Ile Tyr
 1               5                  10                  15

<210> SEQ ID NO 44
<211> LENGTH: 7
<212> TYPE: PRT
<213> ORGANISM: Artificial Sequence
<220> FEATURE:
<223> OTHER INFORMATION: CDR2 of a light chain variable region of clone1

<400> SEQUENCE: 44

Ala Asp Ser His Arg Pro Ser
 1               5

<210> SEQ ID NO 45
<211> LENGTH: 32
<212> TYPE: PRT
<213> ORGANISM: Artificial Sequence
<220> FEATURE:
<223> OTHER INFORMATION: FR3 of a light chain variable region of clone1

<400> SEQUENCE: 45

Gly Val Pro Asp Arg Phe Ser Gly Ser Lys Ser Gly Thr Ser Ala Ser
 1               5                  10                  15

Leu Ala Ile Ser Gly Leu Arg Ser Glu Asp Glu Ala Asp Tyr Tyr Cys
                20                  25                  30

<210> SEQ ID NO 46
<211> LENGTH: 11
<212> TYPE: PRT
<213> ORGANISM: Artificial Sequence
<220> FEATURE:
<223> OTHER INFORMATION: CDR3 of a light chain variable region of clone1

<400> SEQUENCE: 46

Gly Ala Trp Asp Asp Ser Leu Ser Gly Tyr Val
 1               5                  10

<210> SEQ ID NO 47
<211> LENGTH: 10
<212> TYPE: PRT
<213> ORGANISM: Artificial Sequence
<220> FEATURE:
<223> OTHER INFORMATION: FR4 of a light chain variable region of clone1

<400> SEQUENCE: 47

```
Phe Gly Gly Gly Thr Lys Leu Thr Val Leu
  1               5                  10

<210> SEQ ID NO 48
<211> LENGTH: 22
<212> TYPE: PRT
<213> ORGANISM: Artificial Sequence
<220> FEATURE:
<223> OTHER INFORMATION: FR1 of a light chain variable region of clone2

<400> SEQUENCE: 48

Gln Ser Val Leu Thr Gln Pro Pro Ser Ala Ser Gly Thr Pro Gly Gln
  1               5                  10                  15

Arg Val Thr Ile Ser Cys
              20

<210> SEQ ID NO 49
<211> LENGTH: 13
<212> TYPE: PRT
<213> ORGANISM: Artificial Sequence
<220> FEATURE:
<223> OTHER INFORMATION: CDR1 of a light chain variable region of clone2

<400> SEQUENCE: 49

Ser Gly Ser Ser Ser Asn Ile Gly Asn Asn Ala Val Thr
  1               5                  10

<210> SEQ ID NO 50
<211> LENGTH: 15
<212> TYPE: PRT
<213> ORGANISM: Artificial Sequence
<220> FEATURE:
<223> OTHER INFORMATION: FR2 of a light chain variable region of clone2

<400> SEQUENCE: 50

Trp Tyr Gln Gln Leu Pro Gly Thr Ala Pro Lys Leu Leu Ile Tyr
  1               5                  10                  15

<210> SEQ ID NO 51
<211> LENGTH: 7
<212> TYPE: PRT
<213> ORGANISM: Artificial Sequence
<220> FEATURE:
<223> OTHER INFORMATION: CDR2 of a light chain variable region of clone2

<400> SEQUENCE: 51

Ser Asp Asn His Arg Pro Ser
  1               5

<210> SEQ ID NO 52
<211> LENGTH: 32
<212> TYPE: PRT
<213> ORGANISM: Artificial Sequence
<220> FEATURE:
<223> OTHER INFORMATION: FR3 of a light chain variable region of clone2

<400> SEQUENCE: 52

Gly Val Pro Asp Arg Phe Ser Gly Ser Lys Ser Gly Thr Ser Ala Ser
  1               5                  10                  15

Leu Ala Ile Ser Gly Leu Arg Ser Glu Asp Glu Ala Asp Tyr Tyr Cys
              20                  25                  30

<210> SEQ ID NO 53
<211> LENGTH: 11
<212> TYPE: PRT
```

-continued

<213> ORGANISM: Artificial Sequence
<220> FEATURE:
<223> OTHER INFORMATION: CDR3 of a light chain variable region of clone2

<400> SEQUENCE: 53

Gly Thr Trp Asp Ala Ser Leu Ser Gly Tyr Val
1               5                   10

<210> SEQ ID NO 54
<211> LENGTH: 10
<212> TYPE: PRT
<213> ORGANISM: Artificial Sequence
<220> FEATURE:
<223> OTHER INFORMATION: FR4 of a light chain variable region of clone2

<400> SEQUENCE: 54

Phe Gly Gly Gly Thr Lys Leu Thr Val Leu
1               5                   10

<210> SEQ ID NO 55
<211> LENGTH: 22
<212> TYPE: PRT
<213> ORGANISM: Artificial Sequence
<220> FEATURE:
<223> OTHER INFORMATION: FR1 of a light chain variable region of clone3

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 56
<211> LENGTH: 13
<212> TYPE: PRT
<213> ORGANISM: Artificial Sequence
<220> FEATURE:
<223> OTHER INFORMATION: CDR1 of a light chain variable region of clone3

<400> SEQUENCE: 56

Ser Gly Ser Ser Ser Asn Ile Gly Ser Asn Asn Val Tyr
1               5                   10

<210> SEQ ID NO 57
<211> LENGTH: 15
<212> TYPE: PRT
<213> ORGANISM: Artificial Sequence
<220> FEATURE:
<223> OTHER INFORMATION: FR2 of a light chain variable region of clone3

<400> SEQUENCE: 57

Trp Tyr Gln Gln Leu Pro Gly Thr Ala Pro Lys Leu Leu Ile Tyr
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: CDR2 of a light chain variable region of clone3

<400> SEQUENCE: 58

Tyr Asp Ser Gln Arg Pro Ser
1               5

<210> SEQ ID NO 59

```
<211> LENGTH: 32
<212> TYPE: PRT
<213> ORGANISM: Artificial Sequence
<220> FEATURE:
<223> OTHER INFORMATION: FR3 of a light chain variable region of clone3

<400> SEQUENCE: 59

Gly Val Pro Asp Arg Phe Ser Gly Ser Lys Ser Gly Thr Ser Ala Ser
 1               5                  10                  15

Leu Ala Ile Ser Gly Leu Arg Ser Glu Asp Glu Ala Asp Tyr Tyr Cys
            20                  25                  30

<210> SEQ ID NO 60
<211> LENGTH: 11
<212> TYPE: PRT
<213> ORGANISM: Artificial Sequence
<220> FEATURE:
<223> OTHER INFORMATION: CDR3 of a light chain variable region of clone3

<400> SEQUENCE: 60

Gly Ala Trp Asp Asp Ser Leu Ser Ala Tyr Val
 1               5                  10

<210> SEQ ID NO 61
<211> LENGTH: 10
<212> TYPE: PRT
<213> ORGANISM: Artificial Sequence
<220> FEATURE:
<223> OTHER INFORMATION: FR4 of a light chain variable region of clone3

<400> SEQUENCE: 61

Phe Gly Gly Gly Thr Lys Leu Thr Val Leu
 1               5                  10

<210> SEQ ID NO 62
<211> LENGTH: 22
<212> TYPE: PRT
<213> ORGANISM: Artificial Sequence
<220> FEATURE:
<223> OTHER INFORMATION: FR1 of a light chain variable region of clone4

<400> SEQUENCE: 62

Gln Ser Val Leu Thr Gln Pro Pro Ser Ala Ser Gly Thr Pro Gly Gln
 1               5                  10                  15

Arg Val Thr Ile Ser Cys
            20

<210> SEQ ID NO 63
<211> LENGTH: 13
<212> TYPE: PRT
<213> ORGANISM: Artificial Sequence
<220> FEATURE:
<223> OTHER INFORMATION: CDR1 of a light chain variable region of clone4

<400> SEQUENCE: 63

Ser Gly Ser Ser Ser Asn Ile Gly Ser Asn Ala Val Asn
 1               5                  10

<210> SEQ ID NO 64
<211> LENGTH: 15
<212> TYPE: PRT
<213> ORGANISM: Artificial Sequence
<220> FEATURE:
<223> OTHER INFORMATION: FR2 of a light chain variable region of clone4

<400> SEQUENCE: 64
```

-continued

```
Trp Tyr Gln Gln Leu Pro Gly Thr Ala Pro Lys Leu Leu Ile Tyr
 1               5                  10                  15

<210> SEQ ID NO 65
<211> LENGTH: 7
<212> TYPE: PRT
<213> ORGANISM: Artificial Sequence
<220> FEATURE:
<223> OTHER INFORMATION: CDR2 of a light chain variable region of clone4

<400> SEQUENCE: 65

Ala Asp Ser Asn Arg Pro Ser
 1               5

<210> SEQ ID NO 66
<211> LENGTH: 32
<212> TYPE: PRT
<213> ORGANISM: Artificial Sequence
<220> FEATURE:
<223> OTHER INFORMATION: FR3 of a light chain variable region of clone4

<400> SEQUENCE: 66

Gly Val Pro Asp Arg Phe Ser Gly Ser Lys Ser Gly Thr Ser Ala Ser
 1               5                  10                  15

Leu Ala Ile Ser Gly Leu Arg Ser Glu Asp Glu Ala Asp Tyr Tyr Cys
             20                  25                  30

<210> SEQ ID NO 67
<211> LENGTH: 11
<212> TYPE: PRT
<213> ORGANISM: Artificial Sequence
<220> FEATURE:
<223> OTHER INFORMATION: CDR3 of a light chain variable region of clone4

<400> SEQUENCE: 67

Gly Ser Trp Asp Tyr Ser Leu Ser Ala Tyr Val
 1               5                  10

<210> SEQ ID NO 68
<211> LENGTH: 10
<212> TYPE: PRT
<213> ORGANISM: Artificial Sequence
<220> FEATURE:
<223> OTHER INFORMATION: FR4 of a light chain variable region of clone4

<400> SEQUENCE: 68

Phe Gly Gly Gly Thr Lys Leu Thr Val Leu
 1               5                  10

<210> SEQ ID NO 69
<211> LENGTH: 75
<212> TYPE: DNA
<213> ORGANISM: Artificial Sequence
<220> FEATURE:
<223> OTHER INFORMATION: FR1 of a heavy chain variable region of clone1

<400> SEQUENCE: 69
gaggtgcagc tgttggagtc tgggggaggc ttggtacagc                          40
ctggggggtc cctgagactc tcctgtgcag cctct                               75

<210> SEQ ID NO 70
<211> LENGTH: 30
<212> TYPE: DNA
<213> ORGANISM: Artificial Sequence
<220> FEATURE:
<223> OTHER INFORMATION: CDR1 of a heavy chain variable region of clone1
```

<400> SEQUENCE: 70
ggattcacct ttagcggtta tgatatgagc                                          30

<210> SEQ ID NO 71
<211> LENGTH: 42
<212> TYPE: DNA
<213> ORGANISM: Artificial Sequence
<220> FEATURE:
<223> OTHER INFORMATION: FR2 of a heavy chain variable region of clone1

<400> SEQUENCE: 71
tgggtccgcc aggctccagg gaaggggctg gagtgggtct                                40
ca                                                                        42

<210> SEQ ID NO 72
<211> LENGTH: 51
<212> TYPE: DNA
<213> ORGANISM: Artificial Sequence
<220> FEATURE:
<223> OTHER INFORMATION: CDR2 of a heavy chain variable region of clone1

<400> SEQUENCE: 72
gggatctatc ctgatggtgg taatacatat tacgctgatt                                40
ctgtaaaagg t                                                              51

<210> SEQ ID NO 73
<211> LENGTH: 96
<212> TYPE: DNA
<213> ORGANISM: Artificial Sequence
<220> FEATURE:
<223> OTHER INFORMATION: FR3 of a heavy chain variable region of clone1

<400> SEQUENCE: 73
cggttcacca tctccagaga caattccaag aacacgctgt                                40
atctgcaaat gaacagcctg agagccgagg acacggccgt                                80
gtattactgt gcgaga                                                         96

<210> SEQ ID NO 74
<211> LENGTH: 36
<212> TYPE: DNA
<213> ORGANISM: Artificial Sequence
<220> FEATURE:
<223> OTHER INFORMATION: CDR3 of a heavy chain variable region of clone1

<400> SEQUENCE: 74
ggtgctacgt ggtgggtgct tggtcctttc gactac                                   36

<210> SEQ ID NO 75
<211> LENGTH: 33
<212> TYPE: DNA
<213> ORGANISM: Artificial Sequence
<220> FEATURE:
<223> OTHER INFORMATION: FR4 of a heavy chain variable region of clone1

<400> SEQUENCE: 75
tggggccagg gtacactggt caccgtgagc tca                                      33

<210> SEQ ID NO 76
<211> LENGTH: 66
<212> TYPE: DNA
<213> ORGANISM: Artificial Sequence
<220> FEATURE:

<223> OTHER INFORMATION: FR1 of a light chain variable region of clone1

<400> SEQUENCE: 76
cagtctgtgc tgactcagcc accctcagcg tctgggaccc 40
ccgggcagag ggtcaccatc tcttgt 66

<210> SEQ ID NO 77
<211> LENGTH: 39
<212> TYPE: DNA
<213> ORGANISM: Artificial Sequence
<220> FEATURE:
<223> OTHER INFORMATION: CDR1 of a light chain variable region of clone1

<400> SEQUENCE: 77
actggctctt catctaatat tggcaataat tctgtcacc 39

<210> SEQ ID NO 78
<211> LENGTH: 45
<212> TYPE: DNA
<213> ORGANISM: Artificial Sequence
<220> FEATURE:
<223> OTHER INFORMATION: FR2 of a light chain variable region of clone1

<400> SEQUENCE: 78
tggtaccagc agctcccagg aacggccccc aaactcctca 40
tctat 45

<210> SEQ ID NO 79
<211> LENGTH: 21
<212> TYPE: DNA
<213> ORGANISM: Artificial Sequence
<220> FEATURE:
<223> OTHER INFORMATION: CDR2 of a light chain variable region of clone1

<400> SEQUENCE: 79
gctgatagtc atcggccaag c 21

<210> SEQ ID NO 80
<211> LENGTH: 96
<212> TYPE: DNA
<213> ORGANISM: Artificial Sequence
<220> FEATURE:
<223> OTHER INFORMATION: FR3 of a light chain variable region of clone1

<400> SEQUENCE: 80
ggggtccctg accgattctc tggctccaag tctggcacct 40
cagcctccct ggccatcagt gggctccggt ccgaggatga 80
ggctgattat tactgt 96

<210> SEQ ID NO 81
<211> LENGTH: 33
<212> TYPE: DNA
<213> ORGANISM: Artificial Sequence
<220> FEATURE:
<223> OTHER INFORMATION: CDR3 of a light chain variable region of clone1

<400> SEQUENCE: 81
ggtgcttggg atgatagcct gagtggttat gtc 33

<210> SEQ ID NO 82
<211> LENGTH: 30
<212> TYPE: DNA
<213> ORGANISM: Artificial Sequence

```
<220> FEATURE:
<223> OTHER INFORMATION: FR4 of a light chain variable region of clone1

<400> SEQUENCE: 82
ttcggcggag gcaccaagct gacggtccta                                          30

<210> SEQ ID NO 83
<211> LENGTH: 75
<212> TYPE: DNA
<213> ORGANISM: Artificial Sequence
<220> FEATURE:
<223> OTHER INFORMATION: FR1 of a heavy chain variable region of clone2

<400> SEQUENCE: 83
gaggtgcagc tgttggagtc tgggggaggc ttggtacagc                               40
ctggggggtc cctgagactc tcctgtgcag cctct                                    75

<210> SEQ ID NO 84
<211> LENGTH: 30
<212> TYPE: DNA
<213> ORGANISM: Artificial Sequence
<220> FEATURE:
<223> OTHER INFORMATION: CDR1 of a heavy chain variable region of clone2

<400> SEQUENCE: 84
ggattcacct ttagcagtta tgatatgagc                                          30

<210> SEQ ID NO 85
<211> LENGTH: 42
<212> TYPE: DNA
<213> ORGANISM: Artificial Sequence
<220> FEATURE:
<223> OTHER INFORMATION: FR2 of a heavy chain variable region of clone2

<400> SEQUENCE: 85
tgggtccgcc aggctccagg gaaggggctg gagtgggtct                               40
ca                                                                        42

<210> SEQ ID NO 86
<211> LENGTH: 51
<212> TYPE: DNA
<213> ORGANISM: Artificial Sequence
<220> FEATURE:
<223> OTHER INFORMATION: CDR2 of a heavy chain variable region of clone2

<400> SEQUENCE: 86
gtgatctctc ctgatagtag tagtacatat tacgctgatt                               40
ctgtaaaagg t                                                              51

<210> SEQ ID NO 87
<211> LENGTH: 96
<212> TYPE: DNA
<213> ORGANISM: Artificial Sequence
<220> FEATURE:
<223> OTHER INFORMATION: FR3 of a heavy chain variable region of clone2

<400> SEQUENCE: 87
cggttcacca tctccagaga caattccaag aacacgctgc                               40
atctgcaaat gaacagcctg agagccgagg acacggccgt                               80
gtattactgt gcgaga                                                         96

<210> SEQ ID NO 88
```

```
<211> LENGTH: 54
<212> TYPE: DNA
<213> ORGANISM: Artificial Sequence
<220> FEATURE:
<223> OTHER INFORMATION: CDR3 of a heavy chain variable region of clone2

<400> SEQUENCE: 88
catactggtt ggcagagtcg gcctcatacg tattatgatt                           40
atggtatgga cgtc                                                      54

<210> SEQ ID NO 89
<211> LENGTH: 33
<212> TYPE: DNA
<213> ORGANISM: Artificial Sequence
<220> FEATURE:
<223> OTHER INFORMATION: FR4 of a heavy chain variable region of clone2

<400> SEQUENCE: 89
tggggccagg gtacactggt caccgtgagc tca                                 33

<210> SEQ ID NO 90
<211> LENGTH: 66
<212> TYPE: DNA
<213> ORGANISM: Artificial Sequence
<220> FEATURE:
<223> OTHER INFORMATION: FR1 of a light chain variable region of clone2

<400> SEQUENCE: 90
cagtctgtgc tgactcagcc accctcagcg tctgggaccc                          40
ccgggcagag ggtcaccatc tcttgt                                         66

<210> SEQ ID NO 91
<211> LENGTH: 39
<212> TYPE: DNA
<213> ORGANISM: Artificial Sequence
<220> FEATURE:
<223> OTHER INFORMATION: CDR1 of a light chain variable region of clone2

<400> SEQUENCE: 91
agtggctctt catctaatat tggcaataat gctgtcacc                           39

<210> SEQ ID NO 92
<211> LENGTH: 45
<212> TYPE: DNA
<213> ORGANISM: Artificial Sequence
<220> FEATURE:
<223> OTHER INFORMATION: FR2 of a light chain variable region of clone2

<400> SEQUENCE: 92
tggtaccagc agctcccagg aacggccccc aaactcctca                          40
tctat                                                                45

<210> SEQ ID NO 93
<211> LENGTH: 21
<212> TYPE: DNA
<213> ORGANISM: Artificial Sequence
<220> FEATURE:
<223> OTHER INFORMATION: CDR2 of a light chain variable region of clone2

<400> SEQUENCE: 93
tctgataatc atcggccaag c                                              21

<210> SEQ ID NO 94
<211> LENGTH: 96
```

```
<212> TYPE: DNA
<213> ORGANISM: Artificial Sequence
<220> FEATURE:
<221> NAME/KEY: Variation
<222> LOCATION: 48
<223> OTHER INFORMATION: FR3 of a light chain variable region of clone2
<220> FEATURE:
<221> NAME/KEY: Variation
<222> LOCATION: 48
<223> OTHER INFORMATION: a, t, c or g

<400> SEQUENCE: 94
ggggtccctg accgattctc tggctccaag tctggcacct                          40
cagcctcnct ggccatcagt gggctccggt ccgaggatga                          80
ggctgattat tactgt                                                    96

<210> SEQ ID NO 95
<211> LENGTH: 33
<212> TYPE: DNA
<213> ORGANISM: Artificial Sequence
<220> FEATURE:
<223> OTHER INFORMATION: CDR3 of a light chain variable region of clone2

<400> SEQUENCE: 95
ggtacttggg atgctagcct gagtggttat gtc                                 33

<210> SEQ ID NO 96
<211> LENGTH: 30
<212> TYPE: DNA
<213> ORGANISM: Artificial Sequence
<220> FEATURE:
<223> OTHER INFORMATION: FR4 of a light chain variable region of clone2

<400> SEQUENCE: 96
ttcggcggag gcaccaagct gacggtccta                                     30

<210> SEQ ID NO 97
<211> LENGTH: 75
<212> TYPE: DNA
<213> ORGANISM: Artificial Sequence
<220> FEATURE:
<223> OTHER INFORMATION: FR1 of a heavy chain variable region of clone3

<400> SEQUENCE: 97
gaggtgcagc tgttggagtc tgggggaggc ttggtacagc                          40 ctgggggtc cctgagactc tcctgtgcag cctct                                75

<210> SEQ ID NO 98
<211> LENGTH: 30
<212> TYPE: DNA
<213> ORGANISM: Artificial Sequence
<220> FEATURE:
<223> OTHER INFORMATION: CDR1 of a heavy chain variable region of clone3

<400> SEQUENCE: 98
ggattcacct ttagcgatta ttatatgagc                                     30

<210> SEQ ID NO 99
<211> LENGTH: 42
<212> TYPE: DNA
<213> ORGANISM: Artificial Sequence
<220> FEATURE:
<223> OTHER INFORMATION: FR2 of a heavy chain variable region of clone3

<400> SEQUENCE: 99
```

```
tgggtccgcc aggctccagg gaaggggctg gagtgggtct                   40
ca                                                            42

<210> SEQ ID NO 100
<211> LENGTH: 51
<212> TYPE: DNA
<213> ORGANISM: Artificial Sequence
<220> FEATURE:
<223> OTHER INFORMATION: CDR2 of a heavy chain variable region of clone3

<400> SEQUENCE: 100
ttgatctctt atgatggtgg tagtacatat tacgctgatt                   40
ctgtaaaagg t                                                  51

<210> SEQ ID NO 101
<211> LENGTH: 96
<212> TYPE: DNA
<213> ORGANISM: Artificial Sequence
<220> FEATURE:
<223> OTHER INFORMATION: FR3 of a heavy chain variable region of clone3

<400> SEQUENCE: 101
cggttcacca tctccagaga caattccaag aacacgctgt                   40
atctgcaaat gaacagcctg agagccgagg acacggccgt                   80
gtattactgt gcgaga                                             96

<210> SEQ ID NO 102
<211> LENGTH: 21
<212> TYPE: DNA
<213> ORGANISM: Artificial Sequence
<220> FEATURE:
<223> OTHER INFORMATION: CDR3 of a heavy chain variable region of clone3

<400> SEQUENCE: 102
agtaatgatt ggttcgacta c                                       21

<210> SEQ ID NO 103
<211> LENGTH: 33
<212> TYPE: DNA
<213> ORGANISM: Artificial Sequence
<220> FEATURE:
<223> OTHER INFORMATION: FR4 of a heavy chain variable region of clone3

<400> SEQUENCE: 103
tggggccagg gtacactggt caccgtgagc tca                          33

<210> SEQ ID NO 104
<211> LENGTH: 66
<212> TYPE: DNA
<213> ORGANISM: Artificial Sequence
<220> FEATURE:
<223> OTHER INFORMATION: FR1 of a light chain variable region of clone3

<400> SEQUENCE: 104
cagtctgtgc tgactcagcc accctcagcg tctgggaccc                   40
ccgggcagag ggtcaccatc tcttgt                                  66

<210> SEQ ID NO 105
<211> LENGTH: 39
<212> TYPE: DNA
<213> ORGANISM: Artificial Sequence
<220> FEATURE:
<223> OTHER INFORMATION: CDR1 of a light chain variable region of clone3
```

<400> SEQUENCE: 105
agtggctctt catctaatat tggcagtaat aatgtctac                    39

<210> SEQ ID NO 106
<211> LENGTH: 45
<212> TYPE: DNA
<213> ORGANISM: Artificial Sequence
<220> FEATURE:
<223> OTHER INFORMATION: FR2 of a light chain variable region of clone3

<400> SEQUENCE: 106
tggtaccagc agctcccagg aacggctccc aaactcctca                   40
tctat                                                         45

<210> SEQ ID NO 107
<211> LENGTH: 21
<212> TYPE: DNA
<213> ORGANISM: Artificial Sequence
<220> FEATURE:
<223> OTHER INFORMATION: CDR2 of a light chain variable region of clone3

<400> SEQUENCE: 107
tatgatagtc agcggccaag c                                       21

<210> SEQ ID NO 108
<211> LENGTH: 96
<212> TYPE: DNA
<213> ORGANISM: Artificial Sequence
<220> FEATURE:
<223> OTHER INFORMATION: FR3 of a light chain variable region of clone3

<400> SEQUENCE: 108
ggggtccctg accgattctc tggctccaag tctggcacct                   40
cagcctccct ggccatcagt gggctccggt ccgaggatga                   80
ggctgattat tactgt                                             96

<210> SEQ ID NO 109
<211> LENGTH: 33
<212> TYPE: DNA
<213> ORGANISM: Artificial Sequence
<220> FEATURE:
<223> OTHER INFORMATION: CDR3 of a light chain variable region of clone3

<400> SEQUENCE: 109
ggtgcttggg atgatagcct gagtgcttat gtc                          33

<210> SEQ ID NO 110
<211> LENGTH: 30
<212> TYPE: DNA
<213> ORGANISM: Artificial Sequence
<220> FEATURE:
<223> OTHER INFORMATION: FR4 of a light chain variable region of clone3

<400> SEQUENCE: 110
ttcggcggag gcaccaagct gacggtccta                              30

<210> SEQ ID NO 111
<211> LENGTH: 75
<212> TYPE: DNA
<213> ORGANISM: Artificial Sequence
<220> FEATURE:
<223> OTHER INFORMATION: FR1 of a heavy chain variable region of clone4

<400> SEQUENCE: 111
gaggtgcagc tgttggagtc tgggggaggc ttggtacagc    40
ctggggggtc cctgagactc tcctgtgcag cctct    75

<210> SEQ ID NO 112
<211> LENGTH: 30
<212> TYPE: DNA
<213> ORGANISM: Artificial Sequence
<220> FEATURE:
<223> OTHER INFORMATION: CDR1 of a heavy chain variable region of clone4

<400> SEQUENCE: 112
ggattcacct ttagcggtta ttatatgagc    30

<210> SEQ ID NO 113
<211> LENGTH: 42
<212> TYPE: DNA
<213> ORGANISM: Artificial Sequence
<220> FEATURE:
<223> OTHER INFORMATION: FR2 of a heavy chain variable region of clone4

<400> SEQUENCE: 113
tgggtccgcc aggctccagg aagggggctg gagtgggtct    40
ca    42

<210> SEQ ID NO 114
<211> LENGTH: 51
<212> TYPE: DNA
<213> ORGANISM: Artificial Sequence
<220> FEATURE:
<223> OTHER INFORMATION: CDR2 of a heavy chain variable region of clone4

<400> SEQUENCE: 114
gtgatctatt ctggtgatgg tagtacatat tacgctgatt    40
ctgtaaaagg t    51

<210> SEQ ID NO 115
<211> LENGTH: 96
<212> TYPE: DNA
<213> ORGANISM: Artificial Sequence
<220> FEATURE:
<223> OTHER INFORMATION: FR3 of a heavy chain variable region of clone4

<400> SEQUENCE: 115
cggttcacca tctccagaga caactccaag aacacgctgt    40
atctgcaaat gaacagcctg agagccgagg acacggccgt    80
gtattactgt gcgaga    96

<210> SEQ ID NO 116
<211> LENGTH: 36
<212> TYPE: DNA
<213> ORGANISM: Artificial Sequence
<220> FEATURE:
<223> OTHER INFORMATION: CDR3 of a heavy chain variable region of clone4

<400> SEQUENCE: 116
ggtcttaatt cgtcttcggc tctgccgttc gactac    36

<210> SEQ ID NO 117
<211> LENGTH: 33
<212> TYPE: DNA
<213> ORGANISM: Artificial Sequence

```
<220> FEATURE:
<223> OTHER INFORMATION: FR4 of a heavy chain variable region of clone4

<400> SEQUENCE: 117
tggggccagg gtacactggt caccgtgagc tca                                33

<210> SEQ ID NO 118
<211> LENGTH: 66
<212> TYPE: DNA
<213> ORGANISM: Artificial Sequence
<220> FEATURE:
<223> OTHER INFORMATION: FR1 of a light chain variable region of clone4

<400> SEQUENCE: 118
cagtctgtgc tgactcagcc accctcagcg tctgggaccc                         40
ccgggcagag ggtcaccatc tcttgt                                        66

<210> SEQ ID NO 119
<211> LENGTH: 39
<212> TYPE: DNA
<213> ORGANISM: Artificial Sequence
<220> FEATURE:
<223> OTHER INFORMATION: CDR1 of a light chain variable region of clone4

<400> SEQUENCE: 119
agtggctctt catctaatat tggcagtaat gctgtcaac                          39

<210> SEQ ID NO 120
<211> LENGTH: 45
<212> TYPE: DNA
<213> ORGANISM: Artificial Sequence
<220> FEATURE:
<223> OTHER INFORMATION: FR2 of a light chain variable region of clone4

<400> SEQUENCE: 120
tggtaccagc agctcccagg aacggccccc aaactcctca                         40
tctat                                                               45

<210> SEQ ID NO 121
<211> LENGTH: 21
<212> TYPE: DNA
<213> ORGANISM: Artificial Sequence
<220> FEATURE:
<223> OTHER INFORMATION: CDR2 of a light chain variable region of clone4

<400> SEQUENCE: 121
gctgatagta atcggccaag c                                             21

<210> SEQ ID NO 122
<211> LENGTH: 96
<212> TYPE: DNA
<213> ORGANISM: Artificial Sequence
<220> FEATURE:
<223> OTHER INFORMATION: FR3 of a light chain variable region of clone4

<400> SEQUENCE: 122
ggggtccctg accgattctc tggctccaag tctggcacct                         40
cagcctccct ggccatcagt gggctccggt ccgaggatga                         80
ggctgattat tactgt                                                   96

<210> SEQ ID NO 123
<211> LENGTH: 33
<212> TYPE: DNA
```

<213> ORGANISM: Artificial Sequence
<220> FEATURE:
<223> OTHER INFORMATION: CDR3 of a light chain variable region of clone4

<400> SEQUENCE: 123
ggttcttggg attatagcct gagtggttat gtc                          33

<210> SEQ ID NO 124
<211> LENGTH: 30
<212> TYPE: DNA
<213> ORGANISM: Artificial Sequence
<220> FEATURE:
<223> OTHER INFORMATION: FR4 of a light chain variable region of clone4

<400> SEQUENCE: 124
ttcggcggag gtaccaagct gacggtccta                              30

<210> SEQ ID NO 125
<211> LENGTH: 121
<212> TYPE: PRT
<213> ORGANISM: Artificial Sequence
<220> FEATURE:
<223> OTHER INFORMATION: a heavy chain variable region of clone1

<400> SEQUENCE: 125

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Gly Ile Tyr Pro Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Thr Trp Trp Val Leu Gly Pro Phe Asp Tyr Trp Gly
            100                 105                 110

Gln Gly Thr Leu Val Thr Val Ser Ser
        115                 120

<210> SEQ ID NO 126
<211> LENGTH: 127
<212> TYPE: PRT
<213> ORGANISM: Artificial Sequence
<220> FEATURE:
<223> OTHER INFORMATION: a heavy chain variable region of clone2

<400> SEQUENCE: 126

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Pro Asp Ser Ser Thr Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                    85                  90                  95

Ala Arg His Thr Gly Trp Gln Ser Arg Pro His Thr Tyr Tyr Asp Tyr
            100                 105                 110

Gly Met Asp Val Trp Gly Gln Gly Thr Leu Val Thr Val Ser Ser
        115                 120                 125

<210> SEQ ID NO 127
<211> LENGTH: 116
<212> TYPE: PRT
<213> ORGANISM: Artificial Sequence
<220> FEATURE:
<223> OTHER INFORMATION: a heavy chain variable region of clone3

<400> SEQUENCE: 127

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Leu Ile Ser Tyr Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Ser Asn Asp Trp Phe Asp Tyr Trp Gly Gln Gly Thr Leu Val
            100                 105                 110

Thr Val Ser Ser
        115

<210> SEQ ID NO 128
<211> LENGTH: 121
<212> TYPE: PRT
<213> ORGANISM: Artificial Sequence
<220> FEATURE:
<223> OTHER INFORMATION: a heavy chain variable region of clone4

<400> SEQUENCE: 128

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Gly Tyr
            20                  25                  30

Tyr Met Ser Trp Val Arg Gln Ala Pro Gly Lys Gly Leu Glu Trp Val
        35                  40                  45

Ser Val Ile Tyr Ser Gly Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Gly Leu Asn Ser Ser Ser Ala Leu Pro Phe Asp Tyr Trp Gly
            100                 105                 110

Gln Gly Thr Leu Val Thr Val Ser Ser
        115                 120

<210> SEQ ID NO 129

```
<211> LENGTH: 110
<212> TYPE: PRT
<213> ORGANISM: Artificial Sequence
<220> FEATURE:
<223> OTHER INFORMATION: a light chain variable region of clone1

<400> SEQUENCE: 129

Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Asn Asn
             20                  25                  30

Ser Val Thr Trp Tyr Gln Gln Leu Pro Gly Thr Ala Pro Lys Leu Leu
         35                  40                  45

Ile Tyr Ala Asp Ser His Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Asp Ser Leu
                 85                  90                  95

Ser Gly Tyr Val Phe Gly Gly Gly Thr Lys Leu Thr Val Leu
            100                 105                 110

<210>   SEQ ID NO 130
<211> LENGTH: 110
<212> TYPE: PRT
<213> ORGANISM: Artificial Sequence
<220> FEATURE:
<223> OTHER INFORMATION: a light chain variable region of clone2

<400> SEQUENCE: 130

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Asn Asn
             20                  25                  30

Ala Val Thr Trp Tyr Gln Gln Leu Pro Gly Thr Ala Pro Lys Leu Leu
         35                  40                  45

Ile Tyr Ser Asp Asn His Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Ala Ser Leu
                 85                  90                  95

Ser Gly Tyr Val Phe Gly Gly Gly Thr Lys Leu Thr Val Leu
            100                 105                 110

<210> SEQ ID NO 131
<211> LENGTH: 110
<212> TYPE: PRT
<213> ORGANISM: Artificial Sequence
<220> FEATURE:
<223> OTHER INFORMATION: a light chain variable region of clone3

<400> SEQUENCE: 131

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Asn
             20                  25                  30

Asn Val Tyr Trp Tyr Gln Gln Leu Pro Gly Thr Ala Pro Lys Leu Leu
         35                  40                  45
```

```
Ile Tyr Tyr Asp Ser Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Leu
                85                  90                  95

Ser Ala Tyr Val Phe Gly Gly Gly Thr Lys Leu Thr Val Leu
                100                 105                 110

<210> SEQ ID NO 132
<211> LENGTH: 110
<212> TYPE: PRT
<213> ORGANISM: Artificial Sequence
<220> FEATURE:
<223> OTHER INFORMATION: a light chain variable region of clone4

<400> SEQUENCE: 132

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Ala Val Asn Trp Tyr Gln Gln Leu Pro Gly Thr Ala Pro Lys Leu Leu
            35                  40                  45

Ile Tyr Ala Asp Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Leu
                100                 105                 110

<210> SEQ ID NO 133
<211> LENGTH: 383
<212> TYPE: DNA
<213> ORGANISM: Artificial Sequence
<220> FEATURE:
<223> OTHER INFORMATION: VH domains of clec14a-CTLD IgGs of Clone 1

<400> SEQUENCE: 133
gaggtgcagc tgttggagtc tgggggaggc ttggtacagc                40
ctggggggtc cctgagactc tcctgtgcag cctctggatt                80
tcctgtgcag cctctggatt cacctttagc ggttatgata               120
tgagctgggt ccgccaggct ccagggaagg ggctggagtg               160
ggtctcaggg atctatcctg atggtggtaa tacatattac               200
gctgattctg taaaaggtcg gttcaccatc tccagagaca               240
attccaagaa cacgctgtat ctgcaaatga acagcctgag               280
agccgaggac acggccgtgt attactgtgc gagaggtgct               320
acgtggtggg tgcttggtcc tttcgactac tggggccagg               360
gtacactggt caccgtgagc tca                                 383

<210> SEQ ID NO 134
<211> LENGTH: 330
<212> TYPE: DNA
<213> ORGANISM: Artificial Sequence
<220> FEATURE:
```

<223> OTHER INFORMATION: VL domains of clec14a-CTLD IgGs of Clone 1

<400> SEQUENCE: 134

| | |
|---|---|
| cagtctgtgc tgactcagcc accctcagcg tctgggaccc | 40 |
| ccgggcagag ggtcaccatc tcttgtactg gctcttcatc | 80 |
| taatattggc aataattctg tcacctggta ccagcagctc | 120 |
| ccaggaacgg cccccaaact cctcatctat gctgatagtc | 160 |
| atcggccaag cggggtccct gaccgattct ctggctccaa | 200 |
| gtctggcacc tcagcctccc tggccatcag tgggctccgg | 240 |
| tccgaggatg aggctgatta ttactgtggt gcttgggatg | 280 |
| atagcctgag tggttatgtc ttcggcggag gcaccaagct | 320 |
| gacggtccta | 330 |

<210> SEQ ID NO 135
<211> LENGTH: 381
<212> TYPE: DNA
<213> ORGANISM: Artificial Sequence
<220> FEATURE:
<223> OTHER INFORMATION: VH domains of clec14a-CTLD IgGs of Clone 2

<400> SEQUENCE: 135

| | |
|---|---|
| gaggtgcagc tgttggagtc tgggggaggc ttggtacagc | 40 |
| ctggggggtc cctgagactc tcctgtgcag cctctggatt | 80 |
| cacctttagc agttatgata tgagctgggt ccgccaggct | 120 |
| ccagggaagg ggctggagtg ggtctcagtg atctctcctg | 160 |
| atagtagtag tacatattac gctgattctg taaaaggtcg | 200 |
| gttcaccatc tccagagaca attccaagaa cacgctgcat | 240 |
| ctgcaaatga acagcctgag agccgaggac acggccgtgt | 280 |
| attactgtgc gagacatact ggttggcaga gtcggcctca | 320 |
| tacgtattat gattatggta tggacgtctg gggccagggt | 360 |
| acactggtca ccgtgagctc a | 381 |

<210> SEQ ID NO 136
<211> LENGTH: 330
<212> TYPE: DNA
<213> ORGANISM: Artificial Sequence
<220> FEATURE:
<221> NAME/KEY: Variation
<222> LOCATION: 219
<223> OTHER INFORMATION: VL domains of clec14a-CTLD IgGs of Clone 2
<220> FEATURE:
<221> NAME/KEY: Variation
<222> LOCATION: 219
<223> OTHER INFORMATION: a, t, c or g

<400> SEQUENCE: 136

| | |
|---|---|
| cagtctgtgc tgactcagcc accctcagcg tctgggaccc | 40 |
| ccgggcagag ggtcaccatc tcttgtagtg gctcttcatc | 80 |
| taatattggc aataatgctg tcacctggta ccagcagctc | 120 |
| ccaggaacgg cccccaaact cctcatctat tctgataatc | 160 |
| atcggccaag cggggtccct gaccgattct ctggctccaa | 200 |
| gtctggcacc tcagcctcnc tggccatcag tgggctccgg | 240 |

| | |
|---|---|
| tccgaggatg aggctgatta ttactgtggt acttgggatg | 280 |
| ctagcctgag tggttatgtc ttcggcggag gcaccaagct | 320 |
| gacggtccta | 330 |

<210> SEQ ID NO 137
<211> LENGTH: 348
<212> TYPE: DNA
<213> ORGANISM: Artificial Sequence
<220> FEATURE:
<223> OTHER INFORMATION: VH domains of clec14a-CTLD IgGs of Clone 3

<400> SEQUENCE: 137

| | |
|---|---|
| gaggtgcagc tgttggagtc tgggggaggc ttggtacagc | 40 |
| ctggggggtc cctgagactc tcctgtgcag cctctggatt | 80 |
| cacctttagc gattattata tgagctgggt ccgccaggct | 120 |
| ccagggaagg ggctggagtg ggtctcattg atctcttatg | 160 |
| atggtggtag tacatattac gctgattctg taaaaggtcg | 200 |
| gttcaccatc tccagagaca attccaagaa cacgctgtat | 240 |
| ctgcaaatga acagcctgag agccgaggac acggccgtgt | 280 |
| attactgtgc gagaagtaat gattggttcg actactgggg | 320 |
| ccagggtaca ctggtcaccg tgagctca | 348 |

<210> SEQ ID NO 138
<211> LENGTH: 330
<212> TYPE: DNA
<213> ORGANISM: Artificial Sequence
<220> FEATURE:
<223> OTHER INFORMATION: VL domains of clec14a-CTLD IgGs of Clone 3

<400> SEQUENCE: 138

| | |
|---|---|
| cagtctgtgc tgactcagcc accctcagcg tctgggaccc | 40 |
| ccgggcagag ggtcaccatc tcttgtagtg gctcttcatc | 80 |
| taatattggc agtaataatg tctactggta ccagcagctc | 120 |
| ccaggaacgg ctcccaaact cctcatctat tatgatagtc | 160 |
| agcggccaag cggggtccct gaccgattct ctggctccaa | 200 |
| gtctggcacc tcagcctccc tggccatcag tgggctccgg | 240 |
| tccgaggatg aggctgatta ttactgtggt gcttgggatg | 280 |
| atagcctgag tgcttatgtc ttcggcggag gcaccaagct | 320 |
| gacggtccta | 330 |

<210> SEQ ID NO 139
<211> LENGTH: 363
<212> TYPE: DNA
<213> ORGANISM: Artificial Sequence
<220> FEATURE:
<223> OTHER INFORMATION: VH domains of clec14a-CTLD IgGs of Clone 4

<400> SEQUENCE: 139

| | |
|---|---|
| gaggtgcagc tgttggagtc tgggggaggc ttggtacagc | 40 |
| ctggggggtc cctgagactc tcctgtgcag cctctggatt | 80 |
| cacctttagc ggttattata tgagctgggt ccgccaggct | 120 |

| | |
|---|---|
| ccagggaagg ggctggagtg gtctcagtg atctattctg | 160 |
| gtgatggtag tacatattac gctgattctg taaaaggtcg | 200 |
| gttcaccatc tccagagaca actccaagaa cacgctgtat | 240 |
| ctgcaaatga acagcctgag agccgaggac acggccgtgt | 280 |
| attactgtgc gagaggtctt aattcgtctt cggctctgcc | 320 |
| gttcgactac tggggccagg gtacactggt caccgtgagc | 360 |
| tca | 363 |

<210> SEQ ID NO 140
<211> LENGTH: 330
<212> TYPE: DNA
<213> ORGANISM: Artificial Sequence
<220> FEATURE:
<223> OTHER INFORMATION: VL domains of clec14a-CTLD IgGs of Clone 4

<400> SEQUENCE: 140

| | |
|---|---|
| cagtctgtgc tgactcagcc accctcagcg tctgggaccc | 40 |
| ccgggcagag ggtcaccatc tcttgtagtg gctcttcatc | 80 |
| taatattggc agtaatgctg tcaactggta ccagcagctc | 120 |
| ccaggaacgg ccccaaaact cctcatctat gctgatagta | 160 |
| atcggccaag cggggtccct gaccgattct ctggctccaa | 200 |
| gtctggcacc tcagcctccc tggccatcag tgggctccgg | 240 |
| tccgaggatg aggctgatta ttactgtggt tcttgggatt | 280 |
| atagcctgag tggttatgtc ttcggcggag gtaccaagct | 320 |
| gacggtccta | 330 |

<210> SEQ ID NO 141
<211> LENGTH: 142
<212> TYPE: PRT
<213> ORGANISM: Pan troglodytes
<220> FEATURE:
<221> NAME/KEY: DOMAIN
<222> LOCATION: (1)..(142)
<223> OTHER INFORMATION: Chimpanzee clec14a-lectin (a.a 31-172)

<400> SEQUENCE: 141

Cys Ser Ala Ser Gly Ala Cys Tyr Ser Leu His His Ala Thr Met Lys
 1               5                  10                  15

Arg Gln Ala Ala Glu Glu Ala Cys Ile Leu Arg Gly Gly Ala Leu Ser
            20                  25                  30

Thr Val Arg Ala Gly Ala Glu Leu Arg Ala Val Leu Ala Leu Leu Arg
        35                  40                  45

Ala Gly Pro Gly Pro Gly Gly Ser Lys Asp Leu Leu Phe Trp Val
    50                  55                  60

Ala Leu Glu Arg Arg Arg Ser His Cys Thr Leu Glu Asn Glu Pro Leu
65                  70                  75                  80

Arg Gly Phe Ser Trp Leu Ser Ser Asp Pro Gly Gly Leu Glu Ser Asp
                85                  90                  95

Thr Leu Gln Trp Val Glu Glu Pro Gln Arg Ser Cys Thr Ala Arg Arg
            100                 105                 110

Cys Ala Val Leu Gln Ala Thr Gly Gly Val Glu Pro Ala Gly Trp Lys
        115                 120                 125

Glu Met Arg Cys His Leu Arg Ala Asn Gly Tyr Leu Cys Lys
    130                 135                 140

```
                   130             135             140

<210> SEQ ID NO 142
<211> LENGTH: 426
<212> TYPE: DNA
<213> ORGANISM: Pan troglodytes
<220> FEATURE:
<221> NAME/KEY: exon
<222> LOCATION: (1)..(426)
<223> OTHER INFORMATION: Chimpanzee clec14a-lectin (nt 91-516)

<400> SEQUENCE: 142
tgctcggcct cggggggcctg ctacagcctg caccacgcta                40
ccatgaagcg gcaggcggcc gaggaggcct gcatcctgcg                80
aggtggggcg ctcagcaccg tgcgtgcggg cgccgagctg                120
cgcgctgtgc tcgcgctcct gcgggcaggc ccagggcccg               160 gaggggggctc caaagacctg ctgttctggg tcgcactgga              200
gcgcaggcgt tcccactgca ccctggagaa cgagcctttg               240
cggggtttct cctggctgtc ctccgacccc ggcggtctcg               280
aaagcgacac gctgcagtgg gtggaggagc cccaacgctc               320
ctgcaccgcg cggagatgcg cggtactcca ggccaccggt               360
ggggtcgagc ccgcaggctg gaaggagatg cgatgccacc               400
tgcgcgccaa cggctacctg tgcaag                              426
```